(12) United States Patent
Greene et al.

(10) Patent No.: US 7,662,374 B2
(45) Date of Patent: Feb. 16, 2010

(54) MONOCLONAL ANTIBODIES TO ACTIVATED ERBB FAMILY MEMBERS AND METHODS OF USE THEREOF

(75) Inventors: Mark I. Greene, Penn Valley, PA (US); Hongtao Zhang, Paoli, PA (US); Mark Richter, Philadelphia, PA (US); Ramachandran Murali, Swarthmore, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/213,292

(22) Filed: Aug. 5, 2002

(65) Prior Publication Data

US 2006/0073140 A1    Apr. 6, 2006

Related U.S. Application Data

(60) Provisional application No. 60/309,864, filed on Aug. 3, 2001.

(51) Int. Cl.
*A61K 39/395* (2006.01)
*C12P 21/08* (2006.01)
*C07K 16/28* (2006.01)
*G01N 33/53* (2006.01)
*G01N 33/534* (2006.01)
*G01N 33/574* (2006.01)

(52) U.S. Cl. .............. 424/130.1; 424/133.1; 424/135.1; 424/143.1; 424/178.1; 424/179.1; 424/181.1; 424/183.1; 435/7.1; 530/387.1; 530/387.3; 530/388.22; 530/391.3; 530/391.7

(58) Field of Classification Search .............. 530/388.1, 530/388.2, 387.3, 391.1, 391.3, 391.7, 300; 424/143.1, 133.1, 135.1, 136.1, 179.1, 183.1
See application file for complete search history.

(56) References Cited

U.S. PATENT DOCUMENTS

| | | | |
|---|---|---|---|
| 4,522,918 A | | 6/1985 | Schlom et al. |
| 5,338,532 A | * | 8/1994 | Tomalia et al. .............. 424/1.49 |
| 5,470,571 A | | 11/1995 | Herlyn et al. |
| 5,637,677 A | | 6/1997 | Greene et al. |
| 5,677,171 A | * | 10/1997 | Hudziak et al. .............. 435/7.23 |
| 5,705,157 A | * | 1/1998 | Greene ..................... 424/138.1 |
| 5,720,954 A | | 2/1998 | Hudziak et al. |
| 5,725,856 A | | 3/1998 | Hudziak et al. |
| 5,770,195 A | | 6/1998 | Hudziak et al. |
| 5,772,997 A | | 6/1998 | Hudziak et al. |
| 5,821,337 A | * | 10/1998 | Carter et al. .............. 530/387.3 |
| 5,874,400 A | * | 2/1999 | Sundelin et al. ................ 514/2 |
| 5,955,311 A | * | 9/1999 | Rockwell et al. ........... 435/69.1 |
| 5,968,511 A | * | 10/1999 | Akita et al. .............. 424/141.1 |
| 6,100,377 A | | 8/2000 | Greene |
| 6,165,464 A | | 12/2000 | Hudziak et al. |
| 6,252,050 B1 | * | 6/2001 | Ashkenazi et al. ........ 530/387.3 |
| 6,342,219 B1 | * | 1/2002 | Thorpe et al. ............ 424/145.1 |
| 6,417,168 B1 | | 7/2002 | Greene et al. |
| 6,627,196 B1 | * | 9/2003 | Baughman et al. ........ 424/138.1 |
| 6,949,245 B1 | * | 9/2005 | Sliwkowski .............. 424/143.1 |

OTHER PUBLICATIONS

Dermer et al, Bio/Technology 12: 320, 1994.*
Gura et al, Science 278: 1041-1042, Nov 1997.*
Stryer et al, in Biochemistry, Third edition, W H Freeman Company, New York, pp. 31-33, 1998.*
Kuby et al, Immunology, Second edition, pp. 86-96, 1994.*
McInnes et al, Biopoly 43: 339-366, 1997.*
Kumagai et al, PNAS 98(10): 5526-5531, May 2001.*
Bishayee et al, Biochemical Pharmacology 60: 1217-1223, 2000.*
Muyldermans et al, J Molecular Recognition 12: 131-140, 1999.*
Fendly et al, Cancer Res 50(5): 1550-8, Mar. 1990.*
Bishayee et al, Molecular Biology of the Cell 10: 525-536, Mar. 1999.*
Jackson et al, Molcular Endocrinology 13: 2175-2188, 1999.*
Qian et al, J Biological Chemistry 274(2): 574-583, 1999.*
Kumagai et al, Proc Natl Acad Sci 98(10): 5526-5531, May 8, 2001.*
Kobrin et al, J Immunology 146: 2017-2020, 1991.*
Barrios et al, J Molecular Recognition 17: 332-338, 2004.*
Rudikoff et al, Proc Natl Acad Sci USA 79: 1979, 1982.*
Scott et al, J biochemistry 266(22): 14300-14305, 1991.*
Samata et al, Proc. Natl. Acad. Sci. USA 91:1711, 1994.*
Landgraf et al, Biochemistry 39: 8503-8511, 2000.*
Witte et al, Cancer and Metastasis Reviews 17: 155-161, 1998.*
Yip et al, J Immunology 166: 5271-5278, Apr. 2001.*
Fendly et al, Cancer Research 50: 1550-1558, Mar. 1, 1990.*
Agus et al, Cancer Cell 2: 127-137, Aug. 2002.*
Baselga et al., 1998, "Recombinant Humanized Anti-HER2 Antibody (Herceptin™) Enhances the Antitumor Activity of Paclitaxel and Doxorubicin against HER2/*neu* Overexpressing Human Breast Cancer Xenografts", *Cancer Res.*, 58:2825-2831.
Borgelt et al., 1980, "The Palliation of Brain Metastases: Final Results of the First Two Studies by the Radiation Therapy Oncology Group", *Int. J. Radiat Oncol. Biol. Phys.*, 6:1-9.
Brown et al., 1994, "Demonstration by Two-Color Flow Cytometry That Tyrosine Kinase Activity Is Required for Down-Modulation of the Oncogenic neu Receptor", *DNA Cell Biol.*, 13:193-209.
Capone et al., 1984, "Relationship Between Antigen Density and Immunotherapeutic Response Elicited by Monoclonal Antibodies Against Solid Tumors", *JNCI*, 72:673-677.
Carter et al., 1992, "Humanization of an anti-p185$^{HER2}$ antibody for human cancer therapy", *PNAS*, 89:4285-9.
Christodoulides et al., 1993, "Immunization with synthetic peptides containing epitopes of the class 1 outer-membrane protein of *Neisseria meningitidis*: production of bactericidal antibodies on immunization with a cyclic peptide", *J. Genetic Microbiology*, 139:1729-1738.
Cohen, 1982, "A Native 170,000 Epidermal Growth Factor Receptor-Kinase Complex from Shed Plasma Membrane Vesicles", *J. Biol. Chem.*, 258:1523-1531.

(Continued)

*Primary Examiner*—Phuong Huynh
(74) *Attorney, Agent, or Firm*—Woodcock Washburn, LLP

(57) ABSTRACT

Antibodies which bind to activated members of the erbB, TNF, and IgSF family of receptors and pharmaceutical compositions comprising the same are disclosed. Peptides and mimetics of erbB, TNF, and IgSF receptors and pharmaceutical compositions comprising the same are also described. Methods of using such antibodies, peptides, and mimetics in tumor therapeutic, prophylactic, imaging and diagnostic applications are disclosed.

39 Claims, 3 Drawing Sheets

OTHER PUBLICATIONS

Di Blasio et al., 1993, "Noncoded Residues as Building Blocks in the Design of Specific Secondary Structures: Symmetrically Disubstituted Glycines and β-Alanine", *Biopolymers*, 33:1037-1049.

Di Fiore et al., 1987, "*erb*B-2 Is a Potent Oncogene When Overexpressed in NIH/3T3 Cells", *Science*, 237:178-182.

Doherty et al., 1999, "The *HER-2/neu*, receptor tyrosine kinase gene encodes a secreted autoinhibitor", *PNAS*, 96:10869-10874.

Dougall et al., 1994, "The *neu*-oncogene: signal transduction pathways, transformation mechanisms and evolving therapies", *Oncogene*, 2109-23.

Drebin et al., 1984, "Monoclonal antibodies identify a cell-surface antigen associated with an activated cellular oncogene", *Nature*, 312:545-8.

Drebin et al., 1986, "Inhibition of tumor growth by a monoclonal antibody reactive with an oncogene-encoded tumor antigen", *PNAS*, 83:9129-9133.

Drebin et al., 1986, "Development of Monoclonal Antibodies Reactive with the Product of the *neu* Oncogene", *Symp Fundam Cancer Res.*, 38:277-289.

Drebin et al., 1988, "Monoclonal antibodies reactive with distinct domains of the *neu* oncogene-encoded p185 molecule exert synergistic anti-tumor effects in vivo", *Oncogene*, 2:273-277.

Ferguson et al., "Extracellular domains drive homo- but not heterodimerization of erbB receptors", *EMBO J.*, 2000, 19:4632-4643.

Fernandez-Pol, 1985, "Epidermal Growth Factor Receptor of A431 Cells", *Biol., Chem.*, 260:5003-5011.

Hansen et al., 1989, "Re-examination and further development of a precise and rapid dye method for measuring cell growth/cell kill", *J. Immunol. Methods*, 119:203-210.

Heldin, 1995, "Dimerization of Cell Surface Receptors in Signal Transduction", *Cell*, 80:213-223.

Hruby, 1993, "Conformational and Topographical Considerations in the Design of Biologically Active Peptides", *Biopolymers*, 33:1073-1082.

Jacob et al., 1985, "Priming immunization against cholera toxin and *E. coli* heat-labile toxin by a cholera toxin short peptide-β-galactosidase hybrid synthesized in *E. coli*", *EMBO J.*, 4:3339-3343.

Koprowski et al., 1985, "Expression of the Receptor for Epidermal Growth Factor Correlates with Increased Dosage of Chromosome 7 in malignant Melanoma", *Somatic Cell and Molecular Genetics*, 11:297-302.

Kumagai et al., 2001, "The role of distinct p185$^{neu}$ extracellular subdomains for dimerization with the epidermal growth factor (EGF) receptor and EGF-mediated signaling", *PNAS*, 98:5526-5531.

Landgraf et al., 2000, "Hegerulin Reverses the Oligomerization of HER3", *Biochemistry*, 39:8503-8511.

LeBien et al., 1981, "Use of Monoclonal Antibodies, Morphology, and Cytochemistry to Probe the Cellular Heterogeneity of Acute Leukemia and Lymphoma", *Cancer Res.*, 41:4776-4780.

Magerstadt, M., 1991, "Antibody-Drug Conjugates, "Chemoimunoconjugates"", *Antibody Conjugates and Malignant Disease*, CRC Press, Boca Raton, USA, 110-152.

Manning et al., 1993, "Design of cyclic and linear peptide antagonists of vasopressin and oxytocin: current status and future directions", *Reg. Peptides*, 45:279-283.

Matsuyama et al., 1992, "A Novel Extracellular Cyclic Lipopeptide Which Promotes Flagellum-Dependent and -Independent Spreading Growth of *Serratia marcescens*", *J. Bacteriol.*, 174:1769-1776.

Murzin et al., 1995, "SCOP: A Structural Classification of Proteins Database for the Investigation of Sequences and Structures", *J. Mol. Biol.*, 247:536-540.

Nayak et al., 1998, "B Cell Responses to a Peptide Epitope. V. Kinetic Regulation of Repertoire Discrimination and Antibody Optimization for Epitope", *J. Immunol.*, 161:3510-3519.

O'Rourke et al., 1997, "Trans receptor inhibition of human glioblastoma cells by erbB family ectodomains", *PNAS*, 94:3250-55.

Park et al., 2000, "Rationally designed anti-HER2/neu peptide mimetic disables P185$^{HER2/neu}$ tyrosine kinases in vitro and in vivo", *Nature Biotech.*, 18:194-198.

Patel et al., 1999, "A cyclic peptide analogue of the loop III region of platelet-derived growth factor-BB is a synthetic antigen for the native protein", *J. Pept. Res.*, 53:68-74.

Peczuh et al., 2000, "Peptide and Protein Recognition by Designed Molecules", *Chem. Rev.*, 100:2479-2494.

Pegram et al., 1998, "Phase II Study of Receptor-Enhanced Chemosensitivity Using Recombinant Humanized Anti-p185$^{HER2/neu}$ Monoclonal Antibody Plus Cisplatin in Patients With HER2/*neu*-Overexpressing Metastatic Breast Cancer Refactory to Chemotherapy Treatment", *J. of Clin. Oncology*, 16:2659-2671.

Pinkas-Kramarski et al., 1997, "Differential expression of NDF/neuregulin receptors ErbB-3 and ErbB-4 and involvement in inhibition of neuronal differentiation", *Oncogene*, 15:2803-2815.

Posthumus et al., 1991, "Immunogenicity of Peptides Simulating a Neutralization of Epitope of Transmissible Gastroenteritis Virus", *Virology*, 182:371-375.

Qian et al., 1994, "Heterodimerization of epidermal growth factor receptor and wild-type or kinase-deficient Neu: A mechanism of interreceptor kinase activation and transphosphorylation", *PNAS*, 91:1500-1504.

Saragovi et al., 1991, "Design and Synthesis of a Mimetic from an Antibody Complementarity-Determining Region", *Science*, 253:792-795.

Saragovi et al., 1992, "Constrained Peptides and Mimetics as Probes of Protein Secondary Structure", *Immunomethods*, 1:5-9.

Simpson et al., 1993, "Influence of Location and Extent of Surgical Resection on Survival of Patients with Glioblastoma Multiforme: Results of Three Consecutive Radiation Therapy Oncology Group (RTOG) Clinical Trials", *Int. J. Radiat. Oncol. Biol. Phys.*, 26:239-244.

Talasaki et al., 1997, "Structure-based design and characterization of exocyclic peptidomimetics that inhibit TNFα binding to its receptor", *Nature Biotech.*, 15:1266-1270.

Tzahar and Yarden, 1998, "The ErbB-2/HER2 oncogenic receptor of adenocarcinomas: from orphanhood to multiple stromal ligands", *Biochim Biophys Acta*, 1377:M25-37.

Tzahar et al., 1997, "Bivalence of EGF-like ligands drives the ErbB signaling network", *EMBO J.*, 16:4938-4950.

Ullrich et al., 1984, "Human epidermal growth factor receptor cDNA sequence and aberrant expression of the amplified gene in A431 epidermoid carcinoma cells", *Nature*, 309:418-425.

Valero et al., 1995, "Cyclic peptides as conformationally restricted models of viral antigens: application to foot-and-mouth disease virus", *Biomed Pept Proteins Nucleic Acids*, 1:133-140.

van der Werf et al., 1994, "Ability of linear and cyclic peptides of neutralization antigenic site 1 of poliovirus type 1 to induce virus cross-reactive and neutralizing antibodies", *Res. Virol.*, 1994, 145:349-359.

Van Regenmortel, 1989, "Structural and functional approaches to the study of protein antigenicity", *Immunol. Today*, 10:266-272.

Van Regenmortel, 1996, "Mapping Epitope Structure and Activity: From One-Dimensional Prediction to Four-Dimensional Description of Antigenic Specificity", *Methods*, 9:465-472.

Wada et al., 1990, "Intermolecular Association of the p185$^{neu}$ Protein and EGF Receptor Modulates EGF Receptor Function", *Cell*, 61:1339-1347.

Wada et al., 1990, "Anti-receptor antibodies reverse the phenotype of cells transformed by two interacting proto-oncogene encoded receptor proteins", *Oncogene*, 5:489-495.

Williams et al., 1989, "Immune Response to a Molecularly Defined Internal Image Idiotype", *J. Immunol.*, 142:4392-4400.

Wood et al., 1992, "Novel cyclization chemistry especially suited for biologically derived, unprotected peptides", *J. Pep. Prot. Res.*, 39:533-539.

Zajchowski et al., 2001, "Identification of Gene Expression Profiles That Predict the Aggressive behavior of Breast Cancer Cells", *Cancer Res.*, 61:5168-5178.

Zhang et al., 2000, "New Perspectives on Anti-HER2/Neu Therapeutics", *Drug News Perspect*, 13:325-329.

Zutshi et al., 1998, "Inhibiting the assembly of protein-protein interfaces", *Curr Opin Chem Biol.*, 2:62-66.

* cited by examiner

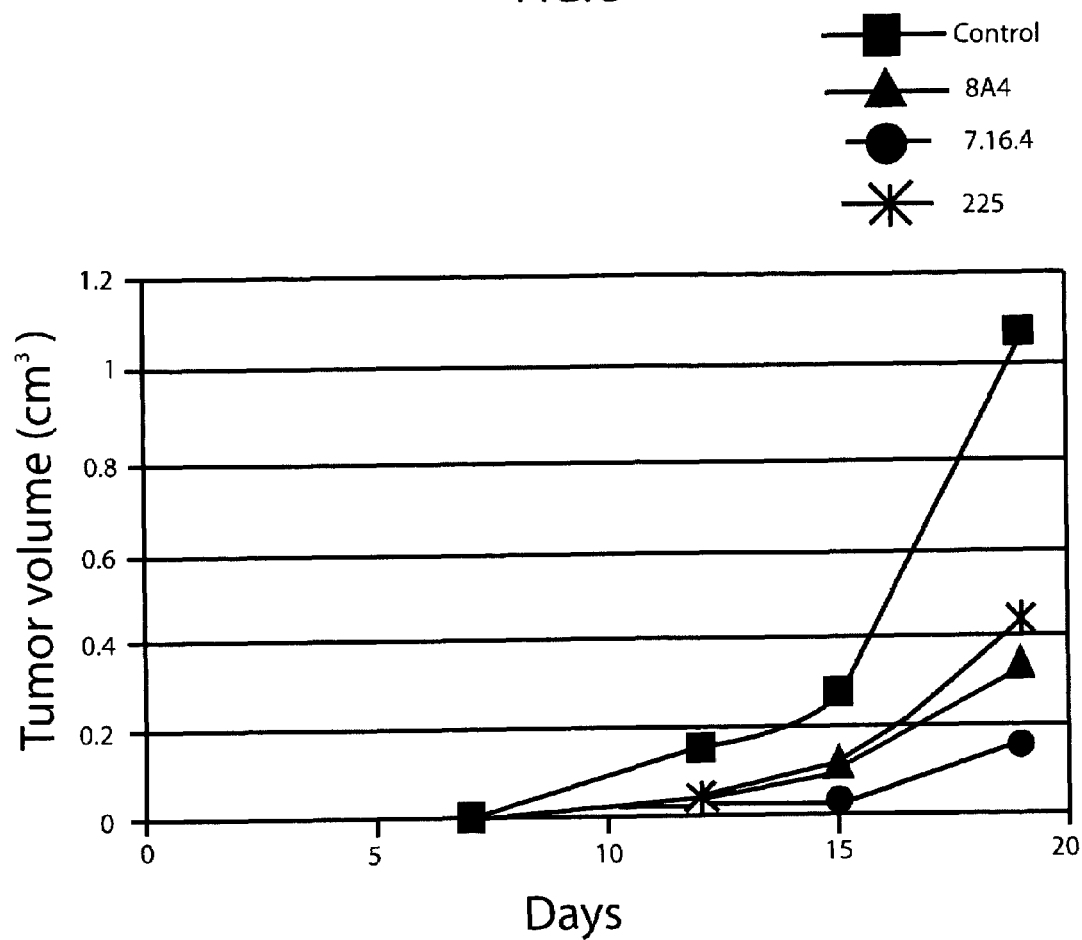

MONOCLONAL ANTIBODIES TO ACTIVATED ERBB FAMILY MEMBERS AND METHODS OF USE THEREOF

CROSS-REFERENCE TO RELATED APPLICATIONS

The present application claims the benefit of priority under 35 U.S.C. §119(e) of Provisional Application Ser. No. 60/309,864, filed Aug. 3, 2001, which is hereby incorporated herein by reference in its entirety.

GOVERNMENT SUPPORT

This work was supported by in part by NIH grant 5R01 CA55306. Pursuant to the terms of that grant, the federal government may have certain rights to this invention.

FIELD OF INVENTION

The present invention is directed to treatments and diagnoses for mammalian tumors. More particularly this invention is directed to methods of preventing, treating, treating, and diagnosing mammalian cancer tumors using antibodies having specificity for activated cell surface receptors.

BACKGROUND OF THE INVENTION

Monoclonal antibodies (mAbs) and fragments from them have been used clinically for the diagnosis and treatment of many different human diseases (Dougall et al 1994, Oncogene 2109-23). The anti-tumor efficacy of mAbs not only requires specificity towards tumor antigens which show enhanced expression in neoplastic tissue, but also must demonstrate the desired biological effect, namely, the inhibition of tumor growth.

U.S. Pat. No. 4,522,918 (Schlom et al.) discloses a cancer treatment using monoclonal antibodies directed at surface antigens of human mammary adenocarcinoma cells.

Capone et al., JNCI 72: 673-677, (1984), investigated the relationship between antigen density and immunotherapeutic response elicited by monoclonal antibodies against solid tumors. These investigators used monoclonal antibodies specific against human breast cancer. It was found that passively administered monoclonal antibody can be effective in producing a tumor regression response against solid tumors. Tumoricidal response with monoclonal antibody appeared to be exponentially related to the density of the antigen on the cells.

Members of the c-erbB (erbB) family of receptor tyrosine kinase genes, including epidermal growth factor receptor c-erbB1 (EGFr, HER1), c-erbB2 (HER2, neu, p185), c-crbB-3 (HER3), and c-erbB-4 (HER4), are known to be oncogenes that encode cell surface receptor proteins. The receptors, under some circumstances, display abnormal kinase activities that contribute to cell proliferation and transformation.

ErbB family receptor tyrosine kinases (RTKs) form homodimeric, heterodimeric, or oligomeric complexes that are catalytically active and, thereby, couple extracellular signals with alterations of cellular growth and differentiation status. Their ligands and subsequent receptor-mediated signaling have been implicated in survival, proliferation and differentiation in a variety of cell types (reviewed in Dougall et al. 1994; O'Rourke, et al. 1997; Pinkas-Kramarski, et al. 1997; Tzahar and Yarden 1998).

All members of the erbB family share structural features, including an extracellular ligand binding domain that contains four subdomains, including two cysteine-rich subdomains, a single amphipathic transmembrane domain, and an intracellular kinase domain. The kinase domain shows the highest degree of amino acid sequence similarity (about 80%) among members of this family.

Overexpression of erbB receptors has been found in many types of human cancer, raising the possibility that receptor-linked therapies may be useful as cancer management strategies. EGFr (erbB1) is the most extensively studied member in this family. The EGFr gene is amplified and rearranged in many human brain tumors of glial origin and in some cell lines. Ullrich et al, have found the gene for the EGFr cellular analogue of the avian vital oncogene v-erb-B. (Ullrich et al, Nature, Vol. 309, pp. 418-425, 1984). The epidermal growth factor receptor (EGFr) is a transmembrane glycoprotein of about 170 kDa (Cohen, J. Biol. Chem., Vol. 258, pp. 1523-1531, 1982). Overexpression of the EGFr has been found in a variety of tumors, including bladder, esophagus, lung, glioblastoma and breast. In breast cancers, over 40% of the tumors are EGFr positive, and EGFr levels negatively correlate with steroid receptor (estrogen receptor and progesterone receptor) levels. The EGF-receptor exists in two kinetic forms (low affinity and high-affinity receptors) that may be interconvertible. (Fernandez-Pol, Biol. Chem., Vol. 260, pp 5003-5011, 1985.) Expression of EGF-receptors has been implicated in the progression of tumor growth. In addition, an association has been detected between late stages of melanoma development and extra copies of the chromosome carrying the EGFr gene. (Koprowski et al., Somatic Cell and Molecular Genetics, Vol. 11, pp. 297-302, 1985.)

A variety of strategies have also been developed for targeting the erbB1 receptor including monoclonal antibodies, ligand-linked immunotoxins, tyrosine kinase inhibitors, and antisense approaches (reviewed by Zhang et al., Drug News Perspect, Vol 13, pp 325-329, 2000.).

Of all the members of the erbB family, erbB2 is the most highly correlated to breast cancer, ovarian cancer and pancreatic cancer. Initially identified in rat neuroglioblastomas induced by a carcinogen ethylnitrosourea, neu (also known as her2/erbB2) is a proto-oncogene encoding a 185 kDa receptor-tyrosine-kinase that is highly homologous with, but distinct from, EGFr. The translation product of the erbB-2 oncogene is p185, a transmembrane glycoprotein having tyrosine kinase activity and a molecular weight of about 185,000 daltons, as determined by gel-electrophoresis. Experiments have shown that p185 forms homodimers or heterodimers with epidermal growth factor receptor EGFR (erbB1). The homo- and heterodimers exhibit elevated tyrosine kinase activity that brings about the transformed phenotype in cells having such dimers.

Amplification of the erbB2 gene, the human homologue of neu, and subsequent overexpression of the polypeptide product p185, has been identified in 25-30% of primary breast and ovarian cancers. No oncogenic point mutation has been detected, however, in erbB2 associated with human carcinomas. In the murine fibroblasts NIH3T3 and NR6, overexpression of erbB2 results in transformation, indicating that mutation is not necessary for erbB2 oncogenic potential. Previous work has shown that overexpression of erbB2/neu can lead to oligomers which have enhanced kinase activity (Di Fiore, et al., Science, Vol. 237, pp178-182,-1987).

Overexpression of the erbB2 gene in human breast cancer is associated with a poor prognosis and resistance to hormonal treatment and chemotherapy. Advanced stages of malignancy, characterized by large tumor size, increased number of positive lymph nodes, reduced survival time and decreased time to relapse, was directly correlated with an increased level of amplification of the neu gene. The neu protooncogene is expressed at low levels in normal human tissues.

c-erbB3 is expressed in a variety of normal tissues of epithelial origin and is overexpressed in a subset of human mammary tumors. c-erbB4 (erbB3) is most predominantly expressed in several breast carcinoma cell lines and also in normal skeletal muscle, heart, pituitary, and cerebellum. The erbB3 receptor has only limited kinase activity. Overexpression of the erbB3 or erbB4 gene alone cannot transform NIH3T3 cells, even in the presence of ligand. It is suggested that the contribution of erbB3 and erbB4 to tumorigenicity depends on their heterodimerization with the EGFr or erbB2.

U.S. Pat. No. 6,252,050 describes methods for generating cross-reactive antibodies. Antibodies against p185 and methods of using such antibodies are described in U.S. Pat. Nos. 6,417,168, 6,165,464, 5,772,997, 5,770,195, 5,725,856, 5,720,954, and 5,677,171, which are incorporated herein by reference. U.S. Pat. No. 5,705,157 describes antibodies against EGFR. U.S. Pat. No. 5,470,571 discloses a cancer treatment using monoclonal antibodies directed at the EGFr generated from the A431 carcinoma cell line. Each of the aforementioned U.S. Patents is hereby incorporated herein by reference in its entirety.

Combinations of several antibodies recognizing different epitopes of p185 showed increased efficiency in tumor growth inhibition. Anti-EGFr and anti-p185 antibodies were also used on tumor cells simultaneously to explore possible synergy for clinical treatment. (Wada et al, Oncogene 489, 1990).

Ligand-induced structural changes play an important role in the heterodimerization of erbB-family receptors. Although each erbB receptor may have slightly different sequences of loops at the surface, they share high homology at the framework, or backbone level. The backbone structure is actually critical for the ligand-induced structural changes. Based on this information, an antibody against the structural backbone of the receptors may be a better molecule for therapeutic and/or diagnosis purposes to target the receptors. This type of antibody will recognize several members of this family of receptors, especially the active forms that are directly linked to cell proliferation. The striking similarity between the extracellular domain of receptors of the erbB family suggests that the structural conformation of these receptors may be the most important factor regarding both the ligand-receptor binding and receptor-receptor dimerization.

In the case of receptor-dimerization, a construct containing the extracellular domain plus the transmembrane domain of p185 was able to initiate the p185-EGFr dimerization (Qian et al, PNAS 91, 1500, 1994). Later, an alternative transcript product of p185 with only subdomain I and II was found to be able to dimerize with p185 (Doherty et al. PNAS 1999, 96, 10869) and inhibit its activity.

An approach for disabling receptor activity is to target protein-protein interactions involved in receptor functioning. Since protein-protein interactions play a key role in various mechanisms of cellular growth and differentiation, and viral replication, inhibition of these interactions is a promising novel approach for rational drug design against a wide number of cellular and viral targets (Zutshi et al., *Curr Opin Chem Biol* 1998, 2, 62-66; Peczuh et al., *Chem. Rev.* 2000, 100, 2479-2494). Binding of polypeptide hormones, growth factors or cytokines to cell-surface receptors activates dimerization (oligomerization) of the receptors which leads to the signal transduction to the interior of the cell (Heldin, *Cell* 1995, 80, 213-223). While most of the receptor inhibitors developed to date have been focused on the blockade of receptor-ligand or enzyme-substrate interactions, repression of receptor-receptor interactions that accompany oligomerization also represent an important target for disabling receptor functioning.

Although ligand-induced homo- and heterodimerization of the full-length native erbB receptors has been established and well documented, experimental data on self-associations of the extracellular domains of these receptors is somewhat contradictory. In analytical ultra centrifugation and MALLS studies, ligand-induced homodimerization has been demonstrated for erbB1 and erbB4 (Ferguson et al., EMBO J 2000, 19, 4632-4643). However, no homo-oligomerization could be observed for the erbB3 receptor and the only erbB receptor combinations that produced heterodimers in the presence of HRGβ1 were erbB2/erbB4 and to a smaller extent erbB2/erbB3. In contrast, both erbB3 homodimerization and erbB3/erbB2 heterodimerization have been reported for the ectodomains, but these effects could only be observed when ectodomains of the receptors were anchored to the membrane (Tzahar et al., EMBO J 1997, 16, 4938-4950). Landgraf and Eisenberg have reported ligand-independent self-association of erbB3 ectodomains that could be disrupted by HRGβ1 (Landgraf et al., Biochemistry 2000, 39, 8503-8511). Both monomeric and oligomeric forms of erbB3 were detected in the presence of HRGβ1 by size-exclusion chromatography. Addition of the ligand produced a shift toward a low-molecular mass species.

The present inventors have identified distinct extracellular subdomains of erbB2 that are involved in heterodimerization with erbB1 (Kumagai et al, Proc Natl Acad Sci USA 2001, 98, 5526-5531). Peptidomimetics against subdomain IV alter the heteromeric signaling and transforming activities induced by EGF after associating with EGFR. Peptidomimetics and antibodies that target subdomain IV are therefore as therapeutic agents against erbB-expressing tumors.

SUMMARY OF THE INVENTION

The present invention relates to antibodies having specificity for activated cell surface receptor proteins. In certain embodiments, the specificity for activated receptors is due to antibody recognition of an activation epitope that is created upon assembly of proteins into higher order protein complexes. In a preferred embodiment, the specificity of the antibody is not due, either in whole or in part, to the presence of a phosphotyrosine residue on the activated cell surface receptor. Also preferred is where the antibody does not bind to an intracellular domain of the cell surface receptor, e.g., the antibody binds to an extracellular domain of the receptor. Most preferred is where the antibody has the characteristics of binding to an epitope that does not comprise a phoshpotyrosine residue and which is in an extracellular region of the protein.

Also preferred is where antibody specificity is due to antibody recognition of an epitope that is formed upon assembly of protein monomers into, e.g., dimers, trimers or higher oligomeric complexes. The antibodies may have specificity for activation epitopes formed upon formation of, for example, activated erbB receptors, TNF receptors and immunoglobulin gene superfamily (IgSF) receptors (e.g, B7, B7RP-1, CD28, and ICOS). In a preferred embodiment, the antibodies recognize activation epitopes formed upon erbB receptor activation.

In certain embodiments, the invention relates to cross-reactive "dual-specificity" antibodies that bind to an activation epitope formed from two or more distinct proteins. The cross-reactive dual-specificity antibodies can bind, for example and without limitation, to heterodimeric or oligomeric erbB receptors or heterooligomeric TNF receptors, or heteromeric complexes comprising members of the immunoglobulin gene superfamily (IgSF), which includes but is not limited to B7, B7RP-1, CD28, and ICOS. In another embodiment, the invention provides cross-reactive dual-specificity antibodies that bind to an epitope shared by heterodimers of erbB receptors, to an epitope shared by heterodimers of TNF receptors, or to an epitope shared by heterodimers of the immunoglobulin gene superfamily (IgSF). The epitope can comprise contiguous or noncontiguous amino acid sequences.

In certain embodiments, the invention provides antibodies that bind to assembly epitopes of cell surface receptors. In certain preferred embodiments antibodies bind to assembly epitopes of activated homodimeric complexes of erbB1, erbB2, erbB3 or erbB4. Also preferred are embodiments wherein antibodies bind to assembly epitopes of activated heterodimeric complexes of erbB1 and erbB2 erbB1 and erbB3, erbB1 and erbB4, erbB2 and erbB3, erbB2 and erbB4, erbB3 and erbB4, or assembly epitopes of activated complexes comprising at least one TNF family receptor.

In still further embodiments, the invention provides a monoclonal antibody produced by hybridoma cell lines designated 8A4, A10A12, 9G6, 7H4, A10E9, A12D6, A6B12, A10E11, B3G4, A5C7, 13A11, 11C11 and 13B11. In a preferred embodiment, a monoclonal antibody is produced by the hybridoma cell 8A4 or A10A12. In further embodiments, the invention provides an antibody with a variable region or a complementarity determining region of one of the foregoing monoclonal antibodies. Also, preferred is where the invention provides a humanized antibody with a variable region or a complementarity determining region of one of the foregoing monoclonal antibodies In still further embodiments the present invention provides antibodies which disable the oligomerization of receptors. In a preferred embodiment, antibodies are induced by immunizing with a peptide or protein subdomain containing shared structural elements involved in the oligomerization. In certain embodiments, the structural element is a cystine knot.

In a preferred embodiment, the invention provides antibodies that bind to subdomains of activated erbB1, erbB2, erbB3, erbB4, the TNF family of receptors, or members of the IgSF, or assemblies thereof, that contain cystine knots. Accordingly, in some embodiments the invention provides antibodies that bind to cystine knots of erbB1, erbB2, erbB3, and erbB4, or to cystine knots of TNF receptors.

The invention also provides compositions comprising any of the aforementioned antibodies specific for activated cell surface receptors, e.g., dual-specificity antibodies, including, for example and without limitation, those which bind to erbB receptors or to the TNF family of receptors. In a preferred embodiment the invention provides injectable pharmaceuticals that are sterile and pyrogen free.

Also provided are antibodies that bind to interaction surfaces in the extracellular domains of activated erbB receptors or to interaction surfaces in the extracellular domains of activated TNF receptors.

Some embodiments of the present invention relate to pharmaceutical compositions comprising antibodies specific for activated cell surface receptors, including, e.g., dual-specificity monoclonal antibodies, which bind to homo- or heterodimers of erbB receptors or homo- or heterooligomers of TNF receptors, in combination with anti-cancer drugs. Some of such pharmaceutical compositions are injectable pharmaceuticals which are sterile and pyrogen free.

Certain embodiments of the present invention relate to antibodies recognizing peptides that mimic erbB receptors or TNF receptors. In preferred embodiments, antibodies recognize a peptide that mimics an extracellular domain of an erbB receptor or of an extracellular domain of a TNF receptor. Further preferred are embodiments wherein an antibody recognizes a peptide that mimics subdomain IV of the erbB receptor. More preferred are embodiments wherein an antibody recognizes a peptide that mimics the S22 or S23 loop of the erbB receptor.

Certain embodiments of the present invention relate to antibodies recognizing mimetics of erbB receptors or TNF receptors. In some embodiments, antibodies recognize a mimetic of an extracellular domain of an erbB receptor or of an extracellular domain of a TNF receptor. In more preferred embodiments, antibodies recognize a mimetic of subdomain IV of the erbB receptor. In even more preferred embodiments, antibodies recognize a mimetic of the S22 or S23 loop of the erbB receptor.

Certain embodiments of the present invention relate to pharmaceutical compositions comprising antibodies to peptides or mimetics of erbB receptors or TNF receptors, in combination with anti-cancer drugs. Some such embodiments are injectable pharmaceuticals which are sterile and pyrogen free.

Certain embodiments of the present invention relate to methods of treating human patients having solid tumors by administering to the patient antibodies specific for activated cell surface receptors, including, e.g., dual-specificity monoclonal antibodies, which bind to homo- or heterodimers of erbB receptors or homo- or heterooligomers of TNF receptors. In a preferred embodiment, the antibodies are specific for activated erbB proteins. Further preferred are where the antibodies are dual-specificity anti-erbB antibodies having specificity for an activation epitope formed upon formation of activated erbB heterodimers. In some embodiments of the present invention, the administration of antibodies may optionally be followed by exposing the patient to a therapeutically effective amount of anti-cancer radiation. In certain embodiments, the administration of antibodies is performed in combination with administration of a therapeutically effective amount of a chemotherapeutic agent. In certain embodiments the administration of antibodies is performed in combination with administration of a therapeutically effective amount of a chemotherapeutic agent and followed by exposing the patient to a therapeutically effective amount of anti-cancer radiation.

In other embodiments, the invention relate provides methods of treating patients (e.g., human patients) having solid tumors by administering to the patient antibodies to activated erbB receptors that have been obtained using peptides or mimetics of erbb receptors as antigens. In some such embodiments the administration of the antibodies to activated erbB receptors may optionally be followed by exposing the patient to a therapeutically effective amount of anti-cancer radiation. In other embodiments, the administration of antibodies to activated erbB receptors is performed in combination with administration of a therapeutically effective amount of a chemotherapeutic agent. In some embodiments the administration of antibodies to activated erbb receptors is performed in combination with administration of a therapeutically effective amount of a chemotherapeutic agent and followed by exposing the patient to a therapeutically effective amount of anti-cancer radiation.

Certain embodiments of the present invention relate to methods of treating human patients having solid tumors by administering to the patient antibodies to activated erbB receptors, e.g., dual-specificity anti-erbB antibodies, that are conjugated to radioactive or chemotherapeutic agents.

Certain embodiments of the present invention relate to methods for generating cross-reactive dual-specificity monoclonal antibodies to members of multigene families such as, for example and without limitation, the erbB receptor family, the TNF receptor family, or the immunoglobulin gene superfamily. Cross-reactive dual-specificity antibodies are generated by priming animals, preferably rodents, with one member of the family and boosting with at least one closely related member of the family.

Further embodiments of the present invention relate to methods of treating human patients having solid tumors by administering to a patient antibodies to activated erbB receptors obtained using peptides or mimetics of erbb receptors as antigens, wherein the antibodies are conjugated to radioactive, chemotherapeutic, or photodynamic therapeutic agents.

Still further embodiments of the present invention relate to pharmaceutical compositions comprising antibodies to activated receptors, e.g., dual-specificity monoclonal antibodies which bind to erbB or TNF receptors that are conjugated to radioactive or chemotherapeutic agents. Some embodiments relate to injectable pharmaceuticals which are sterile and pyrogen free.

Certain embodiments of the present invention relate to methods of preventing tumors in human patients by administering to the patient an antibody to activated receptors, e.g., an dual-specificity anti-erbB antibody.

Certain embodiments of the present invention relate to methods of preventing tumors in human patients by administering to the patient at least one peptide or mimetic of erbB receptors, thereby inducing formation of antibody to activated erbB receptors, e.g., dual-specificity erbB antibody Certain embodiments of the present invention relate to methods of imaging erbB tumors in human patients having such tumors using detectable antibody to activated erbB receptor, e.g., a dual-specificity anti-erbB antibody.

Certain embodiments of the present invention relate to pharmaceutical compositions comprising a detectable antibody to activated receptors, e.g, dual-specificity monoclonal antibody, specific to activated erbB, TNF, or IgSF receptors. Some embodiments relate to injectable pharmaceuticals which are sterile and pyrogen free.

Certain embodiments of the present invention relate to diagnostic kits and to methods for imaging and/or detecting solid tumors using antibody to activated erbB receptors, e.g., dual-specificity anti-erbB antibodies.

Certain embodiments of the present invention relate to methods of altering the specificity of antibodies. Mono-specific antibodies, for example, are made dual-specific by altering the coding sequences of the complementarity-determining region (CDR).

BRIEF DESCRIPTION OF THE DRAWINGS

FIG. 3 depicts tumor size after treatment with different antibodies or with vehicle.

DETAILED DESCRIPTION OF THE INVENTION

Figure 1A:
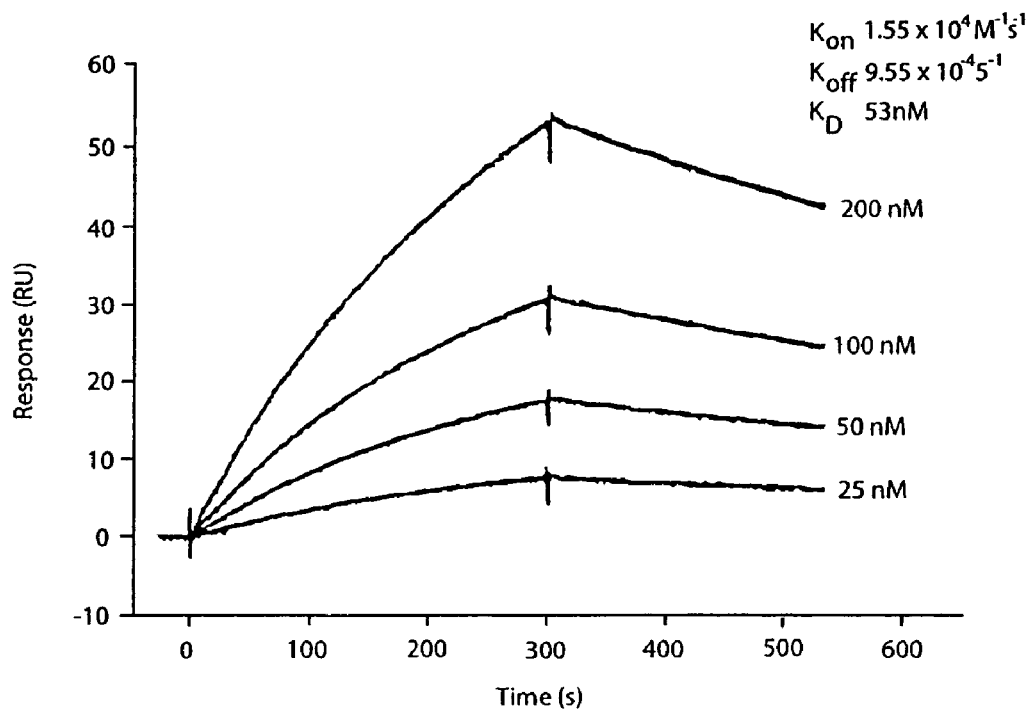
FIG. 1A-B depicts surface plasmon resonance (Biacore) analysis of the interaction between the HER2 receptor ectodomain and 8A4 Mab (A) and the effect of EGF on binding of EGFR to 8A4(B).

The present invention provides compositions comprising antibodies specific for activated cell surface receptors and methods of use thereof. The specificity of the antibodies is due to their recognition and binding of activation epitopes that are formed upon assembly of cell surface receptor proteins into higher order protein complexes that accompanies receptor activation. The antibodies and compositions thereof are useful for the diagnosis, imaging, and treatment of mammalian tumors.

Antibodies with specificity for activated cell surface receptors that have been described in the prior recognize epitopes comprising phosphotyrosine residues that are present on an intracellular domain or region of the receptor. Due to their intracellular location, however, phosphotyrosine-containing epitopes are not accessible to bind extracellular antibodies, when the antibodies are administered to intact cells. The inaccessibility of the phosphotyrosine-containing epitopes makes antibodies that recognize or are specific for the epitope unsuitable for the diagnosis, imaging, and treatment of mammalian tumors.

Cell surface receptors associated with and expressed in mammalian tumors are also typically found as well on the surface of both normal and tumor cells. When present on the surface of normal cells, the cell surface receptors are typically present in lower amounts or in a state such that their presence does not lead to a transformed cell phenotype or formation of a tumor. The large number of normal cells in the mammalian body, relative to the number of tumor cells, however, provides a large of pool of unactivated receptor, relative to active receptor present on the surface of transformed and/or tumor cells. Hence, treatment of mammalian tumors with antibodies that are not specific for activated cell surface receptors requires increased amounts of antibody sufficient to bind to both normal cells and tumor cells. The specificity of the antibodies for activated cell surface receptors provides for specific binding of the antibodies to tumor or transformed cells bearing activated receptors, e.g., cells that overexpress a cell that express a mutant activated form of a cell surface receptor, thus allowing for treatment of tumors with reduced amounts of an antibody specific for activated cell surface receptor, relative to the amounts of antibody that are required for tumor treatment when the antibody is not specific for activated cell surface receptor. Accordingly, the antibodies specific for activated cell surface receptors that are provided by the present invention have the benefit of allowing treatment of tumors with reduced amount of antibody and therefore at a lower cost and without the undue side effects that are associated with anti-tumor treatments using antibodies known in the prior art that require administration of relatively higer amounts of antibody.

In a preferred embodiment, the invention provides antibodies that bind to and are specific for an epitope of an activated cell surface receptor that is on an extracellular region of the receptor. In an independent preferred embodiment, the invention provides antibodies that bind to and are specific for an epitope of an activated cell surface receptor wherein the epitope does not a comprise a phosphotyrosine residue. Also preferred is an embodiment where the invention provides antibodies wherein, simultaneously, the antibodies bind to and are specific for an epitope of an activated cell surface receptor that is on an extracellular region of the receptor and the epitope does not comprise a phosphotyrosine residue.

In preferred embodiments, compositions comprising dual-specificity antibodies are provided that have specificity for at least one assembly epitope formed upon oligomerization of two monomers. In an especially preferred embodiment, an epitope comprises one or more cystine knots. The present invention further provides methods for treatment, diagnosis, and imaging of mammalian tumors using dual-specificity antibodies.

In certain embodiments, compositions comprising antibodies to peptides and mimetics of regions of receptors which facilitate oligomerization are provided, preferably directed to regions of receptors comprising one or more cystine knots. The present invention further provides methods for treatment, diagnosis, and imaging of mammalian tumors using such peptide mimetics. In other embodiments, the invention provides antibodies against such peptide mimetics. The antibodies are preferably dual-specificity antibodies.

Definitions

As used herein, the term "erbB" refers to receptors in the erbB family of receptor tyrosine kinases which assemble into hetero- or homodimers, including, but not limited to, erbB1 (EGFr—epidermal growth factor receptor, HER1), erbB2 (neu, p185, HER2), erbB3 (HER3), and erbB4 (HER4).

As used herein, the term "TNF" refers to receptors that bind tumor necrosis-like factors and which assemble into oligomers. TNF receptors include, but are not limited to, TNF, FAS, RANK, TRAIL, and CD40.

As used herein, the terms "p185/EGFr cancer", "p185/EGFr tumors", "erbB2/EGFr cancer" and "erbB2/EGFr tumors" are meant to refer to tumor cells and neoplasms which express erbB2 and EGFr. erbB2/EGFr tumors have p185 and EGF receptors on their cell surfaces.

As used herein, the terms "erbB tumor", and "erbB cancer" are meant to refer to tumor cells and neoplasms that express one or more erbB receptors. Some erbB tumor cells or neoplasms may express p185 receptors on their cell surfaces.

As used herein, the terms "TNF", and "TNF-related pathologies" are meant to refer to pathologies that involve one or more TNF family receptors.

As used herein, the term "oligomerization" refers to the process by which monomers are formed into dimers or higher order multimeric complexes. Examples of assemblies formed through this process include but are not limited to dimers, trimers and tetramers, etc. Such assemblies may comprise two or more identical monomers yielding a homodimer, homotrimer, homotetramer, etc., or two or more different monomers yielding a heterodimer, heterodimer, heterotrimer, etc.

As used herein an "activated receptor" is a receptor that is capable of generating an intracellular signaling event or which is characterized by increased signaling activity relative to receptor that is not activated. Activated receptor tyrosine kinases (RTKs), for example, exhibit elevated levels of tyrosine kinase activity compared to RTKs that are not activated. Cellular events that lead to activation of receptors are well known among those of ordinary skill in the art. Activation typically includes oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Events leading to formation of activated cell surface receptor complexes are well known to those of ordinary skill in the art. Complex formation may be caused by, for example, overexpression of normal or mutant forms of receptor on the surface of a cell. Complex formation may also be caused by a specific mutation or mutations in a receptor.

As used herein, the term "activation-epitope" is an epitope that is formed or created upon activation of cell surface receptor that is not present or not accessible in a non-activated receptor. The terms "formed upon" or "created upon" can denote that the activation epitope is an "assembly epitope" that comprises at least one amino acid from each of at least two proteins in a protein complex. Accordingly, the epitope is formed upon complex formation and is not present in proteins prior to complex formation, e.g., without limitation, in monomers. Such epitopes are typically found at protein interfaces that are formed during complex formation. Alternatively, "formed upon" or "created upon" can denote an activation epitope comprising amino acids from a single protein, i.e., a single polypeptide chain, but which is not recognized or accessible to antibody prior to complex formation. Such epitopes may be formed as the result of, for example, conformational changes that occur in a receptor protein upon complex formation, which lead to the formation of the epitope or lead to increased accessibility of the epitope to antibody binding.

As used herein, the terms "dual-specific," "dual-specificity" and "cross-reactive", used along or in combination with other terms, are used synonymously to refer to a composition which binds to two or more binding partners. For example, an antibody which cross-reacts with two or more different antigens is capable of binding to each of the different antigens.

As used herein, the term "dual-specificity monoclonal antibodies which bind to erbB receptors" refers to monoclonal antibodies which bind to an epitope shared by two erbB receptors.

As used herein, the term "dual-specificity monoclonal antibodies which bind to TNF receptors" refers to monoclonal antibodies which bind to an epitope shared by two TNF receptors.

As used herein, the term "dual-specificity monoclonal antibodies which bind to IgSF receptors" refers to monoclonal antibodies which bind to an epitope shared by two IgSF receptors.

As used herein, the term "antibody" is meant to refer to antibodies, as well as antibody fragments such as FAb and $F(Ab)_2$ fragments, recombinant antibodies or recombinant antibody fragments. Antibodies may, in some preferred embodiments, be monoclonal, humanized, primatized, camelized phage-displayed or chimeric antibodies.

As used herein, the term "cystine knot" refers to a polypeptide formed by at least two disulfide bonds and the protein chains linking them, penetrated by a third disulfide bond and is further described in Murzin et al., J. Mol. Biol. 247: 536-540, which is incorporated by reference in its entirety. For example, in the TNF receptor family a cystine knot consists of 42 amino acid residues with 6 cysteine residues forming 3 inter-chain disulfide bonds to create the structural motif.

As used herein, the phrase "cystine knot specific antibody" refers to an antibody which binds to a cysteine-rich domain, a cystine knot, or a portion of a cystine knot loop. In a preferred embodiment, a cystine knot specific antibody binds a cystine knot comprising region erbB subdomain IV. Further preferred is where the cystine knot comprising region is selected from the group consisting of the S22 loop and the S23 loop.

As used herein, the phrase "cystine knot comprising region" refers to a portion of a receptor that comprises one or more cystine knots. In some embodiments, the cystine knot-comprising region is an extracellular portion of the receptor. In some preferred embodiments, the cystine knot comprising region is subdomain IV. In more preferred embodiments, the cystine knot comprising region is selected from the group consisting of the S22 loop and the S23 loop.

As used herein, the term "region" refers to a part of a receptor comprising at least one portion. Representative receptor regions include, but are not limited to, extracellular regions, transmembrane regions, and intracellular regions.

As used herein, the term "portion" refers to at least 3-5 amino acids, more preferably at least 8-10 amino acids, more preferably at least 11-15 amino acids, more preferably at least 17-24 amino acids, and even more preferably at least 25-30 amino acids, and most preferably at least 30-45 amino acids.

As used herein, the term "conformation site" refers to a site on a receptor which affects the conformation of the receptor. In some embodiments, binding of an antibody, peptide or mimetic to the conformation site changes the conformation of the receptor such that oligomerization of the receptor is prevented and, preferably, reduces or eliminates receptor signaling. In some preferred embodiments, the conformation site is a receptor-receptor contact point.

As used herein, the term "mimetic" is used to refer to compounds which mimic the activity of a peptide. Mimetics are non-peptides but may comprise amino acids linked by non-peptide bonds. U.S. Pat. No. 5,637,677 and its parent applications contain detailed guidance on the production of mimetics. Briefly, the three dimensional structure of the peptides which specifically interacts with the three dimensional structure of erbB receptors is duplicated by a molecule that is not a peptide. Examples of mimetics are also found in U.S. patent application Ser. No. 10/119,288, filed Apr. 8, 2002.

As used herein, the terms "conformationally restricted peptides", "constrained peptides" and "conformationally constrained peptides" are used interchangeably and are meant to refer to peptides which, for example through intramolecular bonds, are conformationally stable and remain in a sufficiently restricted conformation. The compounds have an affinity to erbB receptors and, when bound to erbB receptors on cells, have a biologically active effect on cells that have a erbB-mediated transformation phenotype.

As used herein, the terms "aromatic amino acids" and "aromatic amino acid residues" used interchangeably are meant to refer to phenylalanine and tyrosine.

As used herein, the term "exocyclic amino acid residue" is meant to refer to amino acid residues which are linked to cyclicized peptide but which are not within the portion of the peptide that makes up the circularized structure.

As used herein, the term "exocyclic portions" is meant to refer to amino acid sequences having one or more amino acid residues which are linked to cyclicized peptide but which are not within the portion of the peptide that makes up the circularized structure.

As used herein, the term "linking moiety" is meant to refer to a molecular component or functional group which is capable of forming bonds with three amino acids.

As used herein, the term "linking amino acid residue" is meant to refer to an amino acid residue that is a linking moiety.

As used herein, the terms "active sequence" and "active region" are used interchangeably and are meant to refer to the amino acid sequence of the portion of a compound of the invention that directly interacts with an erbB receptor, wherein the interaction is characterized by an affinity between the active portion and an erbb receptor.

In some embodiments, the peptides and mimetics are constrained mimics of the loops or repeats present in subdomain IV of erbB receptors. In some embodiments, the peptides and mimetics mimic a cystine knot comprising region, preferably a cystine knot or portion thereof. In some embodiments, binding of a peptide or mimetic to an erbB or TNF receptor prevents dimerization of the receptor, and, preferably, reduces or eliminates receptor signaling.

As used herein, the term "dimerization site" is used interchangeably with the terms "interaction site" and "interaction surface" and refers to a site on a receptor that forms a bond with another receptor when the two receptors dimerize. In some embodiments, the dimerization site is ligand-independent, i.e., the dimerization site is not dependent on the presence or absence of a particular bound ligand. In other embodiments, the dimerization site is ligand-dependent, i.e., the dimerization site is dependent on the presence or absence of a particular bound ligand. In some embodiments, binding of an antibody, peptide or mimetic to the dimerization site prevents dimerization of the receptors and, preferably, reduces or eliminates receptor signaling. In some preferred embodiments, the dimerization site is subdomain IV of the erbB receptor or a portion thereof.

As used herein, the term "assembly" is used interchangeably with "ensemble" or "dimer" and refers to homo- or heterooligomers of receptors. Such assemblies may comprise erbB1, erbB2, erbB3, erbB4, or combinations thereof, or receptors in the TNF family of receptors, including but not limited to FAS, RANK, TRAIL, and CD40, or combinations thereof, or members of the IgSF superfamily, including but not limited to ICOS and CD28.

As used herein, the term "high risk individual" is meant to refer to an individual who has had an erbB or TNF related pathology or pathologies associated with IgSF members either removed or in remission, and who is therefore susceptible to a relapse or recurrence. In the case of erbB, as part of a treatment regimen for a high risk individual, the individual can be prophylactically treated against tumors that they have been diagnosed as having had in order to combat a recurrence. Thus, once it is known that an individual has had an erbB-cancer, the individual can be treated according to the present invention to prevent normal cells from transforming into tumor cells.

As used herein, the term "transformation" refers to the process by which a cell goes from a non-cancerous, non-tumorigenic state to a state wherein the cell has the properties of cancerous cells and is competent to form tumors. The cellular events typically associated with cell transformation are will known among those of ordinary skill in the art and may include, for example, mutations, genomic rearrangements or a change in expression pattern of a specific gene or gene product, or sets of genes or gene products. Transformation may be caused by overexpression of cell surface proteins, e.g., erbB, TNF and IgSF family members.

Cells may exist in "partially transformed" or "fully transformed" states. "Fully transformed" cells are those cells exhibiting properties of highly cancerous cells, i.e., cells with high tumor-forming potential or cells that are less responsive to anti-cancer and anti-tumor treatments. "Partially transformed" cells are those cells exhibiting some physical or phenotypic characteristic of transformed cells, but which have lower tumor-forming potential or are potentially more responsive to anti-cancer or anti-tumor treatments. The cellular markers or phenotypic characteristics that can be used to distinguish "partially transformed" cells from "fully transformed" cells are well known to those of ordinary skill in the art, e.g., immunological, morphological and cytochemical markers and gene expression profiles (LeBien, T. W., et al., (1981) *Cancer Res.*, 41:4776-4780 and Zajchowski, D. A., et al., (2001) *Cancer Res.*, 61:5168-5178).

As used herein, the term "in combination with" is meant to refer to administration of an antibody, peptide or mimetic composition of the invention with each other or with radiation therapy and/or chemotherapy. Administration of the antibody, peptide or mimetic compositions may take place prior to, simultaneously with, or after radiation therapy and/or chemotherapy.

As used herein, the term "therapeutically effective amount" is meant to refer to an amount of an antibody, peptide or mimetic which produces a medicinal effect observed as reduction or reverse in tumorigenic phenotype of tumor cells in an individual when a therapeutically effective amount of a antibody is administered to the individual. Therapeutically effective amounts are typically determined by the effect they have compared to the effect observed when a composition which includes no active ingredient is administered to a similarly situated individual.

As used herein, the term "preventing the development of tumors" is meant to refer to preventing the transformation of normal cells into tumor cells including inhibiting the transformation of cells that have a normal or incomplete transformed phenotype into fully transformed phenotype. Thus, the development of tumors refers to the transformation event which results in the acquisition of a transformed phenotype. According to some aspects of the present invention, antibodies, peptides or mimetics may be administered to individuals who are at risk of developing tumors. The prophylactic administration of an antibody, peptide or mimetics to high-risk individuals results in preventing occurance of a transformation event. Cells having the normal phenotype are not converted to the cells having transformed phenotype. The antibodies, peptides, or mimetics prevent tumors before they are formed by preventing a normal cell from becoming a cancer cell.

As used herein, the term "prophylactically effective amount" is meant to refer to an amount of an antibody, peptide, or mimetic which produces a medicinal effect observed as the prevention of non-transformed cells from becoming transformed in an individual when a prophylactically effective amount of an antibody, peptide or mimetic is administered to an individual. Prophylactically effective amounts are typically determined by the effect they have compared to the effect observed when a composition which includes no active ingredient is administered to a similarly situated individual.

As used herein, the phrase "injectable pharmaceutical composition", or variants thereof, refers to pharmaceutical compositions which satisfy the USP requirements for "injectables", i.e., sterile, pyrogen- and particulate free, and possessing specific pH and isotonicity values.

Antibodies

The present invention describes, inter alia, the biochemical consequences of antibodies that are capable of disabling the assembly of erbB receptor polypeptides or altering TNF receptor polypeptides by different mechanisms. Antibodies may be single receptor specific, dual receptor specific, cystine knot comprising region specific, cystine knot specific, or cystine knot portion specific.

Antibodies that recognize and bind specifically to activated cell surface receptors, e.g., receptor tyrosine kinases, are useful to prevent oligomerization-mediated signaling of receptors and thereby down modulate activity, e.g., kinase activity, of the receptors. When bound, the antibodies disable or eliminate or reduce activity that results in an elimination or reduction in cell proliferation levels and a non-transformed, quiescent phenotype. The antibodies are therefore useful in the treatment of individuals suspected of having erbB tumors and in the prevention of such tumor formation. The cells in the individuals that would otherwise turn into tumors in an untreated individual do not become transformed and do not become tumors in individuals treated by the methods. When administered to individuals who have been identified as being susceptible to or otherwise at risk of developing tumors, the antibodies bind to, for example, erbB1 and erbB2, thereby preventing the elevation in tyrosine kinase activity associated with dimerization of the receptors. The tyrosine kinase activity in the cell never becomes sufficiently elevated and the cell remains non-transformed.

In a preferred embodiment, antibodies that recognize and bind specifically to activated cell surface receptors are dual-specificity antibodies that bind to both of two receptors, for example and without limitation, to both erbB 1 and erbB2, Antibodies, e.g., preferably dual-specificity monoclonal antibodies, useful in anti-tumor compositions can be produced by those skilled in the art using readily available starting materials and the techniques described herein. General techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which provides detailed guidance for the production of hybridomas and monoclonal antibodies which specifically bind to target proteins.

Monoclonal antibody techniques known in the prior art are modified to produce antibodies specific for activated cell surface receptors, e.g., dual-specificity antibodies. Briefly, as non-limiting example, a first protein of interest, e.g., without limitation, rodent or human erbB2, for example, or cells which express the first protein, are injected into mice. The mouse is then boosted with a second protein of interest, e.g., without limitation, rodent or human erbB1, or cells which express the second protein. The spleen of the mouse is removed and the spleen cells are isolated and fused with immortalized mouse cells. The hybrid cells, i.e., hybridomas, are cultured and those cells which secrete antibodies are selected. The antibodies are analyzed and, if found to specifically bind to the protein of interest, the hybridoma which produces them is cultured to produce a continuous supply of antigen-specific antibodies. Humanized or camelized antibodies may be generated using techniques well-known to those skilled in the art.

In certain embodiments, antibodies specific for one epitope are made dual-reactive by genetically altering the CDR using techniques known to those skilled in the art.

In certain embodiments, antibodies are induced by immunizing an erbB or TNF receptor, or portion thereof. In preferred embodiments, antibodies are induced by immunizing with a cystine knot peptide mimetic or peptide mimetic from cysteine rich domains with or without constraints.

In certain embodiments, an antibody is produced by immunizing a suitable host with a peptide selected from the group consisting of:

Y-C-F-P-D-E-E-G-A-C-Y; (SEQ ID NO:3)

C-K-V-E-L-M-Y-P-P-P-Y-F-V-G-M-G-N-G-T-Q-I-Y-V-I-D-P-E-P-C; (SEQ ID NO:28)

-continued

```
C-K-I-E-F-M-Y-P-P-P-Y-L-D-N-E-R-S-N-G-T-I-I-H-I-K-E-K-H-L-C;     (SEQ ID NO:29)

C-S-L-S-I-F-D-P-P-P-F-Q-E-R-N-L-S-G-G-Y-L-H-I-Y-E-S-Q-L-C;       (SEQ ID NO:30)

B2-S22-APE:   Y-C-P-I-W-K-F-P-D-E-E-C-Y;                         (SEQ ID NO:31)

B1-S22-ALG:   Y-C-L-V-W-K-Y-A-D-A-G-C-Y;                         (SEQ ID NO:32)

B3-S22-APQ:   Y-C-P-I-Y-K-Y-P-D-V-Q-C-Y;                         (SEQ ID NO:33)

B4-S22-AFD:   Y-C-P-I-F-K-Y-A-D-P-D-C-Y;                         (SEQ ID NO:34)

B2-S22-ALFA:  Y-C-F-P-D-E-E-G-A-C-Y.                             (SEQ ID NO:35)
```

In certain preferred embodiments, the antibody is a dual-specificity antibody. In some embodiments the antibody binds to a cystine knot of an erbb receptor.

According to some embodiments of the invention, a monoclonal antibody is provided which has the following properties: (a) binds to human and/or rat erbB1, erbB2, erbB3, or erbB4-receptors, with higher affinity towards active receptors; and (b) binds to human and/or rat erbB1, erbB2, erbB3, or erbB4-receptors, wherein the erbB receptor in (a) is different than the erbB receptor in (b).

Preferably, the binding affinity for erbB antigens is at least $1 \times 10^6$ Ka. Preferably, the binding affinity for the erbB receptor of part (a) is at least $5 \times 10^6$ Ka, more preferably $1 \times 10^7$ Ka, more preferably $2 \times 10^7$ Ka, more preferably $1 \times 10^8$ Ka. Likewise, the binding affinity for the erbB receptor of part (b) is preferably at least $5 \times 10^6$ Ka, more preferably $1 \times 10^7$ Ka, more preferably $2 \times 10^7$ Ka, more preferably $1 \times 10^8$ Ka. In some particularly preferred embodiments, the binding affinity for the erbB receptor of part (a) is at least $5 \times 10^6$ Ka and the binding affinity for the erbB receptor of part (b) is preferably at least $5 \times 10^6$ Ka. More preferably, the binding affinity for the erbB receptor of part (a) is at least $1 \times 10^7$ Ka, and the binding affinity for the erbB receptor of part (b) is preferably at least $1 \times 10^7$ Ka. More preferably, the binding affinity for the erbB receptor of part (a) is at least $2 \times 10^7$ Ka and the binding affinity for the erbB receptor of part (b) is preferably at least $2 \times 10^7$ Ka. More preferably the binding affinity for the erbB receptor of part (a) is at least $1 \times 10^8$ Ka and the binding affinity for the erbB receptor of part (b) is preferably at least $1 \times 10^8$ Ka. In some embodiments, the binding affinity for the erbB receptor of part (a) is at least $2 \times 10^7$ Ka and the binding affinity for the erbB receptor of part (b) is at least $1 \times 10^8$ Ka.

According to preferred embodiments of the invention, a monoclonal antibody is provided which has the following properties: (a) binds to a first human and/or rat TNF-receptor, with higher affinity towards active receptors; and (b) binds to a second human and/or rat TNF-receptor, wherein the TNF receptor in (a) is different than the TNF receptor in (b).

Preferred binding affinities for first and second TNF receptors are as set forth above respectively for first and second erbB receptors.

According to preferred embodiments of the invention, a monoclonal antibody is provided which has the following properties: (a) binds to a first human/rat IgSF family-receptor, with higher affinity towards active receptors; and (b) binds to a second human/rat IgSF family-receptor, wherein the IgSF family-receptor in (a) is different than the IgSF family-receptor in (b).

Preferred binding affinities for first and second IgSF family receptors are as set forth above respectively for first and second erbB receptors.

As used herein, an antibody that is specific for an activated cell surface receptor binds to the activated receptor with a greater affinity than it binds to a cell surface receptor that is not activated. Preferably, an antibody specific for an activated cell surface receptor binds to the activated receptor with an affinity that is at least 5-fold greater than the affinity with which it binds to a cell surface receptor that is not activated. More preferably, an antibody specific for an activated cell surface receptor binds to the activated receptor with an affinity that is at least 10-fold greater than the affinity with which it binds to a cell surface receptor that is not activated. More preferably, an antibody specific for an activated cell surface receptor binds to the activated receptor with an affinity that is at least 20-fold greater than the affinity with which it binds to a cell surface receptor that is not activated. Even more preferably, an antibody specific for an activated cell surface receptor binds to the activated receptor with an affinity that is at least 50-fold greater than the affinity with which it binds to a cell surface receptor that is not activated. Still more preferably, an antibody specific for an activated cell surface receptor binds to the activated receptor with an affinity that is at least 100-fold greater than the affinity with which it binds to a cell surface receptor that is not activated. Most preferably, an antibody specific for an activated cell surface receptor binds to the activated receptor with a detectable, e.g., high, affinity, without significant affinity (e.g., $Kd > 10^{-2}$ M) for a cell surface receptor that is not activated.

The present invention is useful to therapeutically treat an individual identified as suffering from erbB tumors and/or TNF of IgSF pathologies. The present invention is also useful to prophylactically treat an individual who is predisposed to develop erbB tumors or TNF/IgSF-related pathologies or who has had erbB tumors or TNF/IgSF-related pathologies and is therefore susceptible to a relapse or recurrence. The present invention is also useful, inter alia, to image erbB tumors or TNF/IgSF-related pathologies and otherwise detect them.

The antibodies of the invention are also useful in the treatment of erbB tumors or TNF/IgSF-related pathologies either as a component of a composition administered to a patient (i) alone; (ii) in combination with radiation therapy and/or chemotherapy; or (iii) as a component of a composition administered to a patient that comprises the antibody conjugated to a radioactive or chemotherapeutic agent.

The antibodies of the invention are also useful in the prevention of erbB tumors or TNF/IgSF-related pathologies either as a component of a composition administered to a patient (i) alone; (ii) in combination with radiation therapy and/or chemotherapy; or (iii) as a component of a composition administered to a patient that comprises the antibody conjugated to a radioactive or chemotherapeutic agent.

The antibodies of the invention are useful in the imaging of erbB tumors or TNF/IgSF-related pathologies as, for example, a detectable component of a composition administered to a patient.

The antibodies of the invention are also useful in diagnostic kits and in vitro methods of identifying a tumor as an erbB tumor.

In accordance with one preferred embodiment of the invention, the antibody is a dual-specificity antibody that is specific for an epitope formed upon formation of an activated erbB1-erbB2 receptor complex. In another preferred embodiment, a dual-specificity antibody is specific for an epitope formed upon formation of an activated erbB2-erbB4 receptor complex. In another preferred embodiment, a dual-specificity antibody is specific for an epitope formed upon formation of an activated erbB2-erbB3 receptor complex. In another preferred embodiment, a dual-specificity antibody is specific for an epitope formed upon formation of an activated erbB1-erbB3 receptor complex. In a still further preferred embodiment, the dual-specificity antibody is specific for an epitope formed upon formation of an activated erbB1-erbB4 receptor complex.

In accordance with a preferred embodiment of the invention, a dual-specificity antibody is specific for an epitope shared by two TNF family receptors, for example, by TNF and FAS.

In addition to molecules designed from assembly epitopes of erbB2 and erbB1, erbB1 and erbB3, erbB1 and erbB4, erbB2 and erbB3, erbB2 and erbB4, erbB3 and erbB4, and assembly epitopes of TNF or IgSF receptors, the present invention encompasses molecules, including but not limited to antibodies and peptide mimetics, based on interacting surfaces of receptors.

In certain embodiments, an antibody is specific to at least one dimerization site of an erbB, TNF, or IgSF receptor. In certain embodiments, antibodies are specific to at least one dimerization site of erbB1 or erbB2. Binding of the antibody to the dimerization site may effectively prevent the dimerization of the receptor, and, preferably, reduce or eliminate receptor signaling.

In certain embodiments, antibodies are specific to conformation sites of erbB, TNF, or IgSF receptors. In a preferred embodiment, antibodies are specific to a conformation site of erbB1 or erbB2. In some embodiments, antibodies are specific to a conformation site of erbB1 or erbB2. Binding of the antibody to the conformation site changes the conformation of the receptor such that the receptor is not able to dimerize, and, preferably, reduces or eliminates receptor signaling.

In certain embodiments, antibodies are provided which bind to cystine knot comprising regions or cystine knots or portions thereof of erbB, TNF, or IgSF receptors. In some embodiments, antibodies are specific for cystine knot in an extracellular domain of an erbB, TNF, or IgSF receptor.

While the teaching herein generally refers to antibodies, e.g., dual-specificity antibodies, that bind to specific activated dimers, for example, erbB1 and erbB2, the description is intended to embrace embodiments using antibodies, e.g., dual-specificity antibodies, that bind to other activated erbB, TNF, or IgSF receptors in place of antibodies, e.g., dual-specificity antibodies, that bind to activated erbB2 and erbB1, to treat, prevent, image and diagnose tumors that express the various combinations for which the antibodies are specific. Furthermore, the invention includes epitope specific antibodies, including, for example, cross reactive antibodies, that bind to at least one epitope on any pair of receptors which assemble into active homo or heteroligomers and use cystine knot like regions to do so. This includes the TNF receptor family (e.g., TNF receptor FAS, RANK, TRAIL, CD40), as well as the other members of the erbB family.

According to a preferred embodiment, a dual-specificity antibody has higher affinity against the activated erbB or TNF receptors and thus selectively affects highly proliferating cells with an activated signaling pathway. In certain preferred embodiments, the signaling pathway is the phosphatidylinositol 3-kinase (PI 3-kinase) pathway. These antibodies and the uses thereof are an improvement over mono-specific erbB or TNF receptor antibodies already in use. The treatment of the invention can thus be expected to reduce or eliminate the serious side effects of mammalian cancer tumor treatments or inflammation or IgSF-mediated pathologies because it does not interfere with any part of the body except the tumor.

In certain embodiments, methods of generating antibodies specific for activated cell surface receptors, e.g., dual-specificity antibodies, are provided. Such methods comprise priming with a cell-bound receptor and boosting with a member of the same receptor family. In some embodiments, a host animal is primed with no more than two immunizations of the cell-bound receptor and followed by boosting the host animal no more than two times with a member of the same family. In some embodiments, the method comprises priming the host animal no more than two times with a mixture of two or more related antigens and boosting the host animal no more than two times with the mixture of two or more related antigens.

In certain embodiments, a host animal is primed with no more than three immunizations of the cell-bound receptor and thereafter boosted no more than three times with a member of the same family. In some embodiments, the method comprises priming the host animal no more than three times with a mixture of two or more related antigens and thereafter boosting the host animal no more than three times with the mixture of two or more related antigens.

In certain embodiments, a host animal is primed with no more than four immunizations of the cell-bound receptor and thereafter boosted no more than four times with a member of the same family. In some embodiments, the method comprises priming the host animal no more than four times with a mixture of two or more related antigens and thereafter boosting the host animal no more than four times with the mixture of two or more related antigens.

In certain embodiments, a host animal is primed with no more than five immunizations of the cell-bound receptor and thereafter boosted no more than five times with a member of the same family. In some embodiments, the method comprises priming the host animal no more than five times with a mixture of two or more related antigens and thereafter boosting the host animal no more than five times with the mixture of two or more related antigens.

In certain embodiments, a host animal is primed with no more than six immunizations of the cell-bound receptor and thereafter boosted no more than six times with a member of the same family. In some embodiments, the method comprises priming the host animal no more than six times with a mixture of two or more related antigens and thereafter boosting the host animal no more than six times with the mixture of two or more related antigens.

It is to be understood that the methods of the present invention include various combinations of the priming and boosting steps set forth above. As non-limiting examples, in some embodiments, the methods comprise one priming step and three boosting steps. In some embodiments, the methods comprise two priming steps and three boosting steps.

Peptides and Mimetics

In certain embodiments, the invention provides antibodies, e.g., dual-specificity antibodies, that recognize and bind peptide mimetics. Preferably the mimetics are erbB mimetics. More preferably the mimetics are erbB subdomain IV mimetics. Most preferably the mimetics are erbB subdomain IV mimetics S22 and S23. Accordingly, the invention describes these mimetics and antibodies that bind thereto.

The present invention also provides, inter alia, constrained peptides that contain exocyclic portions including exocyclic amino acids that are aromatic amino acids as well as an active region which specifically binds to erbB and antibodies that bind thereto. Examples of constrained peptides are found in U.S. Pat. No. 6,100,377 and U.S. application Ser. No. 10/119,288, filed Apr. 8, 2002. Peptides can be prepared according to the methods described in Takasaki et al., (1997) *Nature Biotech.*, 15:1266-1270 and Park et al., (2000) *Nature Biotech.*, 18:194-198.

The present invention also relates to mimetics which specifically bind to erbB and antibodies that bind thereto.

The present invention is useful to therapeutically treat an individual identified as suffering from erbB tumors in order to reverse the transformed phenotype of the tumor cells. The present invention is also useful to prophylactically treat an individual who is predisposed to develop an erbB tumors or who has had erbB-associated tumors and is therefore susceptible to a relapse or recurrence. The present invention is also useful to detectably image tumors with respect to erbB receptors on their surfaces. The present invention is further useful to detect and quantify erbB on cell surfaces.

According to certain embodiments, the present invention provides peptides having the formula, and antibodies that bind thereto:

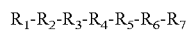

wherein:
  $R_1$ is 1-6 amino acid residues, at least one of which is tyrosine or phenylalanine;
  $R_2$ is a linking moiety which bonds with $R_1$, $R_3$ and $R_6$ such that a portion of said peptide is cyclicized;
  $R_3$ is 0-20 amino acids;
  $R_4$ is 6-12 amino acids;
  $R_5$ is 0-20 amino acids;
  $R_6$ is a linking moiety which bonds with $R_5$, $R_7$ and $R_2$ such that a portion of said peptide is cyclicized;
  $R_7$ is 1-6 amino acid residues, at least one of which is tyrosine or phenylalanine;
  wherein: $R_1$, $R_2$, $R_3$, $R_4$, $R_5$, $R_6$ and $R_7$, taken together, are 30 amino acids or less.

In certain embodiments, $R_4$ comprises F-P-D-E-E-G-A (SEQ ID NO:1). In some embodiments, $R_4$ consists of F-P-D-E-E-G-A (SEQ ID NO:1). In some embodiments, $R_4$ comprises F-Y-P-D-E-E-G-A (SEQ ID NO:2). In some embodiments, $R_4$ consists of F-Y-P-D-E-E-G-A (SEQ ID NO:2).

The primary function of $R_1$ arises from the presence of at least one amino acid that contains an aromatic group: i.e., the presence of tyrosine or phenylalanine. The presence of the aromatic amino acid at position $R_1$ results in an increased affinity of the peptide to erbB and an attendant increase in activity of the compound. In embodiments where additional amino acid residues are present, they can present the aromatic amino acid in a more effective position to further increase the affinity and activity of the compound. Additional amino acids that may be present must not eliminate the effect that the aromatic amino acid has on affinity or activity. Examples of amino acid sequences which may be used as $R_1$ are disclosed in U.S. Pat. No. 6,100,377. In some embodiments, the additional amino acids are present as a site for linkage to detectable labels or moieties. In some embodiments, the additional amino acids are present as a site for dimerization with other peptides; either for formation of homodimers with each other or heterodimers with other peptides.

In some preferred embodiments, $R_1$ is 1-5 amino acids. In some preferred embodiments, $R_1$ is 4 amino acids. In some preferred embodiments, $R_1$ is 3 amino acids. In some preferred embodiments, $R_1$ is 2 amino acids. In some preferred embodiments, $R_1$ is 1 amino acid. In some preferred embodiments, $R_1$ comprises S—Y. In some preferred embodiments, $R_1$ consists of S—Y. In some preferred embodiments, $R_1$ comprises G-S—Y. In some preferred embodiments, $R_1$ consists of G-S—Y. In some preferred embodiments, $R_1$ consists of Y. In some preferred embodiments, $R_1$ consists of K. In some preferred embodiments, $R_1$ comprises K. Other examples of $R_1$ include G-G-S-Y (SEQ ID NO:21) and G-G-G-S-Y (SEQ ID NO:22). Contemplated equivalents include aromatic functional groups at $R_1$ which are not part of tyrosine or phenylalanine.

The function of $R_2$ is to form bonds with $R_1$ as well as to form bonds with $R_6$ which cyclicize or otherwise conformationally restrict the molecule. Bonds between $R_2$ and $R_6$ cyclicize the molecule and thereby maintain $R_3$-$R_4$-$R_5$, and, specifically $R_4$, in a constrained conformation that produces the specific biologically active surface that has an affinity for and interacts with erbB. Further, in such an arrangement $R_1$ becomes an exocyclic portion of the peptide. Accordingly, $R_2$ may be any moiety capable of forming bonds with $R_6$ as well as $R_1$ and $R_3$.

$R_2$ is preferably an amino acid residue. In certain embodiments, $R_2$ is a moiety that facilitates cyclization via $NH_2$ or SH groups, e.g., Tyr-Cys-Phe, Tyr-D-penicillamine-Phe, Phe-Lys-Tyr or Lys-Cys-Phe. More prefereably, $R_2$ is cysteine. When both $R_2$ and $R_6$ are cysteine, the disulfide bonds formed between the two cysteines cyclicize the molecule. It is contemplated that $R_2$ may comprise any moiety that, together with $R_6$, will allow for the cyclization of the portion of the molecule that includes $R_1$-$R_2$-$R_3$-$R_4$-$R_5$-$R_6$ while rendering $R_1$ and $R_7$ exocyclic portions of the peptide. Those having ordinary skill in the art can readily prepare peptides according to the present invention in which $R_2$ and $R_6$ are moieties capable of forming bonds to each other. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers*, 33:1037-1049; Wood, et al., (1992) *J. Pep. Prot. Res.*, 39:533-539; Saragovi, et al., (1992) *Immunomethods*, 1:5-9; Saragovi, et al., (1991) *Science*, 253: 792-795; Manning, et al., (1993) *Reg. Peptides*, 45:279-283; Hruby, (1993) *Biopolymers*, 33:1073-1082; Bach, et al., (1994) *New Adv. Peptidomimetics Small Mol. Design*, I:1-26; and Matsuyama, et al., (1992) *J. Bacteriol.*, 174:1769-1776, each of which are incorporated herein by reference.

The function of $R_3$ is to serve as a spacer and provide structure to present the active region in proper conformation. In some embodiments, the cyclization of the active region by particular linking moieties results in the proper folding of the active region to place it in active conformation and no $R_3$ is required. In some embodiments, the cyclization of the active region by particular linking moieties requires additional spacing and turns to facilitate that proper folding of the active region in order to place it in active conformation. In such embodiments, amino acid residues or sequences may be provided at $R_3$. In some preferred embodiments, $R_3$ is 0-10 amino acids. In some preferred embodiments, $R_3$ is 0-5 amino acids. In some embodiments $R_3$ is a sequences that adopts the secondary structure pf a β-turn/helix, e.g., D-P-P-F. In an alternative embodiment, $R_3$ is a sequence that adopts the a helical secondary structure, e.g., Ala-Ala-Ala.

$R_4$ is the active region of the compounds according to this aspect of the invention. In compounds of the invention, the functional groups of the active region are in a conformation which places them in a particular three dimensional arrangement that allows them to interact with the amino acids and functional groups thereon of an erbB receptor and to bind to an erbB receptor through such interactions. In peptide mimetics, the functional groups are provided in the active three-dimensional arrangement but are connected to modified or different backbones. It is possible to vary each residue with one that contributes equivalent bulk and hydrophobic moment and that still permits hydrogen bonding to surrounding water molecules or to residues to which the compound attaches. Examples of sequences suitable for use as $R_4$ include D-E-E-G or F-K-Y-A-D. These residues can be L-isomer or D-isomer.

The function of $R_5$ is to present the active region in proper conformation. In some embodiments, the cyclization of the active region by particular linking moieties results in the proper folding of the active region to place it in active conformation and no $R_5$ is required. In some embodiments, the cyclization of the active region by particular linking moieties requires additional spacing and turns to facilitate that proper folding of the active region in order to place it in active conformation. In such embodiments, amino acid residues or sequences may be provided at $R_5$. In some preferred embodiments, $R_5$ is 0-10 amino acids. In some preferred embodiments, $R_5$ is 0-5 amino acids. In some preferred embodiments, $R_5$ is 0 amino acids. In some embodiements, $R_5$ comprise a sequence that facilitates folding, e.g., D-P-E-P. Alternatively, $R_5$ can comprise a sequence that alters a chemical property of the peptide such as solubility, e.g., K-E-K-H.

The function of $R_6$ is to form bonds with $R_2$ which cyclicize or otherwise conformationally restrict the molecule. Bonds between $R_6$ and $R_2$ cyclicize the molecule and thereby maintain $R_3$-$R_4$-$R_5$, and, specifically $R_4$, in a constrained conformation that produces the specific biologically active surface that has an affinity for and interacts with erbB. Accordingly, $R_6$ may be any moiety capable of forming bonds with $R_2$ as well as $R_5$ and $R_7$. $R_6$ is preferably an amino acid residue, preferably cysteine. When both $R_6$ and $R_2$ are cysteine, disulfide bonds formed between the two cysteines cyclicize the molecule. In certain embodiments, $R_6$ can be, for example, G-C-Y, G-K-Y or G-D-penicillamine-Y. It is contemplated that $R_6$ may comprise any moiety that, together with $R_2$, will allow for the cyclization of the molecule. Those having ordinary skill in the art can readily prepare peptides according to the present invention in which $R_2$ and $R_6$ are moieties capable of forming bonds to each other. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers,* 33:1037-1049; Wood, et al., (1992) *J. Pep. Prot. Res.,* 39:533-539; Saragovi, et al., (1992) *Immunomethods,* 1:5-9; Saragovi, et al., (1991) *Science,* 253: 792-795; Manning, et al., (1993) *Reg. Peptides,* 45:279-283; Hruby, (1993) *Biopolymers,* 33:1073-1082; Bach, et al., (1994) *New Adv. Peptidomimetics Small Mol. Design,* I:1-26; and Matsuyama, et al., (1992) *J. Bacteriol.,* 174:1769-1776, each of which are incorporated herein by reference.

The primary function of $R_7$ in compounds of the present invention arises from the presence of at least one amino acid that contains an aromatic group: i.e. the presence of tyrosine or phenylalanine. The presence of the aromatic amino acid at position $R_7$ results in an increased affinity of the peptide to erbB and an attendant increase in activity of the compound. In embodiments where additional amino acid residues are present, they can present the aromatic amino acid in a more effective position to further increase the affinity and activity of the compound. Additional amino acids that may be present must not eliminate the effect that the aromatic amino acid has on affinity or activity. Examples of amino acid sequences which may be used as $R_7$ are disclosed in U.S. Pat. No. 6,100,377.

In some embodiments, the additional amino acids are present as a site for linkage to detectable labels or moieties. In some embodiments, the additional amino acids are present as a site for dimerization with other peptides; either for formation of homodimers with each other or heterodimers with other peptides.

In some preferred embodiments, $R_7$ is 1-5 amino acids. In some preferred embodiments, $R_7$ is 4 amino acids. In some preferred embodiments, $R_7$ is 3 amino acids. In some preferred embodiments, $R_7$ is 2 amino acids. In some preferred embodiments, $R_7$ is 1 amino acid. In some preferred embodiments, $R_7$ comprises Y-G-G-S (SEQ ID NO:27). In some preferred embodiments, $R_7$ consists of Y-G-G-S (SEQ ID NO:27). In some preferred embodiments, $R_7$ comprises Y-G-G-G (SEQ ID NO:23). In some preferred embodiments, $R_7$ consists of Y-G-G-G (SEQ ID NO:23). In some preferred embodiments, $R_7$ comprises Y-G-G-G-S (SEQ ID NO:24). In some preferred embodiments, $R_7$ consists of Y-G-G-G-S (SEQ ID NO:24). In some preferred embodiments, $R_7$ comprises Y. In some preferred embodiments, $R_7$ consists of Y. In some preferred embodiments, $R_7$ comprises Y-G-G. In some preferred embodiments, $R_7$ consists of Y-G-G. Another example of $R_7$ is Y-G. Contemplated equivalents include aromatic functional groups at $R_7$ which are not part of tyrosine or phenylalanine.

In some preferred embodiments, $R_1$ and $R_7$ collectively contain both tyrosine and phenylalanine. That is, if $R_1$ comprises tyrosine then $R_7$ comprises phenylalanine and if $R_1$ comprises phenylalanine then $R_7$ comprises tyrosine. In some preferred embodiments, $R_1$ and $R_7$ do not both contain tyrosine or phenylalanine. That is, if $R_1$ comprises tyrosine and not phenylalanine then $R_7$ comprises phenylalanine and not tyrosine and if $R_1$ comprises phenylalanine and not tyrosine then $R_7$ comprises tyrosine and not phenylalanine.

In some preferred embodiments, $R_1$, $R_2$, $R_3$, $R_4$, $R_5$, $R_6$ and $R_7$, taken together, are less than 30 amino acids. In some preferred embodiments, $R_1$, $R_2$, $R_3$, $R_4$, $R_5$, $R_6$ and $R_7$, taken together, are 20 amino acids or less. In some preferred embodiments, $R_1$, $R_2$, $R_3$, $R_4$, $R_5$, $R_6$ and $R_7$, taken together, are less than 20 amino acids. In some preferred embodiments, $R_1$, $R_2$, $R_3$, $R_4$, $R_5$, $R_6$ and $R_7$, taken together, are 15 amino acids. In some preferred embodiments, $R_1$, $R_2$, $R_3$, $R_4$, $R_5$, $R_6$ and $R_7$, taken together, are less than 15 amino acids. In some preferred embodiments, $R_1$, $R_2$, $R_3$, $R^4$, $R_5$, $R_6$ and $R_7$, taken together, are 14 amino acids. In some preferred embodiments, $R_1$, $R_2$, $R_3$, $R_4$, $R_5$, $R_6$ and $R_7$, taken together, are 13 amino acids. In some preferred embodiments, $R_1$, $R_2$, $R_3$, $R_4$, $R_5$, $R_6$ and $R_7$, taken together, are 12 amino acids. In some preferred embodiments, $R_1$, $R_2$, $R_3$, $R_4$, $R_5$, $R_6$ and $R_7$, taken together, are 11 amino acids. In some preferred embodiments, $R_1$, $R_2$, $R_3$, $R_4$, $R_5$, $R_6$ and $R_7$, taken together, are 10 amino acids.

In some embodiments, the peptide is selected from the group consisting of: Y-C-F-P-D-E-E-G-A-C-Y (SEQ ID NO:3); S-Y-C-F-P-D-E-E-G-A-C-Y (SEQ ID NO:4); G-S-Y-C-F-P-D-E-E-G-A-C-Y (SEQ ID NO:5); G-G-S-Y-C-F-P-D-E-E-G-A-C-Y (SEQ ID NO:6); G-G-G-S-Y-C-F-P-D-E-E-G-A-C-Y (SEQ ID NO:7); Y-C-F-P-D-E-E-G-A-C-Y-G (SEQ ID NO:8); Y-C-F-P-D-E-E-G-A-C-Y-G-G (SEQ ID NO:9); Y-C-F-P-D-E-E-G-A-C-Y-G-G-G (SEQ ID NO:10); Y-C-F-P-D-E-E-G-A-C-Y-G-G-G-S (SEQ ID NO:11); Y-C-F-Y-P-D-E-E-G-A-C-Y (SEQ ID NO:12); S-Y-C-F-Y-P-D-E-E-G-A-C-Y (SEQ ID NO:13); G-S-Y-C-F-Y-P-D-E-E-G-A-C-Y (SEQ ID NO:14); G-G-S-Y-C-F-Y-P-D-E-E-G-A-C-Y (SEQ ID NO:15); G-G-G-S-Y-C-F-Y-P-D-E-E-G-A-C-Y (SEQ ID NO:16); Y-C-F-Y-P-D-E-E-G-A-C-Y-G (SEQ ID NO:17); Y-C-F-Y-P-D-E-E-G-A-C-Y-G-G (SEQ ID NO:18); Y-C-F-Y-P-D-E-E-G-A-C-Y-G-G-G (SEQ ID NO:19); and Y-C-F-Y-P-D-E-E-G-A-C-Y-G-G-G-S (SEQ ID NO:20); YCFPDEEGACYK (SEQ ID NO:25); and YCFPDEEGACYGGS (SEQ ID NO:26). Other peptides are included within the scope of the present invention comprising different combinations of $R_1$, $R_2$, $R_3$, $R_4$, $R_5$, $R_6$ and $R_7$.

In some embodiments, terminal residues of the peptides are modified. In some embodiments, the terminal residue of $R_1$ is modified with —OH. In some embodiments, the terminal residue of $R_1$ is modified with —NH$_2$. In some embodiments, the terminal residue of $R_7$ is modified with —OH. In some embodiments, the terminal residue of $R_7$ is modified with —NH$_2$.

According to some embodiments,

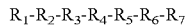

together form a peptide wherein:
$R_1$ is 1-3 amino acid residues, at least one of which is tyrosine or phenylalanine;
$R_2$ is cysteine or pencillamine;
$R_3$ is 0 amino acids;
$R_4$ is 7-8 amino acids;
$R_5$ is 0 amino acids;
$R_6$ is cysteine or pencillamine;
$R_7$ is 1-5 amino acid residues, at least one of which is tyrosine or phenylalanine;

wherein:
$R_1$, $R_2$, $R_3$, $R_4$, $R_5$, $R_6$ and $R_7$, taken together, are 30 amino acids or less, and wherein $R_1$, $R_2$, $R_3$, $R_4$, $R_5$, $R_6$ and $R_7$ are otherwise as set forth above.

In certain embodiments the peptide is B2-S23-BPT: P-C-P-I-N-C-T-H-S-C-V-D-L-D-D-K-G-C-P-A-E-Q-R-A-S-P-L-T-S-I (SEQ ID NO: 38).

In some preferred embodiments of generating dual-reactive monoclonal antibodies against IgSF members, the peptide is: C-K-V-E-L-M-Y-P-P-P-Y-F-V-G-M-G-N-G-T-Q-I-Y-V-I-D-P-E-P-C (SEQ ID NO: 36).

In some preferred embodiments of generating dual-reactive monoclonal antibodies against IgSF members, the peptide is: C-K-I-E-F-M-Y-P-P-P-Y-L-D-N-E-R-S-N-G-T-I-I-H-I-K-E-K-H-L-C (SEQ ID NO: 29).

In some preferred embodiments the peptide is: C-S-L-S-I-F-D-P-P-P-F-Q-E-R-N-L-S-G-G-Y-L-H-I-Y-E-S-Q-L-C (SEQ ID NO: 30).

In some preferred embodiments the peptide is B2-S22-APE: Y-C-P-I-W-K-F-P-D-E-E-C-Y (SEQ ID NO: 31).

In some preferred embodiments the peptide is B1-S22-ALG: Y-C-L-V-W-K-Y-A-D-A-G-C-Y (SEQ ID NO: 32).

In some preferred embodiments the peptide is B3-S22-APQ: Y-C-P-I-Y-K-Y-P-D-V-Q-C-Y (SEQ ID NO: 33).

In some preferred embodiments the peptide is B4-S22-AFD: Y-C-F-I-F-K-Y-A-D-P-D-C-Y (SEQ ID NO: 34).

In some preferred embodiments the peptide is B2-S22-AFA: Y-C-F-P-D-E-E-G-A-C-Y (SEQ ID NO: 35).

Those having ordinary skill in the art can readily construct molecules according to the above formulae and determine whether or not the compounds are active as erbB binding compounds which prevent and eliminate the erbB-mediated transformation phenotype.

Peptides useful in the invention may be dimerized with each other to form homodimers or with other compounds including compounds of the invention to form heterodimers. In preferred dimers, the residues involved in the chemical bond which links the monomers is in the $R_1$ position of the compounds of the invention.

Mimetics of the peptides which mimic erbB, TNF, or IgSF receptors may be produced. Such mimetics may be tested in the assays set forth in the Examples.

According to the present invention, peptides and mimetics that mimic sites on erbB, TNF, or IgSF receptors and antibodies that recognize such peptides and mimetics are useful to prevent dimerization of receptors and thereby down modulate the kinase activity of the receptors. When bound, the peptides and mimetics or antibodies that bind thereto eliminate or reduce tyrosine kinase activity and/or receptor signaling that results in an elimination or reduction in cell proliferation levels and a non-transformed, quiescent phenotype. The peptides and mimetics and antibodies that bind thereto are therefore useful in the treatment of individuals suspected of having erbB tumors or TNF and IgSF-mediated pathologies, and in the prevention of such erbB tumor formation. The cells in the individuals that would turn into tumors in an untreated individual do not become fully transformed and do not become tumors in individuals treated by the methods.

When administered to individuals who have been identified as being susceptible to or otherwise at risk of developing tumors, the peptides and mimetics may induce production of antibodies that bind to erbB or TNF monomers, thereby preventing the elevation in tyrosine kinase activity or signaling associated with oligomerization of the receptors. The tyrosine kinase activity in the cell may never become sufficiently elevated and the cell remains non-transformed. Most preferably, the induced antibodies are dual-specificity antibodies.

Peptides and mimetics of erbB receptors, TNF or IgSF family receptors are useful in anti-tumor compositions and can be produced by those skilled in the art using readily available starting materials. U.S. Pat. No. 5,637,677 and its parent applications thereof disclose detailed guidance on the production of mimetics.

According to preferred embodiments, a peptide or mimetic is designed based on a known region of an erbB, TNF, or IgSF receptor. In some preferred embodiments, the peptide or mimetic mimics an extracellular domain of an erbB, TNF, or IgSF receptor. In some more preferred embodiments, the peptide or mimetic mimics the second cysteine rich domain proximal to the transmembrane domain (S22 loop). In some preferred embodiments, the peptide mimetic mimics of the S23 loop. According to some embodiments, the peptide mimetics of the present invention mimic cystine knots comprising regions.

In some preferred embodiments, the peptides and/or mimetics are exocyclic. In some preferred embodiments, the peptides and/or mimetics mimic full cystine knots. In some embodiments, the peptides and/or mimetics mimic a portion of a cystine knot.

In addition, peptides and/or mimetics may mimic assembly or functional epitopes of erbB2 and erbB1, erbB1 and erbB3, erbB1 and erbB4, erbB2 and erbB3, erbB2 and erbB4, erbB3 and erbB4, assembly or functional epitopes of TNF receptors, or assembly and functional epitopes of IgSF members.

Peptides and/or mimetics are provided which mimic dimerization sites of erbB, TNF, or IgSF receptors and induce antibodies. In a preferred embodiment, the peptides and/or mimetics mimic a dimerization site of erbB1 or erbB2. Binding of the peptides and/or mimetics or induced antibodies to the dimerization site prevents the dimerization of the receptor, and, preferably, reduces or eliminates receptor signaling.

In some embodiments, peptides and/or mimetics are provided which mimic conformation sites of erbB, TNF, or IgSF receptors and induce antibodies. In a preferred embodiment, the peptides and/or mimetics mimic a conformation site of erbB1 or erbB2. Binding of the peptides and/or mimetics or induced antibodies to the conformation site changes the conformation of the receptor and prevents the dimerization of the receptor, and, preferably, reduces or eliminates receptor signaling.

The peptides and/or mimetics of the invention are useful in the treatment of erbB tumors either as a component of a composition administered to a patient, as a component of a composition administered to a patient in combination with radiation therapy and/or chemotherapy, or as a component of a composition administered to a patient that comprises the peptides and/or mimetics conjugated to a radioactive or chemotherapeutic agent.

The peptides and/or mimetics of the invention are useful in the prevention of erbB tumors or TNF- or IgSF-mediated pathologies either as a component of a composition administered to a patient, as a component of a composition administered to a patient in combination with radiation therapy and/or chemotherapy, or as a component of a composition administered to a patient that comprises the peptides and/or mimetics conjugated to a radioactive or chemotherapeutic agent.

The peptides and/or mimetics are useful for raising antibodies. In some embodiments, an antibody is produced by immunizing a suitable host with a peptide selected from the group consisting of: Y-C-F-P-D-E-E-G-A-C-Y (SEQ ID NO:3); C-K-V-E-L-M-Y-P-P-P-Y-F-V-G-M-G-N-G-T-Q-I-Y-V-I-D-P-E-P-C (SEQ ID NO: 28); C-K-I-E-F-M-Y-P-P-P-Y-L-D-N-E-R-S-N-G-T-I-I-H-I-K-E-K-H-L-C (SEQ ID NO: 29); C-S-L-S-I-F-D-P-P-P-F-Q-E-R-N-L-S-G-G-Y-L-H-I-Y-E-S-Q-L-C (SEQ ID NO: 30); B2-S22-APE: Y-C-P-I-W-K-F-P-D-E-E-C-Y (SEQ ID NO: 31); B1-S22-ALG: Y-C-L-V-W-K-Y-A-D-A-G-C-Y (SEQ ID NO: 32); B3-S22-APQ: Y-C-P-I-Y-K-Y-P-D-V-Q-C-Y (SEQ ID NO: 33); B4-S22-AFD: Y-C-F-I-F-K-Y-A-D-P-D-C-Y (SEQ ID NO: 34); B2-S22-AFA: Y-C-F-P-D-E-E-G-A-C-Y (SEQ ID NO: 35). In preferred embodiments, the antibody is a dual specificity antibody. In some embodiments the antibody binds to a cysteine rich domain of an erbB receptor. In some embodiments, the peptides or mimetics induce antibodies that bind to functional sites of erbB, TNF, or IgSF family receptors.

The invention contemplates antibodies produced by immunizing a suitable host with a peptide selected from the group consisting of SEQ ID NOS:1-37 as well as antibodies produced by immunizing a suitable host with a peptide having the sequence in reverse order selected from the group consisting of SEQ ID NOS:1-37.

Anti-HER2/p185$^{c\text{-}neu}$ Antibody Binds to the Ectodomain and Leads to p185 Internalization Disabling a protein responsible for maintenance of the malignant phenotype reverses transformation. This body of work (Drebin, et al. 1986, Symp Fundam Cancer Res 38:277-289; Drebin, et al. 1986, Proc Natl Acad Sci USA 83:9129-9133) was subsequently substantiated (Carter, et al. 1992) and has now has been approved for clinical use as "HERCEPTIN" (Baselga, et al. 1998; Pegram, et al. 1998).

Antibodies to the ectodomain of p185 can reverse the phenotype of transformed cells by leading to the rapid downmodulation of the receptor from the cell surface (Drebin, et al. 1986, Proc Natl Acad Sci USA 83:9129-9133). The removal of the transforming receptor from the cell surface in vitro was associated with a reduction in the malignant phenotype and a conversion of the cell phenotype into a more normal one as judged by cell growth, phenotype, and growth in soft agar. The anti-receptor antibody p185 complex was visualized and shown to enter the cell and lead to p185 degradation (Brown, et al. 1994). Subsequent in vivo studies showed that the administration of anti-receptor antibodies alone could cause retardation of tumor growth.

Studies in small animals which had been treated to eliminate complement or macrophages clearly indicated that the effect of the antibodies was predominantly but not entirely direct and was related to receptor downmodulation (Drebin, et al. 1988).

Cyclic Peptidomimetics are Superior Immunogens

Antigenic sites recognized by antibody consist of discrete three-dimensional surfaces (Van Regenmortel 1989; Van Regenmortel 1996). Spatial distribution of antigenic residues on the surface of proteins are often reproduced by constrained peptides (Nayak, et al. 1998; Posthumus, et al. 1991; Valero, et al. 1995; van der Werf, et al. 1994). An example involves the foot-mouth-and disease virus. A dominant antigenic site consists of flexible loop and immunization with a constrained peptide of this loop elicits higher affinity and neutralizing antibodies than the MAb elicited by linear peptides (Patel, et al. 1999; Valero, et al. 1995). These studies suggest that rigid, but spatial mimics of antigenic regions can be useful as immunogens and may be used to induce MAb to erb receptor interaction surfaces.

Therapeutic Methods

The present invention is useful to therapeutically treat an individual identified as suffering from erbB tumors and/or TNF or IgSF-related pathologies in order to reverse the transformed phenotype of the tumor cells and/or induce tumor cell death. The present invention is also useful to prophylactically treat an individual who is predisposed to develop erbB tumors and/or TNF or IgSF-related pathologies or who has had erbB tumors and/or TNF or IgSF-related pathologies and is therefore susceptible to a relapse or recurrence.

When a therapeutically effective amount of an antibody, peptide or mimetic of the present invention is administered to an individual who has erbB cancer, the proliferation rate of tumor cells is slowed down or eliminated.

Prophylactic methods are useful to treat an individual who is predisposed to develop erbB tumors and/or TNF or IgSF-related pathologies or who has had erbB tumors and/or TNF or IgSF-related pathologies and is therefore susceptible to a relapse or recurrence.

In some embodiments, the methods relate to treating patients suffering from human adenocarcinomas such as gastric, lung and pancreatic adenocarcinomas and human breast and ovarian carcinomas as well as human prostate cancer. In some embodiments, the methods relate to treating patients suffering from glial tumor progression, particularly in glioblastoma, the most malignant glial tumor. In some embodiments, the methods relate to treating patients suffering from human epithelial malignancies erythroid leukemia, fibrosarcoma, angiosarcoma and melanoma. In some embodiments the present invention provides methods of treating such diseases/disorders comprising the step of diagnosing a patient a suffering from a multimer-associated disease/disorder and then treating the disease/disorder in accordance with other methods of the invention.

Radiation therapy may commence anytime after a sufficient amount of time has elapsed for the antibodies or peptide mimetics to bind to the receptors. Generally, the individual is exposed to radiation in some cases 1-10 minutes after, in some cases 1-10 hours after, and in some cases up to 24-72 hours after administration of the antibodies, peptides or mimetics. In some cases, the radiation is provided in a single dose while in some embodiments, multiple doses are administered over several hours, days and/or weeks. The antibodies render the radiation resistant tumor cells radiation sensitive. Gamma radiation is delivered according to standard radiotherapeutic protocols using standard dosages and regimens. The administration of the antibodies, peptides or mimetics renders the radiation more effective in eradicating tumor cells.

The individual may be treated with antibodies, peptides or mimetics in combination with a cytotoxic chemotherapeutic agent in addition to or in lieu of exposure to a therapeutic amount of gamma radiation. Chemotherapy may commence anytime before or after the antibodies or peptide mimetics are administered, or with the antibodies, peptides or mimetics themselves. Generally, the individual is administered the chemotherapeutic in some cases 1-10 minutes after, in some cases 1-10 hours after, and in some cases up to 24-72 hours after administration of the antibodies, peptides or mimetics. In some cases, the chemotherapeutic is provided in a single dose while in some embodiments, multiple doses are administered over several hours, days and/or weeks. The antibodies render the tumor cells more sensitive to cytotoxic agents. Chemotherapeutic agents are delivered according to standard radiotherapeutic protocols using standard agents, dosages and regimens. In some embodiments, the chemotherapeutic agent is selected from the group consisting of: cisplatin, doxirubicin, danurubicin, tamoxiphen, taxol, and methotrexate. In some embodiments, the individual is treated with antibodies and/or peptides and/or mimetics of the present invention in combination with two or more chemotherapeutics, each administered prior to, simultaneous with, or after the other chemotherapeutics. In some embodiments, chemotherapy and radiation treatments are both employed following the administration of the active agent. In such embodiments, standard combinations of two or more therapeutic modalities are used in conjunction with administration of the antibodies and/or peptides and/or mimetics.

According to some embodiments of the invention, the patient is treated with radiation and/or other chemotherapy in conjunction with the administration of pharmaceutical compositions according to the invention. Chemotherapy approaches include administration of cytotoxic and/or cytostatic agents. It has been observed that expression of nucleotide molecules according to the invention in erbB-associated tumors renders the tumors radiosensitized. That is, the tumors are more vulnerable to destruction by radiation during radiotherapy when the patient is treated with pharmaceutical compositions according to the invention. The use of multiple therapeutic approaches provides the patient with a broader based intervention. In some preferred embodiments, treatment with pharmaceutical compositions according to the present invention is preceded by surgical intervention. In preferred embodiments, radiotherapy follows administration of pharmaceutical compositions according to the invention. In preferred embodiments, the radiation therapy using gamma radiation is provided following administration of compositions which convert radiation resistant tumors into radiation sensitive tumors. Those skilled in the art can readily formulate an appropriate radiotherapeutic regimen. Carlos A Perez & Luther W Brady: Principles and Practice of Radiation Oncology, 2nd Ed. JB Lippincott Co, Phila., 1992, which is incorporated herein by reference describes radiation therapy protocols and parameters which can be used in the present invention. For GBMs (glioblastoma, the most malignant glial brain tumor), Simpson W. J. et al.: *Influence of location and extent of surgical resection on survival of patients with glioblastoma multiforms: Results of three consecutive Radiation Therapy Oncology Group (RTOG) clinical trials.* Int J Radiat Oncol Biol Phys 26:239-244, 1993, which is incorporated herein by reference, describes clinical protocols useful in the methods of the present invention. Similarly, for brain tumors, see Borgelt et al., *The palliation of brain metastases: Final results of the first two studies of the Radiation Therapy Oncology Group.* Int J Radiat Oncol Biol Phys 6:1-9, 1980, which is incorporated herein by reference and describes clinical protocols useful in the methods of the present invention.

The antibodies, peptides or mimetics of the present invention may be used to prevent tumors in individuals susceptible to such tumors. According to one aspect of the invention, antibodies are administered prophylactically to individuals susceptible to developing erbB tumors. Administration may be of any means known to those of ordinary skill in the art, such as those described herein, infra. According to another aspect of the invention, peptides are administered prophylactically to individuals susceptible to developing erbB tumors and/or TNF or IgSF-related pathologies. According to another aspect of the invention, mimetics are administered prophylactically to individuals susceptible to developing erbB tumors and/or TNF or IgSF-related pathologies. Those having ordinary skill in the art can readily determine whether an individual may be susceptible to such tumors. The methods are particularly useful in high-risk individuals who, for example, have a family history of erbB cancer, or show a genetic predisposition. Additionally, the methods are particularly useful to prevent patients from having recurrences of erbB tumors who have had erbB tumors removed by surgical resection or who have been diagnosed as having erbB-cancer in remission. In some preferred embodiments, the cancer is erbB2/erbB1 cancer.

Methods of treatment comprise administering single or multiple doses of the antibodies, peptides or mimetics. Preferred for human pharmaceutical use are injectable pharmaceutical compositions that are sterile, pyrogen free and comprise the antibodies, peptides or mimetics in combination with a pharmaceutically acceptable carrier or diluent.

The antibodies, peptides or mimetics of the present invention may be used to treat individuals suffering from erbB tumors. According to one aspect of the invention, antibodies are administered to individuals suspected of having such tumors. According to another aspect of the invention, peptide mimetics are administered to individuals suspected of having such tumors. Those having ordinary skill in the art can readily determine whether an individual may have a tumor likely to be an erbB tumor. Biopsy protocols can be performed to identify tumor samples and determine whether or not they are erbB tumors.

According to some aspects, the patient is treated with the antibodies, peptides or mimetics in conjunction with chemotherapy and/or radiation therapy. In some preferred embodiments, the cancer is erbB2/erbB 1 cancer. For example, following administration of the antibodies, peptides or mimetics, the patient may be treated with a therapeutically effective amount of anti-cancer radiation such as gamma radiation. Generally, an individual is exposed to radiation in some cases 1-10 minutes after, in some cases 1-10 hours after, in some cases up to 24-72 hours and in some cases 1-4 weeks or 1-4 months after administration of the antibody. In some cases, the radiation is provided in a single dose while in some embodiments, multiple doses are administered over several hours, days, weeks and/or months. Gammaradiation is delivered according to standard radiotherapeutic protocols using standard dosages and regimens.

Moreover, some embodiments provide chemotherapeutic treatment in combination with the antibodies, peptides or mimetics. Generally, the individual is administered the chemotherapeutic in some cases 1-10 minutes after, in some cases 1-10 hours after, in some cases up to 24-72 hours, in some cases 1-4 weeks or in some cases 1-6 months after administration of the anitbody. In some cases, the chemotherapeutic agent is provided in a single dose while in some embodiments, multiple doses are administered over several hours, days, weeks and or months. Chemotherapeutics are delivered according to standard radiotherapeutic protocols using standard agents, dosages and regimens. In some embodiments, the chemotherapeutic is selected from the group consisting of: cisplatin, doxirubicin, danurubicin, tamoxiphen, taxol, and methotrexate. In some embodiments, chemotherapy and radiation treatments are both employed following the administration of the antibody. In such embodiments, standard combinations of the two therapeutic modalities are used in conjunction with administration of the antibody.

Methods of Imaging and Diagnosing Mammalian Tumors

The present invention is also useful, inter alia, to image erbB tumors and TNF or IgSF-related pathologies and otherwise detect or diagnose them.

The antibodies, peptides or mimetics of the present invention can be labeled or otherwise made detectable. For example, a detectable antibody is useful as an imaging agent and reagent in diagnostic procedures that are used to identify tumors. Labeled antibodies can be administered to individuals suspected of suffering from erbB tumor and/or TNF or IgSF-related pathologies. The labeled antibodies will bind to the high density of receptors on cells and thereby accumulate on the tumor cells. Using standard imaging techniques, the site of the tumors can be detected.

One aspect of the invention therefore relates to methods of imaging tumors. Such methods comprise the steps of administering a detectable antibody, peptide or mimetic to an individual who is suffering from or is susceptible to erbB cancer and detecting the location of the detectable antibody, peptide or mimetic within the body of the individual or within a sample obtained from said individual.

The antibodies, peptides or mimetics bind to receptors present on cell surfaces and are therefore useful as diagnostic/characterizing reagents in diagnostic kits. When a tissue sample from an individual is contacted with an antibody, peptide or mimetic, the antibody, peptide or mimetic will bind to the receptors present on cells. Labeled antibodies, peptides or mimetics are also useful as in vitro reagents to quantify the amount of receptors present in the cell. Such information indicates whether or not a tumor is erbB-related and, therefore, whether specific treatments should be used or avoided. Using standard techniques, samples believed to include tumor cells are obtained and contacted with labeled antibodies, peptides or mimetics. After removing any unbound, labeled antibodies, peptides or mimetics, the quantity of labeled antibodies, peptides or mimetics bound to the cell, or the quantity of antibodies, peptides or mimetics removed as unbound, labeled antibodies is determined. The information directly relates to the amount of receptors. This information is useful in formulating the prognosis and course of treatment to be imposed on the individual.

Imaging agents are useful in diagnostic procedures as well as in procedures used to identify the location of tumors. Imaging can be performed by many procedures well-known to those having ordinary skill in the art and the appropriate imaging agent useful in such procedures may be conjugated to antibodies by well-known means. Imaging can be performed, for example, by radioscintigraphy, nuclear magnetic resonance imaging (MRI) or computed tomography (CT scan). The most commonly employed radiolabels for imaging agents include radioactive iodine and indium. Imaging by CT scan may employ a heavy metal such as an iron chelate. MRI scanning may employ chelates of gadolinium or manganese. Additionally, positron emission tomography (PET) may be possible using positron emitters of oxygen, nitrogen, iron, carbon, or gallium.

In another embodiment, a diagnostic method is provide in which radiolabeled F(ab)' fragments prepared from the monoclonal antibodies of the present invention are administered to patients. The location and size of the tumor are determined by gamma-scintigraphy to detect the radiolabeled F(ab)' fragments.

In some embodiments, tumors can be diagnosed by contacting tissue portions of the tumor with a dual-specificity antibody, the antibody being labeled with an indicator. The antibody binds to the shared epitope of the erbB oligomer present in the cells of the tissue portion. The indicator is then detected. In preferred embodiments of the invention, the indicator comprises biotinylated horse anti-mouse immunoglobulin and streptavidin-biotinylated-peroxidase. The indicator in detected by contacting the indicator with a chromogenic substrate which preferably comprises 3,3'-diaminobenzidine, hydrogen peroxide and imidazole. The chromogenic substrate is then detected by microscopy.

In some embodiments, tumors can be diagnosed by contacting tissue portions of the tumor with a labeled antibody, peptide or mimetic. The labeled antibody peptide or mimetic binds to the erbB receptor present in the cells of the tissue portion. The indicator is then detected. In preferred embodiments of the invention, the indicator comprises biotinylated horse anti-mouse immunoglobulin and streptavidin-biotinylated-peroxidase. The indicator is detected by contacting the indicator with a chromogenic substrate which preferably comprises 3,3'-diaminobenzidine, hydrogen peroxide and imidazole. The chromogenic substrate is then detected by microscopy.

Pharmaceutical Compositions

The invention further provides an injectable composition for treatment of a mammalian cancer tumor having cells that express erbB receptors or TNF receptors on the surfaces of the cells. The invention further provides an injectable composition for treatment of a mammalian cancer tumor having cells that overexpress erbB receptors or TNF receptors on the surfaces of the cells. In accordance with the invention, the composition comprises an antibody, peptide or mimetic specific to the shared epitope and a pharmaceutically acceptable injection vehicle.

When a therapeutically effective amount of an antibody, peptide or mimetic of the present invention is administered to an individual who has erbB cancer or TNF or IgSF-related pathology, the proliferation rate of cells is slowed down or eliminated.

The pharmaceutical compositions of the present invention may be administered by any means that enables the antibodies, peptides or mimetics to reach the agent's site of action in the body of a mammal. Because proteins are subject to being digested when administered orally, parenteral administration, i.e., intravenous, subcutaneous, intramuscular, would ordinarily be used to optimize absorption. Formulations may be devised which protect the antibodies, peptides or mimetics and render them resistant to many proteases, thus making them orally available.

In addition to pharmaceutical compositions which comprise antibodies, peptides or mimetics alone or in combination with other cancer therapeutics, therapeutic and diagnostic pharmaceutical compositions, the invention provides antibodies conjugated to, e.g., a chemotherapeutic, diagnostic, imaging or radiation agent. The pharmaceutical compositions which comprise conjugated antibodies may be used to diagnose or treat individuals suffering from erbB and/or TNF cancer.

The pharmaceutical compositions of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The compositions may include additional components to render them more effective. For example, a composition of the invention may comprise multiple anti-p185 antibodies. The compositions may include other anti-cancer agents such as, for example, cis-platin, methotrexate, and/or GM-CSF. For example, one preferred pharmaceutical composition for use in treating erbB tumors according to the present invention comprises an antibody specific for an activated erbB receptor, an anit-EGFr or anti-p185 antibody and, optionally, cis-platin. Such compositions would be particularly useful for administration to patients diagnosed and treated for erbB-associated cancer.

Generally, additives for isotonicity can include sodium chloride, dextrose, mannitol, sorbitol and lactose. In some cases, isotonic solutions such as phosphate buffered saline are used. Stabilizers include gelatin and albumin. The pharmaceutical preparations according to the present invention are preferably provided sterile and pyrogen free.

One of skill in the art of pharmaceutical formulations, e.g., having an advanced degree in Pharmaceutics or Pharmaceutical Sciences, can prepare a variety of appropriate dosage forms and formulations for the compositions of the invention with no more than routine experimentation. A number of texts in the field, e.g., *Remington's Pharmaceutical Sciences* and *The U.S. Pharmacopoeia/National Formulary*, latest editions, provide considerable guidance in this respect, each of which is incorporated by reference in its entirety A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

Kits

Kits of the invention comprise detectable antibodies and/or peptides and/or mimetics and instructions for performing assays of the invention. Optionally, kits may also contain one or more of the following: containers which comprise positive controls, containers which comprise negative controls, photographs of representative examples of positive results and photographs of representative examples of negative results.

Conjugates

Antibodies, peptides or mimetics may be conjugated to a detectable and/or cytotoxic agent. In conjugated compositions, the antibodies, peptides or mimetics of the invention deliver the active agent to cells. Thus, cells with the receptors will be contacted with more active agents than other cells. The active agent is useful to image, inhibit proliferation of and/or kill the cell. The active agent may be a therapeutic agent or an imaging agent.

Some chemotherapeutic agents may be used as active agents and conjugated with antibodies, peptides or mimetics. Chemotherapeutics are typically small chemical entities produced by chemical synthesis and include cytotoxic drugs, cytostatic drugs as well as antibodies which affect cells in other ways such as reversal of the transformed state to a differentiated state or those which inhibit cell replication. Examples of chemotherapeutics include, but are not limited to: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids, such as, for example vincristine and vinblastine), mitomycin and bleomycin.

Active agents may be toxins, such as, for example: complex toxic products of various organisms including bacteria, plants, etc. Examples of toxins include but are not limited to: ricin, ricin A chain (ricin toxin), *Pseudomonas exotoxin* (PE), diphtheria toxin (DT), *Clostridium perfringens* phospholipase C (PLC), bovine pancreatic rib onuclease (BPR), pokeweed antiviral protein (PAP), abrin, abrin A chain (abrin toxin), cobra venom factor (CVF), gelonin (GEL), saporin (SAP), modeccin, viscumin and volkensin. Protein toxins may be produced using recombinant DNA techniques as fusion proteins that include peptides of the invention. Protein toxins may also be conjugated to antibodies by non-peptidyl bonds.

Radioisotopes may be conjugated to antibodies, peptides or mimetics to provide compositions that are useful as therapeutic agents or for imaging procedures. Examples of radioisotopes which useful in radiation therapy include: $^{47}$Sc, $^{67}$Cu, $^{90}$Y, $^{109}$Pd, $^{123\,I}$, $^{125}$I, $^{131}$I, $^{186}$Re, $^{188}$Re, $^{199}$Au, $^{211}$At, $^{212}$Pb and $^{212}$Bi. Example of radioisotopes useful in imaging procedures include: $^{43}$K, $^{52}$Fe, $^{57}$Co, $^{67}$Cu, $^{67}$Ga, $^{68}$Ga, $^{77}$Br, $^{81}$Rb, $^{81M}$Kr, $^{87M}$Sr, $^{90}$Y, $^{99M}$Tc, $^{111}$In, $^{113M}$In, $^{123}$I, $^{125}$I, $^{18}$F, $^{86}$Y, $^{127}$Cs, $^{129}$Cs, $^{131}$I, $^{132}$I, $^{197}$Hg, $^{203}$Pb and $^{206}$Bi.

Radiolabels are conjugated to antibodies, peptides or mimetics by a variety of well-known techniques readily performed without undue experimentation by those having ordinary skill in the art. Radiolabels retain their radioactivity irrespective of conjugation. Conjugation may be accomplished directly between the antibody, peptide or mimetic and the radioisotope or linking, intermediate molecular groups may be provided between the antibody, peptide or mimetic and the radioisotope. Crosslinkers are particularly useful to facilitate conjugation by providing attachment sites for each moiety. Crosslinkers may include additional molecular groups which serve as spacers to separate the moieties from each other to prevent either from interfering with the activity of the other. Often imaging can be imaged using fluorescein, which are activated by light. (e.g. fluorescein (green), phycoerythrin (orange), P-E-cyanine-5 (red), P-E-texas red (red), cyanine-3 (orange), cyananine-5 (red), AMCA (ultraviolet detection)

One having ordinary skill in the art may conjugate an antibody, peptide or mimetic to a chemotherapeutic drug using well-known techniques. For example, Magerstadt, M. *Antibody Conjugates and Malignant Disease*. (1991) CRC Press, Boca Raton, USA, pp. 110-152) which is incorporated herein by reference, teaches the conjugation of various cytostatic drugs to amino acids of an antibody, peptide or to a mimetic. Such reactions may be applied to conjugate chemotherapeutic drugs to the antibody, peptide or mimetic. Antibodies such as peptides which have a free amino group may be conjugated to active agents at that group. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of a antibody of the invention.

Administration of Pharmaceutical Compositions

The dosage of the compositions of the present invention administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results. In some preferred embodiments, about 5 µg to 5000 mg of antibody, peptide or mimetic may be administered. In some preferred embodiments, 50 µg to 500 mg of antibody, peptide or mimetic may be administered. In other preferred embodiments, 500 µg to 50 mg of antibody, peptide or mimetic may be administered. In a still further preferred embodiment, 5 mg of antibody, peptide or mimetic is administered.

Compositions may be administered by an appropriate route such as, for example, by oral, intranasal, intramuscular, intraperitoneal or subcutaneous administration. In some embodiments, intravenous administration is preferred. In certain embodiments, the composition is administered by intraarterial, intradermal, parenteral, or intratumoral administration. According to some preferred embodiments, the individual has had surgery to remove bulk tumor mass prior to administration of the composition.

According to some embodiments of the invention, the pharmaceutical compositions are administered locally at the site of the tumor. In some embodiments, the pharmaceutical compositions are administered directly into the tumor cells and the tissue immediately surrounding the tumor. In some embodiment, the pharmaceutical compositions are delivered into brain tumors such as, for example, glioblastomas. In some embodiments, the pharmaceutical compositions are delivered into brain tumors as part of the surgical resection of the tumor. In some embodiment, the pharmaceutical compositions are delivered into brain tumors using stereotaxic surgical techniques.

Subsequent to initial administration, individuals may be boosted by readministration. In some preferred embodiments, multiple administrations are performed.

Dosage forms (composition) suitable for internal administration generally contain from about 1 milligram to about 500 milligrams of active ingredient per unit. In these pharmaceutical compositions the active ingredient will ordinarily be present in an amount of about 0.5-95% by weight based on the total weight of the composition.

Because conjugated antibody, peptide or mimetic are specifically targeted to cells with erbB, TNF, or IgSF receptors, conjugated antibody, peptide or mimetic which comprise chemotherapeutics or toxins are administered in doses less than those which are used when the chemotherapeutics or toxins are administered as unconjugated active agents, preferably in doses that contain up to 100 times less active agent. In some embodiments, conjugated antibody, peptide or mimetic which comprise chemotherapeutics or toxins are administered in doses that contain 10-100 times less active agent than the dosage of chemotherapeutics or toxins administered as unconjugated active agents. To determine the appropriate dose, the amount of antibody, peptide or mimetic is preferably measured in moles instead of by weight. In that way, the variable weight of different antibodies, peptides or mimetics does not affect the calculation. For example, presuming a one to one ratio of antibody to active agent in conjugated compositions of the invention, fewer moles of conjugated antibodies may be administered as compared to the moles of unconjugated antibodies administered, preferably up to 100 times less moles.

For parenteral administration, the antibody, peptide or mimetic can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field which is incorporated by reference in its entirety.

For example, a parenteral composition suitable for administration by injection is prepared by dissolving 1.5% by weight of active ingredient in 0.9% sodium chloride solution.

The antibody, peptide or mimetic may be administered to a tissue of an individual topically or by lavage. The antibodies, peptides or mimetics may be formulated as a cream, ointment, salve, douche, suppository or solution for topical administration or irrigation. Formulations for such routes administration of pharmaceutical compositions are well known.

The present invention is not intended to be limited by any theory. The present invention is further illustrated by the following examples, which are not intended to be limiting in any way.

EXAMPLES

Example 1

Dual-Specificity Receptor Specific Antibodies

EGFr and p185HER2/neu (erbB2) expressing cell lines, NE91 and T6-17 respectively, were used as immunogens to obtain cross-reactive Mab as described (Drebin et al, 1986). BALB/c (H-$2^d$) mice were immunized and then boosted intraperitoneally with 10⁷ NE91 cells. For the final boost, T6-17 cells were used instead of NE91 cells. Three days after the final boost, fusions were performed using spleen cells and the fusion partner Sp2/0-Ag14.

The supernatant from hybridoma were screened against the cell line used in the final boost by FACS analysis (FACScan, Becton-Dickinson) as described previously (Qian, et al., 1994). Colonies producing antibodies of the desired specificity were subcloned three times by limiting dilution. Isotypes were identified using the Mouse Monoclonal Antibody Subtyping Kit (Gibco BRL). The MAb are IgG1, IgG2a, or IgM subtype. Monoclonal hybridomas, 8A4(IgG1), A10A12 (IgM), 9G6(IgG2a,λ), 7H4, A10E9(IgM), A12D6(IgM), A6B12(IgM), A10E11 (IgM), B3G4(IgM), A5C7(IgM), 13A11 (IgM), 11C11 (IgM), and 13B11 (IgM) were tested in FACS analysis verifying their specificity against EGFR and p185her2 receptors on NE91 and T6-17 cells respectively. All antibodies were negative on the control $NR_6$ cell lines, which has no detectable expression of both receptors.

Monoclonal hybridomas 8A4 and A10A12 were deposited with the American Type Culture Collection (ATCC), 10801 University Blvd., Manassas, VA 20110-2209, USA, on Aug. 2, 2002 under the Budapest Treaty. Monoclonal hybridoma 8A4 was assigned accession number PTA-4565. Monoclonal hybridoma A10A12 was assigned accession number PTA-4566.

Figure 1B:
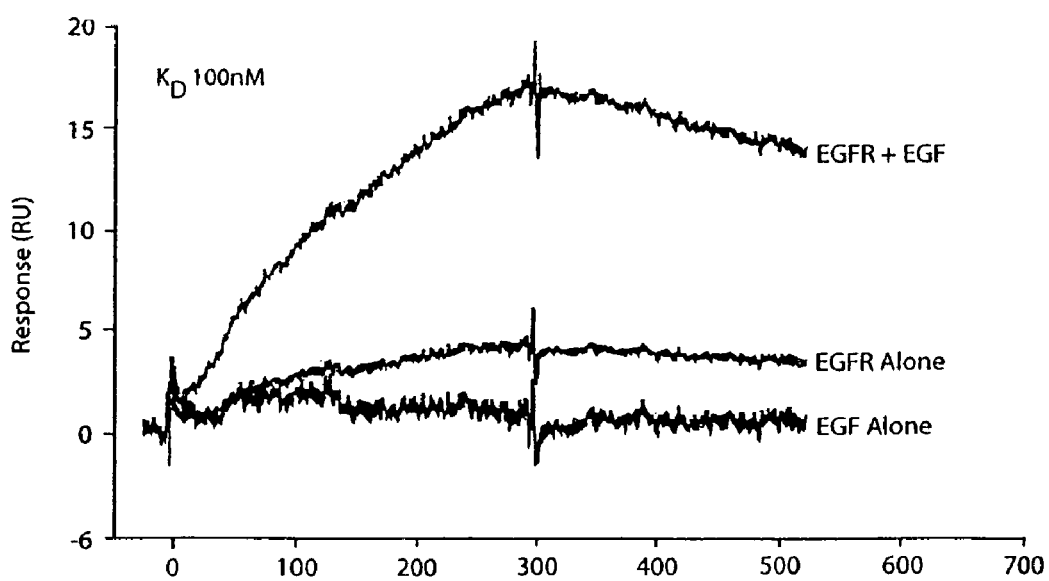

The cross-reactivity of 8A4 was characterized by surface plasmon resonance (Biacore). MAb 8A4 was immobilized and the binding of 8A4 to both p185neu-Fc and dimers and monomers of the EGFr ectodomains was studied. The dimers were created by adding EGF to EGFr monomers. MAb 8A4 bound to activated p185Her2/neu ($K_d$=53 nM) and dimeric EGFr ($K_d$=100 nM) with high affinity (FIGS. 1A and 1B.). MAb 8A4 did not bind detectably, however, to monomeric EGFr (FIG. 1B.).

In a separate experiment, cells of vulval carcinoma cell line A431 expressing EGFr were serum-starved for 24 hours before stimulation with 50 ng/ml of EGF. 10 min after EGF treatment, cells were harvested for FACS analysis, using MAb10A12 or control antibody that did not bind EGFr.

FACS analysis was performed as follows. Cells were washed with FACS buffer (cold PBS containing 0.5% Bovine Serum Albumin (BSA) and 0.1% sodium azide). 3×105 cells were then incubated with antibodies (0.5 µg/reaction) in a volume of 0.1 ml FACS buffer for 30 min at 4° C. Cells were washed by the FACS buffer again and the pellet was re-suspended. Cells were incubated with 0.5 microgram of FITC-conjugated rabbit anti-mouse IgG (or IgM for A10A12) in 0.1 ml of FACS buffer for another 30 minutes. Cells were washed and cell pellet was finally resuspended in 0.2 ml of FACS buffer and analyzed by flow cytometry (FACScan, Becton-Dickinson), as described previously (Qian, et al., 1994).

Significant binding of MAb10A12 over control antibody was detected for EGF-stimulated cells, but not over unstimulated cells.

The specificity of MAb8A4 for activated erbB family members was also tested by in an immunoprecipitation experiment. Briefly, subconfluent cells in 10-cm dishes cells were washed twice with cold PBS and solubilized with PI/RPA (1% Triton X-100, 1% deoxycholate, 0.1% SDS, 0.15 M NaCl, 0.01 M sodium phosphate-pH 7.4, 1% Aprotinin, 1 mM phenylmethysulfonyl fluoride, 2 mM EDTA, 10 mM Sodium Pyrophosphate, 400 mM Sodium orthovanadate, and 10 nM Iodoacetamide) buffer. Proteins were separated by 6% SDS-PAGE and transferred to nitrocellulose membranes (Nitrobind, MSI). Membranes were incubated overnight with the blocking buffer (0.5% non-fat milk and 5% goat serum in PBS). Anti-EGFr antibody (1005), antip185her2/neu antibody (C-18), and anti-phosphotyrosine antibody (pY99) were used for immunoblotting (Western blot) analysis. All antibodies were purchased from Santa Cruz Biotechnology. For use, antibodies were diluted 1:5000 in PBS containing 0.1% non-fat milk and 1% goat serum. After washing with PBST buffer, secondary HRP-conjugated antibodies (Boehringer Mannheim) were used at a 1:5000 dilution. Bands were visualized using ECL assay (Amersham).

Figure 2A:
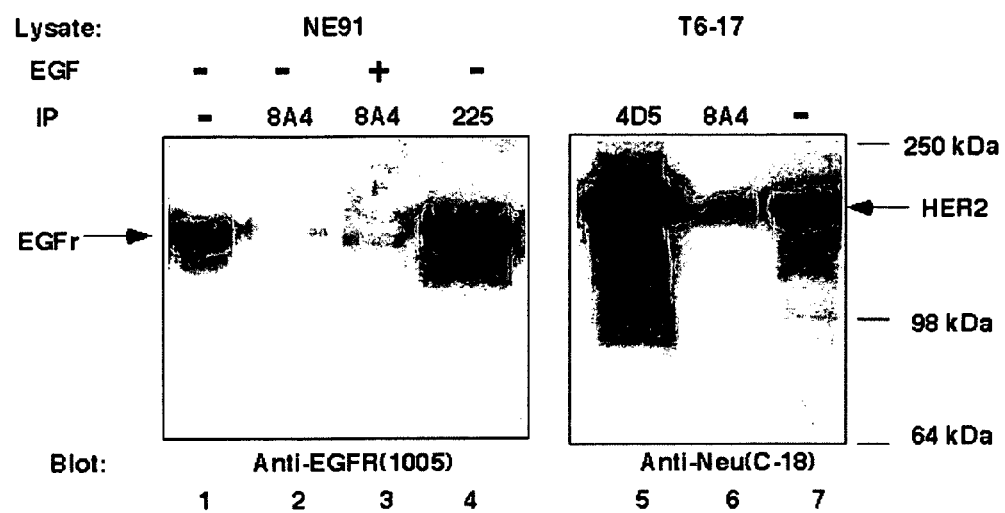
FIG. 2A-B depicts immunoprecipitation of EGFR and HER2 receptors by 8A4 from NE91 and T6-17 cells respectively. When NE91 is stimulated with EGF, the EGFR precipitated by 8A4 is highly tyrosine-phosphorylated as shown in B.
Figure 2B:
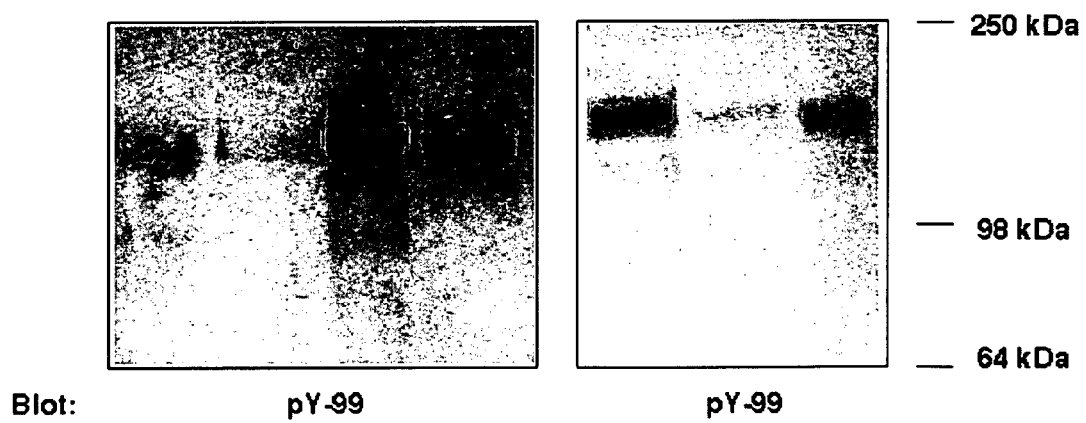

To test if 8A4 specifically binds to both p185 and EGFr, immunoprecipitation was performed on NE91 and T6-17 lysates. Results are shown in FIG. 2. Expression of EGFr and p185 was determined by loading extract directly, without immunoprecipitation (FIG. 2, lanes 1 and 7, respectively). 8A4 precipitated both EGFr (lane 2) and p185 (lane 6). Positive control MAbs 225 and 4D5 precipitated EGFr (lane 4) and p185 (lane 5) respectively. Consistent with FACS data, antibodies 225 and 4D5 precipitated a greater total amount of receptors than 8A4 (FIG. 2A). When NE91 cells were stimulated with EGF (100 ng/ml), however, the 8A4 was specific for EGFr bearing phosphotyrosine residue, compared to control antibody 225 (compare FIG. 2A and 2B).

The results describe herein indicate that Mab 8A4 and MAb10A12 bind specifically to activated erbB dimeric species.

Example 2

Biological Effects of Dual-Specificity Antibody

MTT Assay

MAb 8A4 biological activity was tested in the 3, (4,5-dimethylthiazol-2-yl)2,5-diphenyl-tetrazolium bromide) (MTT), which measures anchorage dependent cell growth (Hansen, et al., 1989

The MTT assay for measuring cell growth was performed as previously described in Hansen et al (J. Immunol. Methods 1989, 119, 203-210). Briefly, T6-17 cells were seeded in 96-well plates overnight in DMEM containing 10% FBS (1000 per well). T6-17 is derived from NIH3T3 by overexpressing the human erbB2 receptor. Cells were cultured in 100 µl of fresh medium containing 1 µg/ml of erbB peptides for 48 hours. This incubation time was preferred for measuring inhibitory effects of different analogs. No improvements in the inhibitory activity could be achieved by increasing the incubation period. 25 µl of MTT solution (5 mg/ml in PBS) were added to each well, and after 2 hours of incubation at 37° C., 100 µl of the extraction buffer (20% w/v of SDS, 50% N, N-dimethyl formamide, pH 4.7) were added. After an overnight incubation at 37° C., the optical density at 600 nm was measured using an ELISA reader.

The results of the MTT assay showed that MAb 8A4 was a potent an inhibitor of A431 cell growth, with an inhibitory potency comparable to control anti-EGFr (MAb 225) and anti-HER2/neu (5G3) antibodies.

In Vivo Assay

The inhibitory effect of 8A4 on tumor growth was compared to the inhibitory activity of 225 (anti EGFr) and 7.16.4 (anti-rat neu) in cells transformed by the action of heteromers of the EGFr and HER2/neu (according to the methods of Drebin et al, Oncogene, vol 2, pp 273-277, 1988). For in vivo growth effects, A431 (EGFr⁺, HER2/neu⁺), SKBR-3 (EGFr⁺, HER2/neu⁺), NE91 (EGFr⁺), and T6-17 (HER2/neu⁺) cells were used as representative erbB-transformed cell lines. Negative controls (erbB negative cell lines) included Ras transformed NIH3T3 and NR6 fibroblasts.

To analyze tumor growth in athymic mice, M1 cells (0.5× $10^6$) of each line were suspended in 0.1 ml of PBS and injected intradermally in the mid-dorsum of NCR nude mice. Antibodies or PBS control were injected twice weekly i.p. (10 µg each time). Tumor growth was monitored every 2-3 days up to 8 weeks. Tumor size was calculated by the formula: 3.14/6×(length×width×thickness).

Results showed that 8A4 treatment reduced the tumor growth of the M1 xenograft significantly. (FIG. 3.) M1 cells over-express both EGFr and p185. The in vivo tumorigenicity inhibition of 8A4 and 225 were comparable, although 225 has higher affinity for the EGFr than 8A4 in vitro. 7.16.4 demonstrated the greatest tumor growth inhibition, which is not a surprise considering that it was originally derived against the rat version of p185 that is expressed in the M1 cell.

Example 3

Creation of Mab Which Bind to Interaction Surfaces

MAb specific to dimerization domains are made from: (1) Recombinantly purified p185 subdomain IV fragment;(2) Improved S22-AFA analogs; and (3) other immunogens. Using both the subdomain IV fragment, and cysteine-knot peptides will yield high quality cross-reactive MAb. These species are used to immunize Balb/c mice to create a specific dimer surface inhibitory monoclonal species. S22-AFA is coupled to a carrier species as described previously (Jacob, et al, 1985; Williams, et al, 1989, J. Immunol.,142: 4392-4400; Christodoulides, et al, 1993, J. Genetic Microbiology, 139: 1729-1738). The subdomain IV fragment is used as is. Mab production employs a scheme described previously (Drebin, et al. 1986, Symp Fundam Cancer Res, 38:277-289; Drebin, et al. 1986, Proc Natl Acad Sci USA 83:9129-9133). Briefly, BALB/c ($H-2^d$) mice are immunized with 100 µg of S22-AFA species or soluble subdomain IV (in equal volumes of complete Freund's adjuvant) subcutaneously and then boosted 3 times intraperitoneally with 50 µg/injection. Three days after the final boost, fusions are performed using spleen cells and the fusion partner Sp2/0-Ag14. Screening of fusions will employ an ELISA with S22-AFA deposited in the wells. Other screening assays to be used include FACS analysis of T6-17 cells expressing HER2/neu.

MAb are generated and selected for their ability to bind S22-AFA peptide forms and to bind to Her2/neu on cells and are evaluated functionally in vitro in anchorage independent and dependent type studies. Specific binding to activated erbB complexes and ability to downregulate erbB activity are determined as described herein. Ability to limit the assembly of heterotetramers is determined specifically.

MAb are evaluated for in vivo effects on tumors using EGFr, Her2/neu, and EGFr and Her2/neu transformed cells (see above). 100 µg MAb is administered by intraperitoneal injection three times a week from the day of tumor xenograft. Injection of irrelevant anti-CD4 MAb or PBS serves as a control. Inhibiting the formation of oligomeric receptor forms will affect phenotype. The effect of co-treatment with doxorubicin/adriamycin which has been shown an increased effect on cells treated with antibodies (Park et al., Nat Biotechnol. 2000, 18, 194-198) is also examined. Tumor growth is monitored by volume measurement.

Example 4

Development of Cysteine Rich Domain (CRD) Reactive Monoclonal Antibodies

Cell lines transfected with erbB constructs are used as immunogens to create cysteine rich domain reactive MAb that are compared with the mimetics in terms of biological activity. NR6 cells transfected with pTex3-4, pTex4 and pTec6CN (See FIG. 3A and Kumagai et al, 2001) are used as immunogens. The fusion scheme is as described previously (Drebin, et al. 1986, Symp Fundam Cancer Res 38:277-289; Drebin, et al. 1986, Proc Natl Acad Sci USA 83:9129-9133). Briefly, BALB/c ($H-2^d$) mice are immunized with the cell line subcutaneously and then boosted 3 times intraperitoneally with $10^7$ cells. Three days after the final boost, fusions are performed using spleen cells and the fusion partner Sp2/0-Ag14. The SP2/0-Ag14 fusion partner secretes no free light chain. Hybridoma cell lines will be screened by FACS analysis against pNeu, pTex3, pTex3-4 (subdomains m and IV), pTex4 (subdomain IV only) and pTex6CN. Controls include NR6 cells, cells which express EGFr alone and pNex1, 2, and 3 (subdomains I, II, and III) and a cell line that expresses only subdomain I, pTex1 cells. Cell lines provide an unambiguous screening array for this class of MAb. Colonies producing antibodies of the desired specificity are subcloned three times by limiting dilution. Subtypes for MAb are identified using the Mouse Monoclonal Antibody Subtyping Kit (Gibco BRL).

Characterization of Cross-Reactive Monoclonal Antibodies

The similarity of many subdomains of the p185 and EGFr receptors is well known to those of ordinary skill in the art (Drebin, et al. 1984, Nature 312:545-8; Wada, et al. 1990, Cell, 61:1339-1347). These polypeptides often form transforming heteromeric complexes in human breast, pancreatic, and ovarian cancers. MAb reactive with each monomer have effects on tumors transformed by p185-EGFr ensembles. Adding multiple antibodies in vivo has a synergistic antitumor effect (Wada, et al. 1990a).

Other immunoglobulin structures share sufficient homology to be used as immunogens and include the following non-limiting examples: CTLA-4, CD28 and ICOS immunogens: CTLA-4: CKVELMYPPPYFVG-MGNGTQI--YVID-PEPC (SEQ ID NO:36); CD28: CKIEFMYPPPYLDNER-SNGTII--HIKEKHLC (SEQ ID NO:29); and ICOS: CSLSIFDPPPFQERNLSGG-YL--HIYESQLC (SEQ ID NO: 30).

As those skilled in the art will appreciate, numerous changes and modifications may be made to the preferred embodiments of the invention without departing from the spirit of the invention. It is intended that all such variations fall within the scope of the invention.

The entire disclosure of each patent, patent application, or other publication cited herein is hereby incorporated by reference.

LITERATURE CITED

O'Rourke, D. M., Qian, X., Zhang, H. -T., Nute, E., Meinkoth, J., and Greene, M. I. Trans receptor inhibition of human glioblastoma cells by erbB family ectodomains., Proc. Nat. Acad. Sci., 94(7), 3250-3255, 1997.

Qian, X., O'Rourke, D. M., Zhao, H., and Greene, M. I., Inhibition of p185$^{neu}$ kinase activity and cellular transformation by co-expression of a truncated neu protein. Oncogene, 13: 2149-2157, 1996.

Qian, X., O'Rourke, D. M., Drebin, J., Zhao, H., Wang, Q., and Greene, M. I.: Identification of p185 sequences required for monoclonal antibody- or ligand-mediated receptor signal attenuation. DNA, 16(12): 1395-1405, 1998.

Zhang, H. T., O'Rourke, D., Zhao, H., Murali, R., Mikami, Y., Davis, J. G., Greene, M. I., and Qian, X.: Absence of autophosphorylation site Y882 in the p185neu oncogene product correlates with a reduction of transforming potential. Oncogene, 16: 2835-2842, 1998.

O'Rourke, D., Nute, E. J. L., Davis, J. G., Wu, C., Lee, A., Murali, R., Zhang, H. T., Qian, X., Kao, C. C., Greene, M. I.: Inhibition of a naturally occurring EGFr oncoprotein by the p185neu ectodomain: implications for subdomain contributions to receptor assembly. Oncogene, 16: 1197-1207, 1998.

Qian, X., O'Rourke, D. M., Fei, Zhizhong, Zhang, H. T., Kao, C., Greene, M. I.: Domain-specific interactions between the p185 neu and EGF receptor kinases determine differential signaling outcomes. Journal of Biological Chemistry, 274: 574-583, 1999.

O'Rourke, D., Kao, G. D., Singh, N., Park, B., Muschel, R. J., Wu, C., Greene, M., Conversion of a radioresistant phenotype to a more sensitive one by disabling erbB receptor signaling in human cancer cells. Proc. Nat. Acad. Sci. (USA), 95: 10842-10847, 1998.

Peterson, N., and Greene, M. I. Bacterial Expression and Characterization of Recombinant Biologically-Active Anti-Tyrosine Kinase Receptor Antibody-Forms. DNA, 17: 1031-1040, 1998.

Park, B., O'Rourke, D., Wang, Q., Davis, J., Post, A. and Greene, M.I. Induction of the Tat-binding protein 1 gene accompanies the disabling of oncogenic erbB receptor tyrosine kinases. Proc. Nat. Acad. Sci. (USA), 96:6434-6438, 1999.

Wu, C., Chen, Z., Ullrich, A., Greene, M. I., and O'Rourke, D., Inhibition of EGFR-mediated phosphoinositide-3-OH kinase (PI3-K) signaling and glioblastoma phenotype by Signal-Regulatory Proteins (SIRPs). Oncogene, 19:3999-4010, 2000.

Park, B. W., Zhang, H. T., Wu, C., Berezov, A., Zhang, X., Dua, R., Wang, Q., Kao, G., O'Rourke, D., Greene, M. I. and Murali, R.: Rationally designed anti-HER2/neu peptide mimetic disablesp185$^{HER2/neu}$ tyrosine kinases in vitro and in vivo. Nature (*Biotechnology*), 18: 194-198, 2000.

Zhang, H., Wang, Q., Montone, K., Peavey, J., Drebin, J. A., Greene, M. I. and Murali, R.: Shared antigenic epitopes and pathobiological functions of anti-p185$^{her2/neu}$ monoclonal antibodies. Experimental and Molecular Pathology, 67:15-25, 1999.

Berezov A., Zhang H. T., Greene M. I. and Murali R. Disabling ErbB Receptors with Rationally Designed Exocyclic Mimetics of Antibodies: Structure-Function Analysis. Journal of Medicinal Chemistry, in press, 2001.

Kumagai T, Davis J G, Horie T, O'Rourke D and Greene M. I. The role of distinct p185 extracellular subdomains for dimerization with the epidermal growth factor receptor and EGF mediated signaling Proc. Nat. Acad. Sci. (USA), 98,5526-5531, 2001.

Zhang, H. T., Kacharmina, J. E., Miyashiro, K., Greene, M. I., and Eberwine, J. Protein Quantification from Complex Protein Mixtures Using a Novel Proteomics Methodology with Single Cell Resolution, Proc. Natl. Acad. Sci., 98,5497-5502, 2001.

Brennan, P. J., Kumagai, T., Berezov, A., Murali, R., and Greene, M. I. HER2/Neu: mechanisms of dimerization/oligomerization, Oncogene, 19: 6093-6101, 2000.

Alroy, I. & Yarden, Y. (1997) The ErbB signaling network in embryogenesis and oncogenesis: signal diversification through combinatorial ligand-receptor interactions *FEBS Lett* 410, 83-6.

Bach, A. C., Eyermann, C. J., Gross, J. D., Bowe, r. M. J., Harlow, R. L., Weber, P. C. & DeGrado, W. F. (1994) Structural Studies of a Family of High Affinity Ligands for GPIIb/IIIa *Journal of American Chemical Society* 116, 3207-3219.

Banner, D. W., D'Arcy, A., Janes, W., Gentz, R., Schoenfeld, H. J., Broger, C., Loetscher, H. & Lesslauer, W. (1993) Crystal structure of the soluble human 55 kd TNF receptor-human TNF beta complex: implications for TNF receptor activation *Cell* 73, 431-45.

Baselga, J., Norton, L., Albanell, J., Kim, Y. M. & Mendelsohn, J. (1998) Recombinant humanized anti-HER2 antibody (Herceptin) enhances the antitumor activity of paclitaxel and doxorubicin against HER2/neu overexpressing human breast cancer xenografts *Cancer Res* 58, 2825-2831.

Blain, S. W., Montalvo, E. & Massague, J. (1997) Differential interaction of the cyclin-dependent kinase (Cdk) inhibitor p27Kip1 with cyclin A-Cdk2 and cyclin D2-Cdk4 *J Biol Chem* 272, 25863-72.

Brennan, P. J., Kumogai, T., Berezov, A., Murali, R. & Greene, M. I. (2000) HER2/Neu: mechanism of dimerization/oligomerization *Oncogene* 19, 6093-6101.

Britsch, S., Li, L., Kirchhoff, S., Theuring, F., Brinkmann, V., Birchmeier, C. & Riethmacher, D. (1998) The ErbB2 and ErbB3 receptors and their ligand, neuregulin-1, are essential for development of the sympathetic nervous system *Genes Dev* 12, 1825-36.

Brown, V. I., Shah, N., Smith, R., Hellman, M., Jarett, L., Mikami, Y., Cohen, E., Qian, X. & Greene, M. I. (1994) Demonstration by two-color flow cytometry that tyrosine kinase activity is required for down-modulation of the oncogenic neu receptor *DNA Cell Biol* 13, 193-209.

Burgess, K., Li, W. & Lim, D. (1996) in *Solid phase syntheses of peptidomimetics.* (American Chemical Society, Washington, D, pp. ORGN-157.

Cambier, J. C. (1997) Inhibitory receptors abound? *Proc Natl Acad Sci USA* 94, 5993-5.

Carraway, K. L., 3rd & Cantley, L. C. (1994) A neu acquaintance for erbB3 and erbB4: a role for receptor heterodimerization in growth signaling *Cell* 78, 5-8.

Carter, P., Presta, L., Gorman, C. M., Ridgway, J. B., Henner, D., Wong, W. L., Rowland, A. M., Kotts, C., Carver, M. E. & Shepard, H. M. (1992) Humanization of an anti-p185HER2 antibody for human cancer therapy *Proceedings of the National Academy of Sciences of the United States of America* 89, 4285-9.

Chang, H., Riese, D. J., 2nd, Gilbert, W., Stern, D. F. & McMahan, U. J. (1997) Ligands for ErbB-family receptors encoded by a neuregulin-like gene *Nature* 387, 509-12.

Chiri, S., De Nadai, C. & Ciapa, B. (1998) Evidence for MAP kinase activation during mitotic division *J Cell Sci* 111, 2519-2527.

Chothia, C. & Lesk, A. M. (1987) Canonical structures for the hypervariable regions of immunoglobulins *J Mol Biol* 196, 901-17.

Christodoulides, M., McGuinness, B. T. & Heckels, J.E. (1993) Immunization with synthetic peptides containing epitopes of the class 1 outer-membrane protein of Neisseria meningitidis: production of bactericidal antibodies on immunization with a cyclic peptide *Journal of Genetic Microbiology* 139, 1729-1738.

D'Ambrosio, D., Fong, D. C. & Cambier, J. C. (1996) The SHIP phosphatase becomes associated with Fc gammaRIIB1 and is tyrosine phosphorylated during 'negative' signaling *Immunol Lett* 54, 77-82.

Dacron, M., Latour, S., Malbee, O., Espinosa, E., Pina, P., Pasmans, S. & Fridman, W. H. (1995) The same tyrosine-based inhibition motif, in the intracytoplasmic domain of Fc gamma RIIB, regulates negatively BCR-, TCR-, and FcR-dependent cell activation *Immunity* 3, 635-46.

Dahia, P. L., Aguiar, R. C., Honegger, J., Fahlbush, R., Jordan, S., Lowe, D. G., Lu, X., Clayton, R. N., Besser, G. M. & Grossman, A. B. (1998) Mutation and expression analysis of the p27/kip1 gene in corticotrophin secreting tumors *Oncogene* 16, 69-76.

Deb, T. B., Wong, L., Salomon, D. S., Zhou, G., Dixon, J. E., Gutkind, J. S., Thompson, S. A. & Johnson, G. R. (1998a) A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation *J Biol Chem* 273, 16643-6.

Deb, T. B., Wong, L., Salomon, D. S., Zhou, G., Dixon, J. E., Gutkind, J. S., Thompson, S. A. & Johnson, G. R. (1998b) A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation *J Biol Chem* 273, 16643-16646.

Deveraux, Q. L., Takahashi, R., Salvesen, G. S. & Reed, J. C. (1997) X-linked IAP is a direct inhibitor of cell-death proteases *Nature* 388, 300-4.

Di Cristofano, A., Kotsi, P., Peng, Y. F., Cordon-Cardo, C., Elkon, K. B. & Pandolfi, P. P. (1999) Impaired Fas response and autoimmunity in Pten+/− mice *Science* 285, 2122-5.

Di Cristofano, A. & Pandolfi, P. P. (2000) The multiple roles of PTEN in tumor suppression *Cell* 100, 387-90.

Dougall, W. C., Qian, X., Peterson, N. C., Miller, M. J., Samanta, A. & Greene, M. I. (1994) The neu-oncogene: signal transduction pathways, transformation mechanisms and evolving therapies *Oncogene* 9, 2109-2123.

Drebin, J. A., Link, V. C. & Greene, M. I. (1988) Monoclonal antibodies reactive with distinct domains of the neu oncogene-encoded p185 molecule exert synergistic anti-tumor effects in vivo *Oncogene* 2, 273-277.

Drebin, J. A., Link, V. C., Stern, D. F., Weinberg, R. A. & Greene, M. I. (1985) Down-modulation of an oncogene protein product and reversion of the transformed phenotype by monoclonal antibodies *Cell* 41, 697-706.

Drebin, J. A., Link, V. C., Stem, D. F., Weinberg, R. A. & Greene, M. I. (1986a) Development of monoclonal antibodies reactive with the product of the neu oncogene *Symp Fundam Cancer Res* 38, 277-289.

Drebin, J. A., Link, V. C., Weinberg, R. A. & Greene, M. I. (1986b) Inhibition of tumor growth by a monoclonal antibody reactive with an oncogene-encoded tumor antigen *The Proceedings of the National Academy of Science USA* 83, 9129-9133.

Drebin, J. A., Stern, D. F., Link, V. C., Weinberg, R. A. & Greene, M. I. (1984) Monoclonal antibodies identify a cell-surface antigen associated with an activated cellular oncogene *Nature* 312, 545-548.

Dudek, H., Datta, S. R., Franke, T. F., Birnbaum, M. J., Yao, R., Cooper, G. M., Segal, R. A., Kaplan, D. R. & Greenberg, M. E. (1997) Regulation of neuronal survival by the serine-threonine protein kinase Akt *Science* 275, 661-5.

Eck, M. J. & Sprang, S. R. (1989) The structure of tumor necrosis factor-alpha at 2.6 A resolution. Implications for receptor binding *J Biol Chem* 264, 17595-605.

Eck, M. J., Ultsch, M., Rinderknecht, E., de Vos, A. M. & Sprang, S. R. (1992) The structure of human lymphotoxin (tumor necrosis factor-beta) at 1.9—A resolution *J Biol Chem* 267, 2119-22.

Eigenbrot, C., Gonzalez, T., Mayeda, J., Carter, P., Werther, W., Hotaling, T., Fox, J. & Kessler, J. (1994) X-ray structures of fragments from binding and nonbinding versions of a humanized anti-CD18 antibody: structural indications of the key role of VH residues 59 to 65 *Proteins* 18, 49-62.

Eigenbrot, C., Randal, M., Presta, L., Carter, P. & Kossiakoff, A. A. (1993) X-ray structures of the antigen-binding domains from three variants of humanized anti-p185HER2 antibody 4D5 and comparison with molecular modeling *J Mol Biol* 229, 969-995.

Erickson, S. L., O'Shea, K. S., Ghaboosi, N., Loverro, L., Frantz, G., Bauer, M., Lu, L. H. & Moore, M. W. (1997) ErbB3 is required for normal cerebellar and cardiac development: a comparison with ErbB2-and heregulin-deficient mice *Development* 124, 4999-5011.

Feng, G. S. (1999) Shp-2 tyrosine phosphatase: signaling one cell or many *Exp Cell Res* 253, 47-54.

Ferguson, K. M., Darling, P. J., Mohan, M. J., Macatee, T. L. & Lemmon, M. A. (2000) Extracellular domains drive homo- but not hetero-dimerization of erbB receptors *Embo J* 19, 4632-43.

Fujioka, Y., Matozaki, T., Noguchi, T., Iwamatsu, A., Yamao, T., Takahashi, N., Tsuda, M., Takada, T. & Kasuga, M. (1996) A novel membrane glycoprotein, SHPS-1, that binds the SH2-domain-containing protein tyrosine phosphatase SHP-2 in response to mitogens and cell adhesion *Molecular and Cellular Biology* 16, 6887-99.

Fumari, F. B., Huang, H. J. & Cavenee, W. K. (1998) The phosphoinositol phosphatase activity of PTEN mediates a serum- sensitive G1 growth arrest in glioma cells *Cancer Res* 58, 5002-8.

Fumari, F. B., Lin, H., Huang, H. S. & Cavenee, W. K. (1997) Growth suppression of glioma cells by PTEN requires a functional phosphatase catalytic domain *Proc Natl Acad Sci USA* 94, 12479-84.

Garrett, T. P., McKern, N. M., Lou, M., Frenkel, M. J., Bentley, J. D., Lovrecz, G. O., Elleman, T. C., Cosgrove, L. J. & Ward, C. W. (1998a) Crystal structure of the first three domains of the type-1 insulin-like growth factor receptor *Nature* 394, 395-9.

Garrett, T. P., McKern, N. M., Lou, M., Frenkel, M. J., Bentley, J. D., Lovrecz, G. O., Elleman, T. C., Cosgrove, L. J. & Ward, C. W. (1998b) Crystal structure of the first three domains of the type-1 insulin-like growth factor receptor *Nature* 394, 395-399.

Gasparini, G., Gullick, W. J., Bevilacqua, P., Sainsbury, J. R. C., Meli, S., Boracchi, P., Testolin, A., Lamalfa, G. & Pozza, F. (1992) Human Breast Cancer—Prognostic Significance of the c-erbB-2 Oncoprotein Compared with Epidermal Growth Factor Receptor, DNA Ploidy, and Conventional Pathologic Features *Journal of Clinical Oncology* 10, 686-695.

Goodman, M. & Shao, H. (1996) Peptidomimetic building blocks for drug discovery: an overview *Pure Appl. Chem.* 68, 1303-1308.

Hanessian, S., Mcnaughton-Smith, G., Lombart, H.-G. & Lubell, W. D. (1997) Design and synthesis of conformationally constrained amino acids as versatile scaffolds and peptide mimetics *Tetrahedron* 53, 12789-12854.

Hemmings, B. A. (1997) Akt signaling: linking membrane events to life and death decisions *Science* 275, 628-630.

Huang, G. C., Ouyang, X. & Epstein, R. J. (1998) Proxy activation of protein ErbB2 by heterologous ligands implies a heterotetrameric mode of receptor tyrosine kinase interaction *Biochem J* 331, 113-119.

Huang, H. S., Nagane, M., Klingbeil, C. K., Lin, H., Nishikawa, R., Ji, X. D., Huang, C. M., Gill, G. N., Wiley, H. S. & Cavenee, W. K. (1997) The enhanced tumorigenic activity of a mutant epidermal growth factor receptor common in human cancers is mediated by threshold levels of constitutive tyrosine phosphorylation and unattenuated signaling *J Biol Chem* 272, 2927-35.

Irmler, M., Thome, M., Hahne, M., Schneider, P., Hoffmann, K., Steiner, V., Bodmer, J. L., Schroter, M., Burns, K., Mattmann, C., Rimoldi, D., French, L. E. & Tschopp, J. (1997) Inhibition of death receptor signals by cellular FLIP [see comments] *Nature* 388, 190-5.

Jackson, S., Harlow, R., Dwivedi, A., Parthasarathy, A., Higley, A., Krywko, J., Rockwell, A., Markwalder, J., Wells, G., Wexler, R., Mousa, S. & DeGrado, W. F. (1994) Template-constrained cyclic peptides: design of high-affinity ligands for GPIIb/IIIa *Journal of American Chemical Society* 116, 3220-3230.

Jardines, L., Weiss, M., Fowble, B. & Greene, M. (1993) neu(c-erbB-2/HER2) and the epidermal growth factor receptor (EGFR) in breast cancer *Pathobiology* 61, 268-82.

Jacob, C. O., Leitner, M., Zamir, A., Salomon, D. & Arnon, R. (1985) Priming immunization against cholera toxin and *E. coli* heat-labile toxin by a cholera toxin short peptide-beta-galactosidase hybrid synthesized in *E. coli Embo Journal* 4, 3339-3343.

Kauffinann-Zeh, A., Rodriguez-Viciana, P., Ulrich, E., Gilbert, C., Coffer, P., Downward, J. & Evan, G. (1997) Suppression of c-Myc-induced apoptosis by Ras signaling through PI(3)K and PKB *Nature* 385, 544-8.

Kharitonenkov, A., Chen, Z., Sures, I., Wang, H., Schilling, J. & Ullrich, A. (1997) A family of proteins that inhibit signalling through tyrosine kinase receptors *Nature* 386, 181-6.

KieberEmmons, T., Murali, R. & Greene, M. I. (1997) Therapeutic peptides and peptidomimetics *Curr. Opin. Biotechnol.* 8, 435-441.

Kokai, Y., Cohen, J. A., Drebin, J. A. & Greene, M. I. (1987) Stage- and tissue-specific expression of the neu oncogene in rat development *Proc Natl Acad Sci USA* 84, 8498-8501.

Kokai, Y., Myers, J. N., Wada, T., Brown, V. I., LeVea, C. M., Davis, J. G., Dobashi, K. & Greene, M. I. (1989) Synergistic Interaction of p185c-neu and the EGF Receptor Leads to Transformation of Rodent Fibroblasts *Cell* 58, 287-292.

Koskinen, A. M. P. & Hassila, H. (1996) Asymmetric intramolecular cyclopropanation. Synthesis of conformationally constrained aminocyclopropane carboxylic acids *Acta Chem. Scand.* 50, 323-327.

Kramer, R., Bucay, N., Kane, D. J., Martin, L. E., Tarpley, J. E. & Theill, L. E. (1996) Neuregulins with an Ig-like domain are essential for mouse myocardial and neuronal development *Proc Natl Acad Sci USA* 93, 4833-8.

Kuhn, C., Lindeberg, G., Gogoll, A., Hallberg, A. & Schmidt, B. (1997) Fmoc protected peptide mimetic based on a cyclohexane framework and incorporation into angiotensin II *Tetrahedron* 53, 12497-12504.

Kumagai, T., Davis, J. G., Horie, T., O'Rourke, D. M. & Greene, M. I. (2001) The role of distinct p185neu extracellular subdomains for dimerization with the epidermal growth factor (EGF) receptor and EGF-mediated signaling *Proc Natl Acad Sci USA* 98, 5526-31.

Lee, C. C., Ichihara, T., Yamamoto, S., Wanibuchi, H., Sugimura, K., Wada, S., Kishimoto, T. & Fukushima, S. (1999) Reduced expression of the CDK inhibitor p27(KIP1) in rat two-stage bladder carcinogenesis and its association with expression profiles of p21(WAF1/Cip1) and p53 *Carcinogenesis* 20, 1697-1708.

Lee, K. F., Simon, H., Chen, H., Bates, B., Hung, M. C. & Hauser, C. (1995) Requirement for neuregulin receptor erbB2 in neural and cardiac development *Nature* 378, 394-8.

Lees, E. (1995) Cyclin dependent kinase regulation *Curr Opin Cell Biol* 7, 773-80.

Li, F., Ambrosini, G., Chu, E. Y., Plescia, J., Tognin, S., Marchisio, P. C. & Altieri, D. C. (1998) Control of apoptosis and mitotic spindle checkpoint by survivin *Nature* 396, 580-4.

Li, J., Yen, C., Liaw, D., Podsypanina, K., Bose, S., Wang, S. I., Puc, J., Miliaresis, C., Rodgers, L., McCombie, R., Bigner, S. H., Giovanella, B. C., Ittmann, M., Tycko, B., Hibshoosh, H., Wigler, M. H. & Parsons, R. (1997) PTEN, a putative protein tyrosine phosphatase gene mutated in human brain, breast, and prostate cancer *Science* 275, 1943-7.

Liu, X., Hwang, H., Cao, L., Buckland, M., Cunningham, A., Chen, J., Chien, K. R., Graham, R. M. & Zhou, M. (1998) Domain-specific gene disruption reveals critical regulation of neuregulin signaling by its cytoplasmic tail *Proc Natl Acad Sci USA* 95, 13024-9.

Lu, Y., Lin, Y. Z., LaPushin, R., Cuevas, B., Fang, X., Yu, S. X., Davies, M. A., Khan, H., Furui, T., Mao, M., Zinner, R., Hung, M. C., Steck, P., Siminovitch, K. & Mills, G. B. (1999) The PTEN/MMAC1/TEP tumor suppressor gene decreases cell growth and induces apoptosis and anoikis in breast cancer cells *Oncogene* 18, 7034-45.

MacCallum, R. M., Martin, A. C. & Thornton, J. M. (1996) Antibody-antigen interactions: contact analysis and binding site topography *J Mol Biol* 262, 732-45.

Magliani, W., Conti, S., de Bernardis, F., Gerloni, M., Bertolotti, D., Mozzoni, P., Cassone, A. & Polonelli, L. (1997) Therapeutic potential of antiidiotypic single chain antibodies with yeast killer toxin activity *Nat Biotechnol* 15, 155-8.

McIntyre, M., Desdouets, C., C, S. n.-B., Laurent-Winter, C., Lamas, E. & Br chot, C. (1999) Differential expression of the cyclin-dependent kinase inhibitor P27 in primary hepatocytes in early-mid G1 and G1/S transitions *Oncogene* 18, 4577-85.

Meyer, D. & Birchmeier, C. (1995) Multiple essential functions of neuregulin in development *Nature* 378, 386-90.

Moore, G. J. (1994) Designing peptide mimetics *Trends Pharmacol Sci* 15, 124-129.

Moscatello, D. K., Holgado-Madruga, M., Emlet, D. R., Montgomery, R. B. & Wong, A. J. (1998) Constitutive activation of phosphatidylinositol 3-kinase by a naturally occurring mutant epidermal growth factor receptor *J Biol Chem* 273, 200-6.

Murali, R., Brennan, P. J., KieberEmmons, T. & Greene, M. I. (1996a) Structural analysis of p185(c-neu) and epidermal growth factor receptor tyrosine kinases: Oligomerization of kinase domains *Proceedings of the National Academy of Sciences of the United States of America* 93, 6252-6257.

Murali, R., Brennan, P. J., KieberEmmons, T. & Greene, M. I. (1996b) Structural analysis of p185(c-neu) and epidermal growth factor receptor tyrosine kinases: Oligomerization of kinase domains *Proc. Natl. Acad. Sci. U.S.A.* 93, 6252-6257.

Murali, R. & Greene, M. I. (1998) Structure-based design of immunologically active therapeutic peptides *Immunol Res* 17, 163-169.

Myers, M. P., Pass, I., Batty, I. H., Van der Kaay, J., Stolarov, J. P., Hemmings, B. A., Wigler, M. H., Downes, C. P. & Tonks, N. K. (1998) The lipid phosphatase activity of PTEN is critical for its tumor supressor function *Proc Natl Acad Sci USA* 95, 13513-8.

Myers, M. P. & Tonks, N. K. (1997) PTEN: sometimes taking it off can be better than putting it on *Am J Hum Genet* 61, 1234-8.

Nagane, M., Coufal, F., Lin, H., Bogler, O., Cavenee, W. K. & Huang, H. J. (1996) A common mutant epidermal growth factor receptor confers enhanced tumorigenicity on human glioblastoma cells by increasing proliferation and reducing apoptosis *Cancer Res* 56, 5079-86.

Nagane, M., Levitzki, A., Gazit, A., Cavenee, W. K. & Huang, H. J. (1998) Drug resistance of human glioblastoma cells conferred by a tumor-specific mutant epidermal growth factor receptor through modulation of Bcl-XL and caspase-3-like proteases *Proc Natl Acad Sci USA* 95, 5724-9.

Naismith, J. H., Devine, T. Q., Brandhuber, B. J. & Sprang, S. R. (1995) Crystallographic evidence for dimerization of unliganded tumor necrosis factor receptor *J Biol Chem* 270, 13303-13307.

Naismith, J. H. & Sprang, S. R. (1998) Modularity in the TNF-receptor family *Trends Biochem Sci* 23, 74-9.

Nayak, B. P., Tuteja, R., Manivel, V., Roy, R. P., Vishwakarma, R. A. & Rao, K. V. (1998) B cell responses to a peptide epitope. V. Kinetic regulation of repertoire discrimination and antibody optimization for epitope *J Immunol* 161, 3510-3519.

Nishikawa, R., Ji, X. D., Harmon, R. C., Lazar, C. S., Gill, G. N., Cavenee, W. K. & Huang, H. J. (1994) A mutant epidermal growth factor receptor common in human glioma confers enhanced tumorigenicity *Proc Natl Acad Sci USA* 91, 7727-31.

O'Rourke, D. M., Kao, G. D., Singh, N., Park, B. W., Muschel, R. J., Wu, C. J. & Greene, M. I. (1998) Conversion of a radioresistant phenotype to a more sensitive one by disabling erbB receptor signaling in human cancer cells *Proc Natl Acad Sci USA* 95, 10842-7.

O'Rourke, D. M., Qian, X., Zhang, H. T., Davis, J. G., Nute, E., Meinkoth, J. & Greene, M. I. (1997) Trans receptor inhibition of human glioblastomacells by erbB family ectodomains *Proc Natl Acad Sci USA* 94, 3250-5.

Pages, P., Benali, N., Saint-Laurent, N., Esteve, J. P., Schally, A. V., Tkaczuk, J., Vaysse, N., Susini, C. & Buscail, L. (1999) sst2 somatostatin receptor mediates cell cycle arrest and induction of p27(Kip1). Evidence for the role of SHP-1 *J Biol Chem* 274, 15186-93.

Park, B. W., Zhang, H. T., Wu, C., Berezov, A., Zhang, X., Dua, R., Wang, Q., Kao, G., O'Rourke, D. M., Greene, M. I. & Murali, R. (2000) Rationally designed anti-HER2/neu peptide mimetic disables P185HER2/neu tyrosine kinases in vitro and in vivo *Nat. Biotechnol.* 18, 194-198.

Patel, G., Husman, W., Jehanli, A. M., Deadman, J. J., Green, D., Kakkar, V. V. & Brennand, D. M. (1999) A cyclic peptide analogue of the loop III region of platelet-derived growth factor-BB is a synthetic antigen for the native protein *J Pept Res* 53, 68-74.

Pegram, M. D., Lipton, A., Hayes, D. F., Weber, B. L., Baselga, J. M., Tripathy, D., Baly, D., Baughman, S. A., Twaddell, T., Glaspy, J. A. & Slamon, D. J. (1998) Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment *Journal of Clinical Oncology* 16, 2659-2671.

Pianetti, S., Arsura, M., Romieu-Mourez, R., Coffey, R. J. & Sonenshein, G. E. (2001) Her-2/neu overexpression induces NF-kappaB via a P13-kinase/Akt pathway involving calpain-mediated degradation of IkappaB-alpha that can be inhibited by the tumor suppressor PTEN *Oncogene* 20, 1287-99.

Pinkas-Kramarski, R., Eilam, R., Alroy, I., Levkowitz, G., Lonai, P. & Yarden, Y. (1997) Differential expression of NDF/neuregulin receptors ErbB-3 and ErbB-4 and involvement in inhibition of neuronal differentiation *Oncogene* 15, 2803-2815.

Pinkas-Kramarski, R., Soussan, L., Waterman, H., Levkowitz, G., Alroy, I., Klapper, L., Lavi, S., Seger, R., Ratzkin, B. J., Sela, M. & Yarden, Y. (1996) Diversification of Neu differentiation factor and epidermal growth factor signaling by combinatorial receptor interactions *Embo J* 15, 2452-67.

Posthumus, W. P., Lenstra, J. A., van Nieuwstadt, A. P., Schaaper, W. M., van der Zeijst, B. A. & Meloen, R. H. (1991) Immunogenicity of peptides simulating a neutralization epitope of transmissible gastroenteritis virus *Virology* 182, 371-375.

Qian, X., Dougall, W. C., Fei, Z. & Greene, M. I. (1995) Intermolecular association and trans-phosphorylation of different neu-kinase forms permit SH2-dependent signaling and oncogenic transformation *Oncogene* 10, 211-219.

Qian, X., Dougall, W. C., Hellman, M. E. & Greene, M. I. (1994a) Kinase-deficient neu proteins suppress epidermal growth factor receptor function and abolish cell transformation *Oncogene*.

Qian, X., LeVea, C. M., Freeman, J. K., Dougall, W. C. & Greene, M. I. (1994b) Heterodimerization of epidermal growth factor receptor and wild-type or kinase-deficient Neu: A mechanism of interreceptor kinase activation and transphosphorylation *The Proceedings of the National Academy of Science USA* 91, 1500-1504.

Qian, X., O'Rourke, D. M., Fei, Z., Kao, C.-C., Zhang, H.-T. & Greene, M. I. (1998) Domain-specific interactions between the p185neu and EGF receptor kinases determine differential signalling outcomes. *J Biol Chem*.

Qian, X., O'Rourke, D. M., Fei, Z., Zhang, H. T., Kao, C. C. & Greene, M. I. (1999) Domain-specific interactions between the p185(neu) and epidermal growth factor receptor kinases determine differential signaling outcomes *J Biol Chem* 274, 574-83.

Riese, D. J., 2nd, Komurasaki, T., Plowman, G. D. & Stern, D. F. (1998) Activation of ErbB4 by the bifunctional epidermal growth factor family hormone epiregulin is regulated by ErbB2 *J Biol Chem* 273, 11288-94.

Riethmacher, D., Sonnenberg-Riethmacher, E., Brinkmann, V., Yamaai, T., Lewin, G. R. & Birchmeier, C. (1997) Severe neuropathies in mice with targeted mutations in the ErbB3 receptor *Nature* 389, 725-30.

Saragovi, H. U. & Greene, M. I. (1992) Constrained peptides and mimetics as probes of protein secondary structures. *Immunomethods* 1, 5-9.

Saxton, T. M., Henkemeyer, M., Gasca, S., Shen, R., Rossi, D. J., Shalaby, F., Feng, G. S. & Pawson, T. (1997) Abnormal mesoderm patterning in mouse embryos mutant for the SH2 tyrosine phosphatase Shp-2 *Embo J* 16, 2352-64.

Schechter, A. L., Stern, D. F., Vaidyanathan, L., Decker, S. J., Drebin, J. A., Greene, M. I. & Weinberg, R. A. (1984) The neu oncogene: an erb-B-related gene encoding a 185,000-Mr tumour antigen *Nature* 312, 513-516.

Schmidt, M. & Wels, W. (1996) Targeted inhibition of tumour cell growth by a bispecific single-chain toxin containing an antibody domain and TGF alpha *Br J Cancer* 74, 853-862.

Shayesteh, L., Lu, Y., Kuo, W. L., Baldocchi, R., Godfrey, T., Collins, C., Pinkel, D., Powell, B., Mills, G. B. & Gray, J. W. (1999) PIK3CA is implicated as an oncogene in ovarian cancer *Nat Genet* 21, 99-102.

Shi, Z. Q., Lu, W. & Feng, G. S. (1998) The Shp-2 tyrosine phosphatase has opposite effects in mediating the activation of extracellular signal-regulated and c-Jun NH2-terminal mitogen-activated protein kinases *J Biol Chem* 273, 4904-8.

Shi, Z. Q., Yu, D. H., Park, M., Marshall, M. & Feng, G. S. (2000) Molecular mechanism for the Shp-2 tyrosine phosphatase function in promoting growth factor stimulation of Erk activity *Molecular and Cellular Biology* 20, 1526-36.

Stambolic, V., Suzuki, A., de la Pompa, J. L., Brothers, G. M., Mirtsos, C., Sasaki, T., Ruland, J., Penninger, J. M., Siderovski, D. P. & Mak, T. W. (1998) Negative regulation of PKB/Akt-dependent cell survival by the tumor suppressor PTEN *Cell* 95, 29-39.

Steck, P. A., Pershouse, M. A., Jasser, S. A., Yung, W. K., Lin, H., Ligon, A. H., Langford, L. A., Baumgard, M. L., Hattier, T., Davis, T., Frye, C., Hu, R., Swedlund, B., Teng, D. H. & Tavtigian, S. V. (1997) Identification of a candidate tumour suppressor gene, MMAC1, at chromosome 10q23.3 that is mutated in multiple advanced cancers *Nat Genet* 15, 356-62.

Sun, D., Whitaker, J. N., Cao, L., Han, Q., Sun, S., Coleclough, C., Mountz, J. & Zhou, T. (1998) Cell death mediated by Fas-FasL interaction between glial cells and MBP-reactive T cells *J Neurosci Res* 52, 458-467.

Takada, T., Matozaki, T., Takeda, H., Fukunaga, K., Noguchi, T., Fujioka, Y., Okazaki, I., Tsuda, M., Yamao, T., Ochi, F. & Kasuga, M. (1998) Roles of the complex formation of SHPS-1 with SHP-2 in insulin-stimulated mitogen-activated protein kinase activation *J Biol Chem* 273, 9234-42.

Takasaki, W., Kajino, Y., Kajino, K., Murali, R. & Greene, M. I. (1997) Structure-based design and characterization of exocyclic peptidomimetics that inhibit TNF alpha binding to its receptor *Nature Biotechnology* 15, 1266-1270.

Tamura, M., Gu, J., Matsumoto, K., Aota, S., Parsons, R. & Yamada, K. M. (1998) Inhibition of cell migration, spreading, and focal adhesions by tumor suppressor PTEN *Science* 280, 1614-7.

Tonks, N. K. & Myers, M. P. (1999) Structural assets of a tumor suppressor *Science* 286, 2096-7.

Tzahar, E. & Yarden, Y. (1998) The ErbB-2/HER2 oncogenic receptor of adenocarcinomas: from orphanhood to multiple stromal ligands *Biochim Biophys Acta* 1377, M25-37.

Valero, M. L., Camarero, J. A., Adeva, A., Verdaguer, N., Fita, I., Mateu, M. G., Domingo, E., Giralt, E. & Andreu, D. (1995) Cyclic peptides as conformationally restricted models of viral antigens: application to foot-and-mouth disease virus *Biomed Pept Proteins Nucleic Acids* 1, 133-140.

van der Werf, S., Briand, J. P., Plaue, S., Burckard, J., Girard, M. & Van Regenmortel, M. H. (1994) Ability of linear and cyclic peptides of neutralization antigenic site 1 of poliovirus type 1 to induce virus cross-reactive and neutralizing antibodies *Res Virol* 145, 349-359.

Van Regenmortel, M. H. (1989) Structural and functional approaches to the study of protein antigenicity *Immunol Today* 10, 266-272.

Van Regenmortel, M. H. V. (1996) Mapping Epitope Structure and Activity: From One-Dimensional Prediction to Four-Dimensional Description of Antigenic Specificity *Methods* 9, 465-472.

Veillette, A., Thibaudeau, E. & Latour, S. (1998) High expression of inhibitory receptor SHPS-1 and its association with protein-tyrosine phosphatase SHP-1 in macrophages *J Biol Chem* 273, 22719-28.

Vita, C., Vizzavona, J., Drakopoulou, E., Zinn-Justin, S., Gilquin, B. & Menez, A. (1998) Novel miniproteins engineered by the transfer of active sites to small natural scaffolds *Biopolymers* 47, 93-100.

Vogelstein, B., Lane, D. & Levine, A. J. (2000) Surfing the p53 network *Nature* 408, 307-10.

Voice, J. K., Klemke, R. L., Le, A. & Jackson, J. H. (1999) Four human ras homologs differ in their abilities to activate Raf-1, induce transformation, and stimulate cell motility *J Biol Chem* 274, 17164-70.

Wada, T., Myers, J. N., Kokai, Y., Brown, V. I., Hamuro, J., LeVea, C. M. & Greene, M. I. (1990a) Anti-receptor antibodies reverse the phenotype of the cells transformed by two interacting proto-oncogene encoded receptor proteins *Oncogene* 5, 489-495.

Wada, T., Qian, X. L. & Greene, M. I. (1990b) Intermolecular Association of the P185Neu Protein and EGF Receptor Modulates EGF Receptor Function *Cell* 61, 1339-1347.

Waid, P. P., Flynn, G. A., Huber, E. W. & Sabol, J. S. (1996) Constrained amino acids. An approach to the synthesis of 3-substituted prolines *Tetrahedron Lett.* 37, 4091-4094.

Ward, C. W., Hoyne, P. A. & Flegg, R. H. (1995) Insulin and epidermal growth factor receptors contain the cysteine repeat motif found in the tumor necrosis factor receptor *Proteins* 22, 141-153.

Williams, W. V., London, S. D., Weiner, D. B., Wadsworth, S., Berzofsky, A., Robey, F. Rubin, D. H. & Greene, M. I. (1989) Immune response to a molecularlydefined internal image idiotype *Journal of Immunology* 142, 4392-4400.

Wong, A. J., Ruppert, J. M., Bigner, S. H., Grzeschik, C. H., Humphrey, P. A., Bigner, D. S. & Vogelstein, B. (1992) Structural alterations of the epidermal growth factor receptor gene in human gliomas *Proc Natl Acad Sci USA* 89, 2965-9.

Worthylake, R., Opresko, L. K. & Wiley, H. S. (1999) ErbB-2 amplification inhibits down-regulation and induces constitutive activation of both ErbB-2 and epidermal growth factor receptors *J Biol Chem* 274, 8865-8874.

Wu, C., Chen, Z., Ullrich, A., Greene, M. I. & O'Rourke, D. (1999) Diminished signaling from transforming erbB receptors involves MAPK-independent activation of signal-regulatory proteins (SIRPs/SHPS-1). *EMBO*, Submitted.

Wu, C. J., Chen, Z., Ullrich, A., Greene, M. I. & O'Rourke, D. M. (2000) Inhibition of EGFR-mediated phosphoinositide-3-OH kinase (PI3-K) signaling and glioblastoma phenotype by signal-regulatory proteins (SIRPs) *Oncogene* 19, 3999-4010.

Wu, X., Senechal, K., Neshat, M. S., Whang, Y. E. & Sawyers, C. L. (1998) The PTEN/MMAC1 tumor suppressor phosphatase functions as a negative regulator of the phosphoinositide 3-kinase/Akt pathway *Proc Natl Acad Sci USA* 95, 15587-91.

Yamauchi, K. & Pessin, J. E. (1995) Epidermal growth factor-induced association of the SHPTP2 protein tyrosine phosphatase with a 115-kDa phosphotyrosine protein *J Biol Chem* 270, 14871-4.

Ye, D., Mendelsohn, J. & Fan, Z. (1999) Augmentation of a humanized anti-HER2 mAb 4D5 induced growth inhibition by a human-mouse chimeric anti-EGF receptor mAb C225 *Oncogene* 18, 731-738.

Zhang, X., Gaubin, M., Briant, L., Srikantan, V., Murali, R., Saragovi, U., Weiner, D., Devaux, C., Autiero, M., Piatier-Tonneau, D. & Greene, M. I. (1997) Synthetic CD4 exocyclics inhibit binding of human immunodeficiency virus type 1 envelope to CD4 and virus replication in T lymphocytes *Nat Biotechnol* 15, 150-4.

Zhang, X., Piatiertonneau, D., Auffray, C., Murali, R., Mahapatra, A., Zhang, F. Q., Maier, C. C., Saragovi, H. & Greene, M. I. (1996) Synthetic Cd4 Exocyclic Peptides Antagonize Cd4 Holoreceptor Binding and T-Cell Activation *Nature Biotechnology* 14, 472-475.

Zuckermann, R. N. (1993) The chemical synthesis of peptidomimetic libraries *Curr. Opin. Struct. Biol.* 3, 580-4.

Each reference cited herein is hereby incorporated by reference in its entirety.

We claim:

1. An isolated dual-specificity antibody having specificity for both an activated erbB2 receptor and erbB1 dimers, without significant affinity for monomeric EGFr that is not activated,
wherein the antibody has the same binding specificity as an antibody produced by a cell line 8A4 having the assigned accession number PTA-4565 or a cell line A10A12 having the assigned accession number PTA-4566.

2. The isolated antibody of claim 1 wherein the antibody has an affinity for the activated erbB2 receptor that is at least about 10-fold greater than the affinity the antibody has for the erbB2 receptor that is not activated.

3. The isolated antibody of claim 1 wherein the antibody has an affinity for the activated erbB2 receptor that is at least about 100-fold greater than the affinity the antibody has for the erbB2 receptor that is not activated.

4. The isolated antibody of claim 1 wherein the antibody has specificity for one or more cystine knot regions on the activated erbB2 receptor and erbB 1 dimers.

5. The isolated antibody of claim 4 wherein the antibody has a binding constant of at least $5 \times 10^6$ Ka for each activated erbB2 receptor and erbB 1 dimer.

6. The isolated antibody of claim 5 wherein the antibody has a binding constant of at least $1 \times 10^7$ Ka for each activated erbB2 receptor and erbB 1 dimer.

7. The isolated antibody of claim 6 wherein the antibody has a binding constant of at least $2 \times 10^7$ Ka for each activated erbB2 receptor and erbB 1 dimer.

8. The isolated antibody of claim 7 wherein the antibody has a binding constant of at least $1 \times 10^8$ Ka for each activated erbB2 receptor and erbB 1 dimer.

9. The isolated antibody of claim 1 wherein the antibody is selected from the group consisting of a monoclonal antibody, a humanized antibody, a camelized antibody, a chimeric antibody, a primatized antibody, a phage-displayed antibody, a FAb fragment thereof, or a F(Ab)$_2$ fragment thereof.

10. The isolated antibody of claim 1 wherein the antibody binds to an assembly domain of the receptor.

11. The isolated antibody of claim 10 wherein the assembly domain is a cystine knot.

12. The isolated antibody of claim 4 wherein said isolated antibody binds to sub domain IV of said activated erbB 1 receptor.

13. The isolated antibody of claim 1 wherein the antibody is produced by a cell line 8A4 having the assigned accession number PTA-4565 or a cell line A10A12 having the assigned accession number PTA-4566.

14. The isolated antibody of claim 13 wherein the antibody is produced by the cell line 8A4 having the assigned accession number PTA-4565.

15. The isolated antibody of claim 1 wherein the antibody is conjugated to a radioactive agent, a chemotherapeutic agent or an imaging agent.

16. The antibody of claim 15 wherein the radioactive agent is $^{47}$Sc, $^{67}$Cu, $^{90}$Y, $^{86}$Y, $^{109}$Pd, $^{123}$I, $^{125}$I, $^{131}$I, $^{186}$Re, $^{199}$Au, $^{211}$At, $^{212}$Pb, $^{18}$F or $^{212}$Bi.

17. The isolated antibody of claim 15 wherein the antibody is conjugated to a chemotherapeutic agent and wherein the chemotherapeutic agent is selected from the group consisting of methotrexate (amethopterin), doxorubicin (adrimycin), daunorubicin, cytosinarabinoside, etoposide, 5-4 fluorouracil, melphalan, chlorambucil, cyclophosphamide, cis-platin, vindesine, mitomycin, bleomycin, tamoxiphen, taxol, ricin, ricin A chain, *Pseudomonas exotoxin* (PE), diphtheria toxin (DT), *Clostridium perfringens* phospholipase C (PLC), bovine pancreatic ribonuclease (BPR), pokeweed antiviral protein (PAP), abrin, abrin A chain, cobra venom factor (CVF), gelonin (GEL), saporin (SAP), modeccin, viscumin and volkensin.

18. The isolated antibody of claim 15 wherein the antibody is conjugated to an imaging agent and wherein the imaging agent is $^{43}$K, $^{52}$Fe, $^{57}$Co, $^{67}$Cu, $^{67}$Ga, $^{68}$Ga, $^{77}$Br, $^{81}$Rb, $^{81M}$Kr, $^{87M}$Sr, $^{86}$Y, $^{90}$Y, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb, $^{206}$Bi, $^{18}$F, a heavy metal or a positron emitter of oxygen, nitrogen, iron, carbon, or gallium.

19. The isolated antibody of claim 18 wherein the heavy metal is selected from the group consisting of a chelate of iron, gadolinium and manganese.

20. A composition comprising the isolated antibody of claim 1 and a pharmaceutically acceptable carrier, excipient, or diluent.

21. The composition of claim 20 wherein the composition is an injectable composition.

22. The composition of claim 20 further comprising a chemotherapeutic agent or an imaging agent.

23. The composition of claim 21 further comprising a therapeutically effective amount of methotrexate (amethopterin), doxorubicin (adriamycin), daunorubicin, cytosinarabinoside, etoposide, 5-4 fluorouracil, melphalan, chlorambucil, cyclophosphamide, cis-platin, vindesine, mitomycin, bleomycin, tamoxiphen, or taxol.

24. A method of treating an individual who has an erbB2/erbB 1 tumor which comprises administering to said individual a pharmaceutical composition comprising the antibody according to claim 1 and a pharmaceutically acceptable excipient.

25. The method of claim 24 further comprising exposing said individual to radiation.

26. The method of claim 24 further comprising exposing said individual to a chemotherapeutic agent.

27. A method of imaging an erbB1/erbB2 tumor in a patient suffering from an erbB1/erbB2 tumor which comprises administering to said patient a pharmaceutical composition comprising (i) the antibody according to claim 15, said antibody being conjugated to an imaging agent, and (ii) a pharmaceutically acceptable excipient, and detecting binding of the antibody to the erbB1/erbB2 tumor.

28. A method of inhibiting progression of transformation or tumorigenesis of a cell that expresses erbB 1 and erbB2 in an individual who has a predisposition for developing erbB1/erbB2 tumor, who has had an erbB1/erbB2 tumor removed or who has had an erbB 1/erbB2 cancer enter remission, which comprises administering to said individual a pharmaceutical composition comprising the antibody according to claim 1 and a pharmaceutically acceptable excipient.

29. The method of claim 28 which comprises inhibiting said cell from becoming a transformed tumor cell.

30. A method of treating a patient suffering from an erbB tumor which comprises administering to the patient the antibody according to claim 1 and a chemotherapeutic agent.

31. The method of claim 30 wherein said antibody is administered prior to administration of said chemotherapeutic agent.

32. The method of claim 30 wherein said chemotherapeutic agent is administered prior to administration of said antibody.

33. The method of claim 30 wherein said antibody and said chemotherapeutic agent are administered concurrently.

34. A method of treating a patient suffering from an erbB tumor which comprises administering to the patient the antibody according to claim 1 and radiation.

35. The method of claim 34 wherein said antibody is administered prior to administration of radiation.

36. The method of claim 34 wherein radiation is administered prior to administration of said antibody.

37. The method of claim 34 wherein said antibody and radiation are administered concurrently.

38. The isolated antibody of claim 1, wherein the antibody specifically binds to at least one activation epitope in the extracellular region of the activated erbB2 receptor.

39. The isolated antibody of claim 1, wherein the antibody has an affinity for the activated erbB2 receptor that is at least about 5-fold greater than the affinity the antibody has for the erbB2 receptor that is not activated.

* * * * *

UNITED STATES PATENT AND TRADEMARK OFFICE
CERTIFICATE OF CORRECTION

| | |
|---|---|
| PATENT NO. | : 7,662,374 B2 |
| APPLICATION NO. | : 10/213292 |
| DATED | : February 16, 2010 |
| INVENTOR(S) | : Greene et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 409 days.

Signed and Sealed this

Thirtieth Day of November, 2010

David J. Kappos
*Director of the United States Patent and Trademark Office*

SEQUENCE LISTING

```
<160> NUMBER OF SEQ ID NOS: 45

<210> SEQ ID NO 1
<211> LENGTH: 7
<212> TYPE: PRT
<213> ORGANISM: Artificial Sequence
<220> FEATURE:
<223> OTHER INFORMATION: synthetic sequence

<400> SEQUENCE: 1

Phe Pro Asp Glu Glu Gly Ala
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic sequence

<400> SEQUENCE: 2

Phe Tyr Pro Asp Glu Glu Gly Ala
1               5

<210> SEQ ID NO 3
<211> LENGTH: 11
<212> TYPE: PRT
<213> ORGANISM: Artificial Sequence
<220> FEATURE:
<223> OTHER INFORMATION: ErbB2-S22-AFA peptide

<400> SEQUENCE: 3

Tyr Cys Phe Pro Asp Glu Glu Gly Ala Cys Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic sequence

<400> SEQUENCE: 4

Ser Tyr Cys Phe Pro Asp Glu Glu Gly Ala Cys Tyr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: synthetic sequence

<400> SEQUENCE: 5

Gly Ser Tyr Cys Phe Pro Asp Glu Glu Gly Ala Cys Tyr
1               5                   10
```

```
<210> SEQ ID NO 6
<211> LENGTH: 14
<212> TYPE: PRT
<213> ORGANISM: Artificial Sequence
<220> FEATURE:
<223> OTHER INFORMATION: synthetic sequence

<400> SEQUENCE: 6

Gly Gly Ser Tyr Cys Phe Pro Asp Glu Glu Gly Ala Cys Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: synthetic sequence

<400> SEQUENCE: 7

Gly Gly Gly Ser Tyr Cys Phe Pro Asp Glu Glu Gly Ala Cys Tyr
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: synthetic sequence

<400> SEQUENCE: 8

Tyr Cys Phe Pro Asp Glu Glu Gly Ala Cys Tyr Gly
1               5                   10

<210> SEQ ID NO 9
<211> LENGTH: 13
<212> TYPE: PRT
<213> ORGANISM: Artificial Sequence
<220> FEATURE:
<223> OTHER INFORMATION: synthetic sequence

<400> SEQUENCE: 9

Tyr Cys Phe Pro Asp Glu Glu Gly Ala Cys Tyr Gly Gly
1               5                   10

<210> SEQ ID NO 10
<211> LENGTH: 14
<212> TYPE: PRT
<213> ORGANISM: Artificial Sequence
<220> FEATURE:
<223> OTHER INFORMATION: synthetic sequence

<400> SEQUENCE: 10

Tyr Cys Phe Pro Asp Glu Glu Gly Ala Cys Tyr Gly Gly Gly
1               5                   10

<210> SEQ ID NO 11
<211> LENGTH: 15
<212> TYPE: PRT
<213> ORGANISM: Artificial Sequence
<220> FEATURE:
<223> OTHER INFORMATION: synthetic sequence

<400> SEQUENCE: 11

Tyr Cys Phe Pro Asp Glu Glu Gly Ala Cys Tyr Gly Gly Gly Ser
1               5                   10                  15

<210> SEQ ID NO 12
```

-continued

```
<211> LENGTH: 12
<212> TYPE: PRT
<213> ORGANISM: Artificial Sequence
<220> FEATURE:
<223> OTHER INFORMATION: synthetic sequence

<400> SEQUENCE: 12

Tyr Cys Phe Tyr Pro Asp Glu Glu Gly Ala Cys Tyr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: synthetic sequence

<400> SEQUENCE: 13

Ser Tyr Cys Phe Tyr Pro Asp Glu Glu Gly Ala Cys Tyr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: synthetic sequence

<400> SEQUENCE: 14

Gly Ser Tyr Cys Phe Tyr Pro Asp Glu Glu Gly Ala Cys Tyr
1               5                   10

<210> SEQ ID NO 15
<211> LENGTH: 15
<212> TYPE: PRT
<213> ORGANISM: Artificial Sequence
<220> FEATURE:
<223> OTHER INFORMATION: synthetic sequence

<400> SEQUENCE: 15

Gly Gly Ser Tyr Cys Phe Tyr Pro Asp Glu Glu Gly Ala Cys Tyr
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: synthetic sequence

<400> SEQUENCE: 16

Gly Gly Gly Ser Tyr Cys Phe Tyr Pro Asp Glu Glu Gly Ala Cys Tyr
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: synthetic sequence

<400> SEQUENCE: 17

Tyr Cys Phe Tyr Pro Asp Glu Glu Gly Ala Cys Tyr Gly
1               5                   10

<210> SEQ ID NO 18
<211> LENGTH: 14
```

```
<212> TYPE: PRT
<213> ORGANISM: Artificial Sequence
<220> FEATURE:
<223> OTHER INFORMATION: synthetic sequence

<400> SEQUENCE: 18

Tyr Cys Phe Tyr Pro Asp Glu Glu Gly Ala Cys Tyr Gly Gly
1               5                   10

<210> SEQ ID NO 19
<211> LENGTH: 15
<212> TYPE: PRT
<213> ORGANISM: Artificial Sequence
<220> FEATURE:
<223> OTHER INFORMATION: synthetic sequence

<400> SEQUENCE: 19

Tyr Cys Phe Tyr Pro Asp Glu Glu Gly Ala Cys Tyr Gly Gly Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: synthetic sequence

<400> SEQUENCE: 20

Tyr Cys Phe Tyr Pro Asp Glu Glu Gly Ala Cys Tyr Gly Gly Gly Ser
1               5                   10                  15

<210> SEQ ID NO 21
<211> LENGTH: 4
<212> TYPE: PRT
<213> ORGANISM: Artificial Sequence
<220> FEATURE:
<223> OTHER INFORMATION: synthetic sequence

<400> SEQUENCE: 21

Gly Gly Ser Tyr
1

<210> SEQ ID NO 22
<211> LENGTH: 5
<212> TYPE: PRT
<213> ORGANISM: Artificial Sequence
<220> FEATURE:
<223> OTHER INFORMATION: synthetic sequence

<400> SEQUENCE: 22

Gly Gly Gly Ser Tyr
1               5

<210> SEQ ID NO 23
<211> LENGTH: 4
<212> TYPE: PRT
<213> ORGANISM: Artificial Sequence
<220> FEATURE:
<223> OTHER INFORMATION: synthetic sequence

<400> SEQUENCE: 23

Tyr Gly Gly Gly
1

<210> SEQ ID NO 24
<211> LENGTH: 5
<212> TYPE: PRT
```

<213> ORGANISM: Artificial Sequence
<220> FEATURE:
<223> OTHER INFORMATION: synthetic sequence

<400> SEQUENCE: 24

Tyr Gly Gly Gly Ser
1               5

<210> SEQ ID NO 25
<211> LENGTH: 12
<212> TYPE: PRT
<213> ORGANISM: Artificial Sequence
<220> FEATURE:
<223> OTHER INFORMATION: synthetic sequence

<400> SEQUENCE: 25

Tyr Cys Phe Pro Asp Glu Glu Gly Ala Cys Tyr Lys
1               5                  10

<210> SEQ ID NO 26
<211> LENGTH: 14
<212> TYPE: PRT
<213> ORGANISM: Artificial Sequence
<220> FEATURE:
<223> OTHER INFORMATION: synthetic sequence

<400> SEQUENCE: 26

Tyr Cys Phe Pro Asp Glu Glu Gly Ala Cys Tyr Gly Gly Ser
1               5                  10

<210> SEQ ID NO 27
<211> LENGTH: 4
<212> TYPE: PRT
<213> ORGANISM: Artificial Sequence
<220> FEATURE:
<223> OTHER INFORMATION: synthetic sequence

<400> SEQUENCE: 27

Tyr Gly Gly Ser
1

<210> SEQ ID NO 28
<211> LENGTH: 29
<212> TYPE: PRT
<213> ORGANISM: Artificial Sequence
<220> FEATURE:
<223> OTHER INFORMATION: synthetic sequence

<400> SEQUENCE: 28

Cys Lys Val Glu Leu Met Tyr Pro Pro Pro Tyr Phe Val Gly Met Gly
1               5                  10                  15

Asn Gly Thr Gln Ile Tyr Val Ile Asp Pro Glu Pro Cys
            20                  25

<210> SEQ ID NO 29
<211> LENGTH: 30
<212> TYPE: PRT
<213> ORGANISM: Artificial Sequence
<220> FEATURE:
<223> OTHER INFORMATION: synthetic sequence

<400> SEQUENCE: 29

Cys Lys Ile Glu Phe Met Tyr Pro Pro Pro Tyr Leu Asp Asn Glu Arg
1               5                  10                  15

Ser Asn Gly Thr Ile Ile His Ile Lys Glu Lys His Leu Cys
            20                  25                  30

<210> SEQ ID NO 30
<211> LENGTH: 29
<212> TYPE: PRT
<213> ORGANISM: Artificial Sequence
<220> FEATURE:
<223> OTHER INFORMATION: synthetic sequence

<400> SEQUENCE: 30

Cys Ser Leu Ser Ile Phe Asp Pro Pro Phe Gln Glu Arg Asn Leu
1               5                   10                  15

Ser Gly Gly Tyr Leu His Ile Tyr Glu Ser Gln Leu Cys
            20                  25

<210> SEQ ID NO 31
<211> LENGTH: 13
<212> TYPE: PRT
<213> ORGANISM: Artificial Sequence
<220> FEATURE:
<223> OTHER INFORMATION: erbB2-S22-APE peptide

<400> SEQUENCE: 31

Tyr Cys Pro Ile Trp Lys Phe Pro Asp Glu Glu Cys Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: erbB1-S22-ALG peptide

<400> SEQUENCE: 32

Tyr Cys Leu Val Trp Lys Tyr Ala Asp Ala Gly Cys Tyr
1               5                   10

<210> SEQ ID NO 33
<211> LENGTH: 13
<212> TYPE: PRT
<213> ORGANISM: Artificial Sequence
<220> FEATURE:
<223> OTHER INFORMATION: erbB3-S22-APQ peptide

<400> SEQUENCE: 33

Tyr Cys Pro Ile Tyr Lys Tyr Pro Asp Val Gln Cys Tyr
1               5                   10

<210> SEQ ID NO 34
<211> LENGTH: 13
<212> TYPE: PRT
<213> ORGANISM: Artificial Sequence
<220> FEATURE:
<223> OTHER INFORMATION: erbB4-S22-AFD peptide

<400> SEQUENCE: 34

Tyr Cys Phe Ile Phe Lys Tyr Ala Asp Pro Asp Cys Tyr
1               5                   10

<210> SEQ ID NO 35
<211> LENGTH: 11
<212> TYPE: PRT
<213> ORGANISM: Artificial Sequence
<220> FEATURE:
<223> OTHER INFORMATION: erbB2-S22-AFA peptide

<400> SEQUENCE: 35

```
Tyr Cys Phe Pro Asp Glu Glu Gly Ala Cys Tyr
1               5                   10
```

<210> SEQ ID NO 36
<211> LENGTH: 29
<212> TYPE: PRT
<213> ORGANISM: Artificial Sequence
<220> FEATURE:
<223> OTHER INFORMATION: synthetic sequence

<400> SEQUENCE: 36

```
Cys Lys Val Glu Leu Met Tyr Pro Pro Tyr Phe Val Gly Met Gly
1               5                   10                  15

Asn Gly Thr Gln Ile Tyr Val Ile Asp Pro Glu Pro Cys
                20                  25
```

<210> SEQ ID NO 37
<211> LENGTH: 29
<212> TYPE: PRT
<213> ORGANISM: Artificial Sequence
<220> FEATURE:
<223> OTHER INFORMATION: synthetic sequence

<400> SEQUENCE: 37

```
Cys Lys Val Glu Leu Met Tyr Pro Pro Tyr Phe Val Gly Met Gly
1               5                   10                  15

Asn Gly Thr Gln Ile Tyr Val Ile Asp Pro Glu Pro Cys
                20                  25
```

<210> SEQ ID NO 38
<211> LENGTH: 30
<212> TYPE: PRT
<213> ORGANISM: Artificial Sequence
<220> FEATURE:
<223> OTHER INFORMATION: synthetic sequence

<400> SEQUENCE: 38

```
Pro Cys Pro Ile Asn Cys Thr His Ser Cys Val Asp Leu Asp Lys
1               5                   10                  15

Gly Cys Pro Ala Glu Gln Arg Ala Ser Pro Leu Thr Ser Ile
                20                  25                  30
```

<210> SEQ ID NO 39
<211> LENGTH: 148
<212> TYPE: PRT
<213> ORGANISM: Homo sapiens

<400> SEQUENCE: 39

```
Gln Val Cys His Ala Leu Cys Ser Pro Glu Gly Cys Trp Gly Pro Glu
1               5                   10                  15

Pro Arg Asp Cys Val Ser Cys Arg Asn Val Ser Arg Gly Arg Glu Cys
                20                  25                  30

Val Asp Lys Cys Asn Leu Leu Glu Gly Glu Pro Arg Glu Phe Val Glu
            35                  40                  45

Asn Ser Glu Cys Ile Gln Cys His Pro Glu Cys Leu Pro Gln Ala Met
        50                  55                  60

Asn Ile Thr Cys Thr Gly Arg Gly Pro Asp Asn Cys Ile Gln Cys Ala
65                  70                  75                  80

His Tyr Ile Asp Gly Pro His Cys Val Lys Thr Cys Pro Ala Gly Val
                85                  90                  95

Met Gly Glu Asn Asn Thr Leu Val Trp Lys Tyr Ala Asp Ala Gly His
            100                 105                 110
```

```
Val Cys His Leu Cys His Pro Asn Cys Thr Tyr Gly Cys Thr Gly Pro
            115                 120                 125
Gly Leu Glu Gly Cys Pro Thr Asn Gly Pro Lys Ile Pro Ser Ile Ala
        130                 135                 140
Thr Gly Met Val
145

<210> SEQ ID NO 40
<211> LENGTH: 149
<212> TYPE: PRT
<213> ORGANISM: Homo sapiens

<400> SEQUENCE: 40

Leu Ala Cys His Gln Leu Cys Ala Arg Gly His Cys Trp Gly Pro Gly
1               5                   10                  15
Pro Thr Gln Cys Val Asn Cys Ser Gln Phe Leu Arg Gly Gln Glu Cys
            20                  25                  30
Val Glu Glu Cys Arg Val Leu Gln Gly Leu Pro Arg Glu Tyr Val Asn
        35                  40                  45
Ala Arg His Cys Leu Pro Cys His Pro Glu Cys Gln Pro Gln Asn Gly
    50                  55                  60
Ser Val Thr Cys Phe Gly Pro Glu Ala Asp Gln Cys Val Ala Cys Ala
65                  70                  75                  80
His Tyr Lys Asp Pro Pro Phe Cys Val Ala Arg Cys Pro Ser Gly Val
                85                  90                  95
Lys Pro Asp Leu Ser Tyr Met Pro Ile Trp Lys Phe Pro Asp Glu Glu
            100                 105                 110
Gly Ala Cys Gln Pro Cys Pro Ile Asn Cys Thr His Ser Cys Val Asp
        115                 120                 125
Leu Asp Asp Lys Gly Cys Pro Ala Glu Gln Arg Ala Ser Pro Leu Thr
    130                 135                 140
Ser Ile Ile Ser Ala
145

<210> SEQ ID NO 41
<211> LENGTH: 147
<212> TYPE: PRT
<213> ORGANISM: Homo sapiens

<400> SEQUENCE: 41

Lys Val Cys Asp Pro Leu Cys Ser Ser Gly Gly Cys Trp Gly Pro Gly
1               5                   10                  15
Pro Gly Gln Cys Leu Ser Cys Arg Asn Tyr Ser Arg Gly Gly Val Cys
            20                  25                  30
Val Thr His Cys Asn Phe Leu Asn Gly Glu Pro Arg Glu Phe Ala His
        35                  40                  45
Glu Ala Glu Cys Phe Ser Cys His Pro Glu Cys Gln Pro Met Glu Gly
    50                  55                  60
Thr Ala Thr Cys Asn Gly Ser Gly Ser Asp Thr Cys Ala Gln Cys Ala
65                  70                  75                  80
His Phe Arg Asp Gly Pro His Cys Val Ser Ser Cys Pro His Gly Val
                85                  90                  95
Leu Gly Ala Lys Gly Pro Ile Tyr Lys Tyr Pro Asp Val Gln Asn Glu
            100                 105                 110
Cys Arg Pro Cys His Glu Asn Cys Thr Gln Gly Cys Lys Gly Pro Glu
        115                 120                 125
```

```
Leu Gln Asp Cys Leu Gly Gln Thr Leu Val Leu Ile Gly Lys Thr His
        130                 135                 140
Leu Thr Met
145

<210> SEQ ID NO 42
<211> LENGTH: 148
<212> TYPE: PRT
<213> ORGANISM: Homo sapiens

<400> SEQUENCE: 42

Met Val Cys Asn His Leu Cys Ser Ser Asp Gly Cys Trp Gly Pro Gly
1               5                   10                  15

Pro Asp Gln Cys Leu Ser Cys Arg Arg Phe Ser Arg Gly Arg Ile Cys
            20                  25                  30

Ile Glu Ser Cys Asn Leu Tyr Asp Gly Glu Phe Arg Glu Phe Glu Asn
        35                  40                  45

Gly Ser Ile Cys Val Glu Cys Asp Pro Gln Cys Glu Lys Met Glu Asp
    50                  55                  60

Gly Leu Leu Thr Cys His Gly Pro Gly Pro Asp Asn Cys Thr Lys Cys
65                  70                  75                  80

Ser His Phe Lys Asp Gly Pro Asn Cys Val Glu Lys Cys Pro Asp Gly
                85                  90                  95

Leu Gln Gly Ala Asn Ser Phe Ile Phe Lys Tyr Ala Asp Pro Asp Arg
            100                 105                 110

Glu Cys His Pro Cys His Pro Asn Cys Thr Gln Gly Cys Asn Gly Pro
        115                 120                 125

Thr Ser His Asp Cys Ile Tyr Tyr Pro Trp Thr Gly His Ser Thr Leu
    130                 135                 140

Pro Gln His Ala
145

<210> SEQ ID NO 43
<211> LENGTH: 12
<212> TYPE: PRT
<213> ORGANISM: Artificial Sequence
<220> FEATURE:
<223> OTHER INFORMATION: synthetic sequence

<400> SEQUENCE: 43

Phe Cys Tyr Ile Gly Glu Val Glu Asp Gln Cys Tyr
1               5                   10

<210> SEQ ID NO 44
<211> LENGTH: 31
<212> TYPE: DNA
<213> ORGANISM: Artificial Sequence
<220> FEATURE:
<223> OTHER INFORMATION: synthetic primer

<400> SEQUENCE: 44
cgcccggatc ctggcctgcc accagctgtg c                              31

<210> SEQ ID NO 45
<211> LENGTH: 33
<212> TYPE: DNA
<213> ORGANISM: Artificial Sequence
<220> FEATURE:
<223> OTHER INFORMATION: synthetic primer
```

-continued

```
<400> SEQUENCE: 45
cgcccgcggc cgccgcagag atgatggagt cag                                   33
```